(12) United States Patent
Gorath

(10) Patent No.: US 11,166,931 B2
(45) Date of Patent: *Nov. 9, 2021

(54) INDUCTION OF ARTERIOGENESIS WITH AN NO (NITRIC OXIDE) DONOR

(71) Applicant: G. Pohl-Boskamp GmbH & Co. KG, Hohenlockstedt (DE)

(72) Inventor: Michaela Gorath, Hamburg (DE)

(73) Assignee: G. POHL-BOSKAMP GMBH & CO. KG, Hohenlockstedt (DE)

( * ) Notice: Subject to any disclaimer, the term of this patent is extended or adjusted under 35 U.S.C. 154(b) by 273 days.

This patent is subject to a terminal disclaimer.

(21) Appl. No.: 15/450,656

(22) Filed: Mar. 6, 2017

(65) Prior Publication Data

US 2017/0172966 A1    Jun. 22, 2017

Related U.S. Application Data

(63) Continuation of application No. 14/403,713, filed as application No. PCT/EP2013/061131 on May 29, 2013, now abandoned.

(60) Provisional application No. 61/653,595, filed on May 31, 2012.

(30) Foreign Application Priority Data

May 31, 2012   (EP) .................................. 12004187

(51) Int. Cl.
  *A61K 31/21*     (2006.01)
  *A61K 33/00*     (2006.01)
  *A61K 31/5377*   (2006.01)
  *A61K 31/295*    (2006.01)
  *A61K 31/455*    (2006.01)
  *A61K 31/34*     (2006.01)

(52) U.S. Cl.
  CPC ............ *A61K 31/21* (2013.01); *A61K 31/295* (2013.01); *A61K 31/34* (2013.01); *A61K 31/455* (2013.01); *A61K 31/5377* (2013.01); *A61K 33/00* (2013.01)

(58) Field of Classification Search
  CPC .................................................... A61K 31/21
  See application file for complete search history.

(56) References Cited

U.S. PATENT DOCUMENTS

| | | |
|---|---|---|
| 3,155,574 A | 11/1964 | Silson et al. |
| 4,323,577 A | 4/1982 | Ohkuma et al. |
| 4,542,013 A | 9/1985 | Keith |
| 4,671,953 A | 6/1987 | Stanley et al. |
| 4,919,919 A | 4/1990 | Kouda et al. |
| 5,047,230 A | 9/1991 | Nagy et al. |
| 5,186,925 A | 2/1993 | Cholcha |
| 5,370,862 A | 12/1994 | Klokkers-Bethke et al. |
| 5,698,589 A | 12/1997 | Allen |
| 5,744,124 A | 4/1998 | Klokkers-Bethke et al. |
| 5,989,529 A | 11/1999 | Kaplan |
| 6,443,307 B1 | 9/2002 | Burridge |
| 6,962,691 B1 | 11/2005 | Lulla et al. |
| 7,781,226 B2 | 8/2010 | McDevitt et al. |
| 7,872,049 B2* | 1/2011 | Groteluschen .......... A61K 9/006 514/645 |
| 8,147,872 B2 | 4/2012 | Crew et al. |
| 9,101,592 B2* | 8/2015 | Zimmeck ............. A61K 9/0056 |
| 9,176,529 B2 | 11/2015 | Hata |
| 9,248,099 B2* | 2/2016 | Gorath .................. A61K 31/34 |
| 9,616,023 B2* | 4/2017 | Zimmeck ............. A61K 9/0056 |
| 9,675,552 B2* | 6/2017 | Gorath ................ A61K 31/616 |
| 10,034,850 B2* | 7/2018 | Gerber ................ A61K 9/0014 |
| 10,987,332 B2* | 4/2021 | Gerber .................... A61K 9/08 |
| 2002/0032232 A1 | 3/2002 | Bing |
| 2003/0026849 A1 | 2/2003 | Thomas |
| 2003/0078517 A1 | 4/2003 | Kensey |
| 2003/0095925 A1 | 5/2003 | Dugger, III |
| 2004/0213744 A1 | 10/2004 | Lulla et al. |
| 2004/0228883 A1 | 11/2004 | Karl |
| 2005/0191620 A1 | 9/2005 | McDevitt et al. |
| 2005/0192210 A1 | 9/2005 | Rothbard et al. |
| 2006/0003011 A1 | 1/2006 | Crew et al. |
| 2007/0053966 A1 | 3/2007 | Ang et al. |
| 2007/0059346 A1 | 3/2007 | Maibach |
| 2008/0260861 A1 | 10/2008 | Hagendoorn et al. |
| 2009/0221540 A1 | 9/2009 | Bennink |
| 2010/0016446 A1 | 1/2010 | Gonad et al. |
| 2010/0184870 A1 | 7/2010 | Groteluschen et al. |
| 2010/0216893 A1 | 8/2010 | Groteluschen et al. |

(Continued)

FOREIGN PATENT DOCUMENTS

| | | |
|---|---|---|
| CA | 2718345 | 9/2009 |
| CA | 2778679 | 11/2013 |

(Continued)

OTHER PUBLICATIONS

Dennis et al. Annals of Internal Medicine 1980, 92, 799-800 (Year: 1980).*
Pfizer, Nitrostat (Nitroglycerin Sublingual Tablets, USP), 2010, pp. 4-11 (Year: 2010).*
Maxwell et al. Postgrad. Med. J. 1992, 68, 857-866 (Year: 1992).*
Lehouxetal. Circ. Res. 2006, 99, 567-569 (Year: 2006).*
Goto et al. AJH 2007, 20, 825-830 (Year: 2007).*
Winsoretal. American Heart Journal 1975, 90, 611-626 (Year: 1975).*
Riseman et al. Circulation, vol. XVII, 1954, 22-39 (Year: 1954).*
Thadani et al. Cardiovasculr Drugs and Therapy 1994, 8, 611-623 (Year: 1994).*

(Continued)

*Primary Examiner* — Matthew P Coughlin
(74) *Attorney, Agent, or Firm* — Dechert LLP; Andrew T. Wilkins; Robin L. Brese

(57) ABSTRACT

The present invention inter alia relates to a method of promoting collateral circulation comprising the step of exposing a subject to a therapeutically effective amount of an NO donor wherein the therapeutically effective amount of the NO donor promotes arteriogenesis sufficient to augment collateral circulation in a physiological or pathological condition.

16 Claims, 30 Drawing Sheets

(56) References Cited

U.S. PATENT DOCUMENTS

Figure 1:
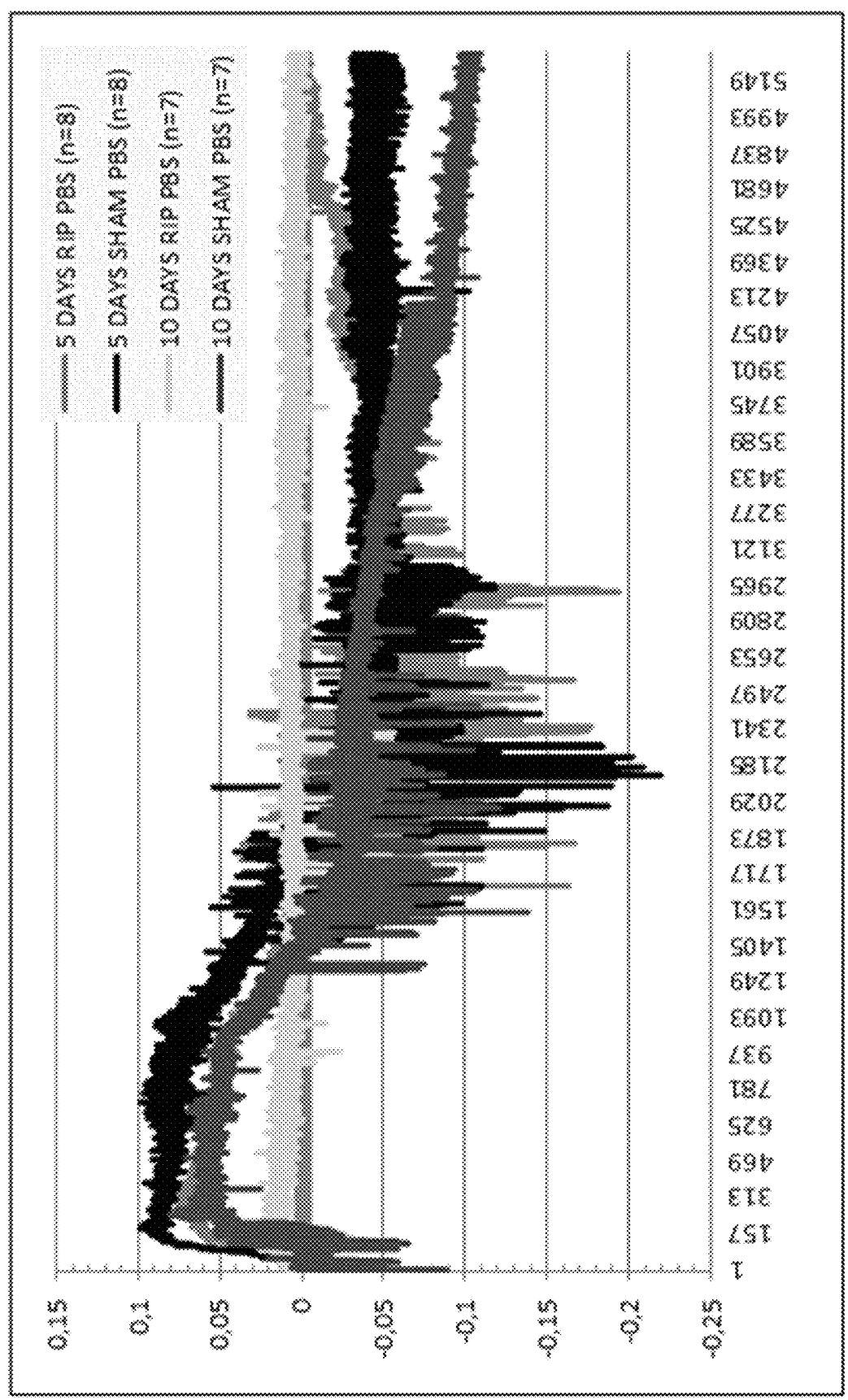

| | | |
|---|---|---|
| 2010/0227922 A1 | 9/2010 | Groteluschen et al. |
| 2011/0002987 A1 | 1/2011 | Poll et al. |
| 2011/0240508 A1 | 10/2011 | Groteluschen et al. |
| 2012/0237567 A1 | 9/2012 | Hagendoorn et al. |
| 2013/0121930 A1 | 5/2013 | Boskamp |
| 2014/0057977 A1 | 2/2014 | Gorath |
| 2016/0296488 A1 | 10/2016 | Gerber et al. |
| 2016/0367512 A1 | 12/2016 | Gorath |
| 2019/0008815 A1 | 1/2019 | Gerber et al. |
| 2019/0365693 A1 | 12/2019 | Gorath |
| 2020/0276145 A1 | 9/2020 | Boskamp |

FOREIGN PATENT DOCUMENTS

| | | |
|---|---|---|
| CN | 101229148 | 7/2008 |
| DE | 3246081 | 6/1984 |
| DE | 3922650 | 1/1990 |
| DE | 4038203 | 6/1992 |
| DE | 202008007318 | 9/2008 |
| DE | 102008005484 | 7/2009 |
| EP | 0448961 | 10/1991 |
| EP | 0461505 | 12/1991 |
| EP | 0471161 | 2/1992 |
| EP | 1004294 | 5/2000 |
| EP | 2668947 | 12/2013 |
| EP | 2668948 | 12/2013 |
| EP | 2805730 A1 | 11/2014 |
| EP | 2854794 | 4/2015 |
| GB | 1205019 | 9/1970 |
| JP | 05-500041 A | 1/1993 |
| RU | 2174838 | 10/2001 |
| WO | 82/00005 | 1/1982 |
| WO | 88/05306 | 7/1988 |
| WO | 96/27372 | 9/1996 |
| WO | 97/38687 | 10/1997 |
| WO | 99/17766 | 4/1999 |
| WO | 99/38472 | 8/1999 |
| WO | 01/43735 | 6/2001 |
| WO | 01/68062 | 9/2001 |
| WO | 03/066472 | 8/2003 |
| WO | 2004064779 | 8/2004 |
| WO | 2005/004989 | 1/2005 |
| WO | 2005107461 | 11/2005 |
| WO | 2007/123955 | 11/2007 |
| WO | 2008105731 | 9/2008 |
| WO | 2009/092358 | 7/2009 |
| WO | WO-2009092358 A1 * 7/2009 | ............. A61K 31/15 |
| WO | 11/02606 | 1/2011 |
| WO | WO 2011/002606 A1 | 1/2011 |
| WO | 2013178713 | 12/2013 |
| WO | WO 2013/178713 A1 | 12/2013 |

OTHER PUBLICATIONS

Logue et al. Circulation, vol. XLVI, 1972, 1132-1145 (Year: 1972).*
Eisaku Nakane et al. "Exercise therapy for heart failure" Nippon Rinsko, (2006), vol. 64, No. 5, pp. 962-967.
Drug Register, Encyclopedia of Drugs, Annual Book, edition 10, 2003, p. 586.
Molecularinfo.com reference [Retrieved on Dec. 1, 2010 from the Internet: <URL: http://www.molecularinfo.com/MTM/D/D3/D3-r/D3-4-60.html], 1 pg.
Nitrolingual Pumpspray product insert (nitroglycerin lingual spray), G. Pohl-Boskamp GmbH & Co. KG, Oct. 2008, 4 pgs.
Nitrolingual Pumpspray package labelling (nitroglycerin lingual spray), G. Pohl Boskamp GmbH & Co. KG, Nov. 2008, 1 pg.
Nitrolingual Pumpspray bottle labelling (nitroglycerin lingual spray), G. Pohl-Boskamp GmbH & Co. KG, May 2006, 2 pgs.
Scheife et al., Journal of Pharmaceutical Sciences, vol. 71, Issue 1, Abstract, 1982, 1 pg.
Schranz et al., (1981), "Hemorrhagic pulmonary edema and cardiac failure following isolated head injury. Treatment with dobutamine and nitroglycerin," Monatsschr Kinderheilkd, 129 (4): 248-250. Abstract.
Kuroda et al., (1997), "Changes in cerebral blood flow accompanied with reduction of blood pressure treatment in patients with hypertensive intracerebral hemorrhages," Neurol Res., 19(2): 169-73. Abstract.
International Search Report for International Application No. PCT/EP2011/003890, dated Nov. 11, 2011. 6 pages.
Written Opinion for International Application No. PCT/EP2011/003890, dated Nov. 11, 2011. 9 pages.
Fernandes et al., (2004), "Involvement of guanylate cyclase and potassium channels on the delayed phase of mouse carrageenan-induced paw edema," European Journal of Pharmacology, Elsevier Science, NL, vol. 501, No. 1-3, pp. 209-214.
Beltrame et al., (1998) "Nitrate therapy is an alternative to furosemidel morphine therapy in the management of acute cardiogenic pulmonary edema," Journal of Cardiac Failure, vol. 4, No. 4, pp. 271-279.
International Search Report for International Application No. PCT/EP2009/001772, dated Jun. 16, 2009. 3 pages.
Written Opinion for International Application No. PCT/EP2009/001772, dated Jun. 16, 2009. 4 pages.
International Search Report for International Application No. PCT/EP2012/000803, dated Jun. 25, 2012. 4 pages.
Written Opinion for International Application No. PCT/EP2012/000803, dated Jun. 25, 2012. 7 pages.
M. J. Pikal et al: "Vapor pressure of nitroglycerin in sublingual molded tablets: Implications for stability", Journal of Pharmaceutical Sciences, 1976, vol. 65, No. 9, pp. 1278-1284.
M. J. Pikal et al: "Polymer sorption of nitroglycerin and stability of molded nitroglycerin tablets in unit-dose packaging", Journal of Pharmaceutical Sciences, 1977, vol. 66, No. 9, pp. 1293-1297.
M. J. Pikal et al: "Effect of nitroglycerin-soluble additives on the stability of molded nitroglycerin tablets", Journal of Pharmaceutical Sciences, 1984, vol. 73, No. 11, pp. 1608-1612.
"Glyceryl Monostearate", In: R C Rowe. P J Sheskey. S C Owen: "Handbook of Pharmaceutical Excipients, 5th Edition", 2005, Pharmaceutical Press, London.
International Search Report for International Application No. PCT/EP2012/000802, dated Jun. 6, 2012. 4 pages.
Written Opinion for International Application No. PCT/EP2012/000802, dated Jun. 6, 2012. 6 pages.
"Barex Resins", INEOS Barex, USA, 2006, Retrieved from the Internet: URL:http://www.ineosbarex.com/files/upload/Ineos%20Barex%20Brochure.pdf, retrieved on May 15, 2012, the whole document.
Database Caplus [Online], Chemical Abstracts Service, Columbus, Ohio, US, 2004, Chen, Baoxi et al: "Effect of acrylonitrile-butadiene rubber on nitroglycerin migration from propellant to EPDM inhibitor", retrieved from STN, Database accession No. 2004:826842, abstract.
Daniel Banes: "Deterioration of nitroglycerin tablets", Journal of Pharmaceutical Sciences, vol. 57, No. 5, 1968, pp. 893-894.
European Search Report for EP12004187, Date of completion of search Sep. 28, 2012.
Cui X, et al., "Role of endothelial nitric oxide synthetase in arteriogenesis after stroke in mice", Neuroscience, New York, NY, US, vol. 159, No. 2, 2009, pp. 744-750.
Dinesh Kumar, et al., "Chronic sodium nitrite therapy augments ischemia-induced angiogenesis and arteriogenesis", Proceedings of the National Academy of Sciences, National Academy of Sciences, US, vol. 105, No. 21, 2008, pp. 7540-7545.
Hopkins et al., "Controlled delivery of vascular endothelial growth factor promotes neovascularization and maintains limb function in a rabbit model of ischemia", Journal of Vascular Surgery, C.V. Mosby CO., St Louis, MO, US, vol. 27, No. 5, 1998, pp. 886-895.
Persson et al., "Therapeutic artergenesis in peripheral arterial disease: Combining Intervention and Passive Training", Vasa Journal for Vascular Diseases, vol. 40, No. 3, 2011, pp. 177-187.
Sager H.B. et al., "Temporal patterns of blood flow and nitric oxide synthase expression affect macrophage accumulation and proliferation during collateral growth", J Angiogenes Res, 2010, vol. 2, No. 18, pp. 1-11.

(56) References Cited

OTHER PUBLICATIONS

Troidl K., et al., "Effects of Endogenous Nitric Oxide and of DETA NONOate in Arteriogenesis", J Cardiovsc Pharmacol, 2010, vol. 55, No. 2, pp. 153-160.
Troidl K. and Schaper W, "Arteriogenesis versus angiogenesis in peripheral artery disease", Diabetes/Metabolism Research and Reviews, 2012, vol. 28, S1, pp. 27-29.
Abrams, J., "Mechanisms of Action of the Organic Nitrates in the Treatment of Myocardial Ischemia" The American Journal of Cardiology, (1992), vol. 70(8), pp. 30B-42B.
Abrams, J., "Glyceryl Trinitrate (Nitroglycerin) and the Organic Nitrates Choosing the Method of Administration" Practical Therapeutics, Division of Cardiology, Drugs 34(3), (1987), pp. 391-403.
Database WPI, XP002662296 & RU 2174838C2, Ivan MED ACAD, Week 200202, Thomson Scientific, [2001] Abstract.
U.S. Appl. No. 13/904,229, dated May 29, 2013.
Sergio H. Ferreira et al., "Blockade of hyperalgesia and neurogenic oedema by topical application of nitroglycerin," European Journal of Pharmacology, 1992, vol. 217, pp. 207-209.
Johns Hopkins Sports Medicine Patient Guide to Muscle Strain; date unavailable; Johns Hopkins Medicine, Orthopaedic Surgery [online], [retrieved Jan. 20, 2015], Retrieved from the Internet: <URL: http://www.hopkinsortho.org/muscle_strain.html>.
Definition of Bruise; 1996-2015, last editorial review Mar. 19, 2012; MedicineNet [online], [retrieved Jan. 20, 2015] Retrieved from the Internet: <URL: http://www.medicinenet.com/script/main/art.asp?articlekey=2541>.
Edema, Dictionary.com [online], [retrieved Jun. 18, 2015] Retrieved from the Internet; <URL:http://dictionary.reference.com/browse/edema>.
Fernandes et al., "Nitric oxide-induced inhibition of mouse paw edema: involvement of soluble guanylate cyclase and potassium channels," Inflammation Research, 2002, vol. 51, pp. 377-384.
Zegarska et al., "Clinical and experimental aspects of cutaneous neurogenic inflammation" Pharmacological Reports, [2006], vol. 58, pp. 13-21.
D. J. Danziger et al. "Automated site-directed drug design: a general algorithm for knowledge acquisition about hydrogen-bonding regions at protein surfaces" Proc. R. Soc. Lond. B, [1989], vol. 236, pp. 101-113.
Svend Aage Schou "Stability and Stabilization of Pharmaceutical Preparations" Pharmaceutica acta Helvetiae, [1959], vol. 34, No. 8/9, pp. 309-330.
Barry A. Edelman et al. "The Stability of Hypodermic Tablets of Nitroglycerin Packaged in Dispensing Containers" Journal of the American Pharmaceutical Association, NS11, [1971], pp. 30-33.
International Search Report from PCT/EP2014/076020 dated Feb. 23, 2015.
V.G.Granik, S.Yu. Ryabova, N.B. Grigoriev. Exogenic nitric oxide donors and inhibitors of its formation (the chemical aspects). Advances in chemistry, 66, 792 (1997).
Tian Fengwen et al "Medicine for Preventing and Treating Angina Pectoris—Nitroglycerin" May 11, 2008.
John T. Flaherty "Effect and mechanism of nitrate drag in chronic stable angina pectoris" Johns Hopkins Hospital, (1991), vol. 25, No. 1, pp. 91-110.
Medical Online "Therapeutic strategy of diastolic failure" Therapeutic Research, (2008), vol. 29, No. 7, pp. 1043-1059.
Pluta et al., "Safety and Feasibility of Long-term Intravenous Sodium Nitrite Infusion in Healthy Volunteers," PLoS One, Jan. 2011, vol. 6, Issue 1, pp. 1-13.
Davidov, M.E. & Mroczek, W.J. Effect of sustained release nitroglycerin capsules on anginal frequency and exercise capacity. Angiology 1977, 28: 181-189.
Winsor, T. & Berger, H.J. Oral nitroglycerin as a prophylactic antianginal drug: clinical, physiologic, and statistical of evidence efficacy based on a three-phase experimental design. Am Heart J 1975, 90: 611-626.
U.S. Appl. No. 13/904,228, filed May 29, 2013, Michaela Gorath.
U.S. Appl. No. 14/403,713, filed Nov. 25, 2014, Michaela Gorath.
U.S. Appl. No. 15/254,066, filed Sep. 1, 2016, Michaela Gorath.
U.S. Appl. No. 16/412,749, filed May 15, 2019, Michaela Gorath.
PCT/EP2013/061131, May 29, 2013, Michaela Gorath.
Anonymous, "Isosorbide mononitrate 40mg Tablets—(eMC)", Sep. 9, 2014 (https://www.medicines.org.uk/emc/print -document?documentId=25948).
Anonymous, "Imdur Tablets 60mg—(eMC)" May 26, 2015 (https://www.medicines.org.uk/emc/print -document?documentId=178).
Armstrong et al., "Blood Levels After Sublingual Nitroglycerin", Circulation, vol. 59, No. 3, Mar. 1979, pp. 585-588.
Armstrong et al., "Pharmacokinetic-Hemodynamic Studies of Intravenous Nitroglycerin in congestive Cardiac Failure", Circulation vol. 62, No. 1, Jan. 1980, pp. 160-166.
Buschmann et al., "The Pathophysiology of the Collateral Circulation (Arteriogenesis)", Journal of Pathology, vol. 190, 2000, pp. 338-342.
Chen et al., "Effect of acrylonitrile-butadiene rubber on nitroglycerin migration from propellant to EPDM inhibitor", Database Caplus [Online], Chemical Abstracts Service, Columbus, Ohio, US, (2004). retrieved from STN, Database accession No. 2004:826842, abstract.
Fox et al., Guidelines on the management of stable angina pectoris: full text. The Task Force on the Management of Stable Angina Pectoris of the European Society of Cardiology, European Heart Journal doi:10.1093/eurheartj/ehl002, 2006.
Gibbons et al., "ACC/AHA/ACP-ASIM Guidelines for the Management of Patients with Chronic Stable Angina", Journal of the American College of Cardiology, vol. 33, No. 7, 1999, pp. 2092-2197.
International Search Report and Written Opinion in related PCT Application No. PCT/EP2017/082932, dated Mar. 15, 2018 (11 pages).
McGrae McDermott, "The International Pandemic of Chronic Cardiovascular Disease", Journal of the American Medical Association, vol. 297, No. 11, 2007, pp. 1253-1255.
Uxa et al., "Standard versus Low-Dose Transdermal Nitroglycerin: Differential Effects on the Development of Tolerance and Abnormalities of Endothelial Function", Journal of Cardiovascular Pharmacology, vol. 56, No. 4, pp. 354-359. (Oct. 2010).
V&P Scientific, "Viscosity Tables", downloaded on Jun. 19, 2020 from "www.vp-scientific.com/Viscosity_Tables.htm", 3 pages. (2010).
Xylitol, Handbook of Pharmaceutical Excipients, Sixth Edition, Editors: Rowe et al., pp. 786-789. (2009).
Rote Liste 2004, Official Drug Registry of Germany, Rote Liste® Service GmbH, Frankfurt/Main. 3 pages.
Rote Liste 2004, Official Drug Registry of Germany, Chapter 55. Antianginals, Rote Liste® Service GmbH, Frankfurt/Main. 5 pages.

\* cited by examiner

10 DAYS RIP PBS:

10 DAYS SHAM PBS:

5 DAYS RIP PBS:

5 DAYS SHAM PBS:

5 DAYS SHAM NTG-PLACEBO:

5 DAYS SHAM NTG:

5 DAYS RIP NTG-PLACEBO:

5 DAYS RIP NTG:

5 DAYS RIP ISDN-PLACEBO:

5 DAYS RIP ISDN:

5 DAYS RIP ASA + PBS:

5 DAYS RIP ASA + NTG-PLACEBO:

5 DAYS RIP ASA + NTG:

INDUCTION OF ARTERIOGENESIS WITH AN NO (NITRIC OXIDE) DONOR

Cross Reference to Related Applications

This is a continuation of U.S. Patent Application No. 14/403,713 filed on Nov. 25, 2014, which is the national phase under 35 U.S.C. § 371 of International Application No. PCT/EP2013/061131 filed on May 29, 2013, which claims priority to and benefit of European Application No. 12004187.6 filed on May 31, 2012 and U.S. Serial No. 61/653,595 filed on May 31, 2012, the entire disclosures of each of which are incorporated by reference herein.

The present invention relates to methods of treating or preventing an arterial insufficiency by the administration of a NO (nitric oxide) donor.

Cardiovascular diseases as well as other diseases involving a cardiovascular and, more specifically, arterial insufficiency affect a rising patient population, head international mortality and morbidity statistics and have an enormous economic importance. In Germany, for example, about 280000 patients suffer every year from a cardiac infarct, while about 65000 patients die.

One important reason for a cardiovascular disease is the partial or complete occlusion of arterial vessels resulting in a reduced supply of oxygen and nutrients of the tissue supplied by the arterial vessel.

Angina pectoris, the chest pain, is a clinical syndrome reflecting inadequate oxygen supply for myocardial metabolic demands with resultant ischemia and is generally caused by obstruction (stenosis), spasm of coronary arteries, endothelial or microvascular dysfunction.

Arteriogenesis is a process in which already pre-existing small arteriolar collaterals can develop to full functional conductance arteries which bypass the site of an arterial occlusion and/or compensate blood flow to ischemic territories supplied by the insufficient artery. Consequently, arteriogenesis is a highly effective endogenous mechanism for the maintenance and regeneration of the blood flow after an acute or chronic occlusive event in an arterial vessel. In this case the collaterals can function as natural bypasses.

Arteriogenesis is a process distinct from angiogenesis or neovascularization, where a denovo formation of arterial vessels occur (Buschmann I. and Schaper W., Journal of Pathology, 2000, 190: 338-342).

Nitroglycerin (glyceryl trinitrate) is used since decades as a vasodilating agent in cardiovascular diseases as coronary artery disease (CAD, also ischemic heart disease or coronary artery disease), which is the leading cause of death and disability worldwide (McGrae McDermott M., Journal of the American Medical Association, 2007, 297 (11): 1253-1255). Nitroglycerin has been solely used to treat the symptoms of these diseases e.g. stable angina pectoris due to its vasodilating effect on veins and arteries, resulting in a reduced workload and energy consumption of the heart (by decreasing preload and afterload) as well as an increased myocardial oxygen supply (by dilating the coronary arteries). These symptoms include chest pain, pressure, discomfort, or dyspnea. However, nitroglycerin has not been used for curing the underlying disease or improving its prognosis.

Consequently, nitroglycerin has been and is primarily used for the acute relief or prophylaxis of angina pectoris attacks, the most common symptom of CAD (Fox K. et al., Guidelines on the management of stable angina pectoris: full text. The Task Force on the Management of Stable Angina Pectoris of the European Society of Cardiology. European Heart Journal doi:10.1093/eurheartj/eh1002; Gibbons R. J. et al., ACC/AHA/ACP-ASIM Guidelines for the Management of Patients With Chronic Stable Angina. Journal of the American College of Cardiology, 1999, 33 (7): 2092-2197).

In the art, it has been described that nitroglycerin is not able to induce angiogenesis (neovascularisation) or arteriogenesis in a setting where this substance has been administered continuously (Hopkins S. P. et al., Journal of Vascular Surgery, 1998, 27 (5): 886-894; Troidl K. et al., Journal of Cardiovascular Pharmacology, 2010, 55 (2): 153-160).

Long acting NO donors encompassing the group of diazeniumdiolates and diazeniumtriolates (also called NONOates) have been implicated in the induction and/or improvement of forming collaterals in the treatment of arterial diseases by means of continuous flow pump administration (Schaper W., DE 10 2008 005 484 A1).

There is a need for providing agents for promoting collateral circulation.

In a first aspect, the present invention relates to a method of treating or preventing an arterial insufficiency, wherein an NO donor is administered in an intermitting manner to a subject in an amount effective for the induction of arteriogenesis.

In the context of the present invention, it has been surprisingly found that NO donors are effective in the induction of arteriogenesis even if they are not administered constantly but in a manner where plasma levels are only elevated for a short time (see the example section). Consequently, the present invention provides effective agents for the promotion of collateral circulation. Based on the finding that NO donors are capable of inducing arteriogenesis, the present invention now provides an effective tool for preventing and treating an arterial insufficiency.

According to the present invention, the term "treatment" or "prevention" means that not only symptoms of the disease are relieved but that also the disease itself is treated or prevented. In a preferred embodiment, the term "treatment" means improving the prognosis of said disease.

According to the invention, the term "arterial insufficiency" refers to any insufficient blood or oxygen supply or any other insufficient supply of a tissue which is provided by an artery. This insufficient supply can be overcome by the methods and uses of the present invention wherein an NO donor is used to increase the supply of a given tissue. The arterial insufficiency may occur both during physical rest and during an exercise.

In a preferred embodiment of the present invention, the arterial insufficiency is due to insufficient oxygen or blood supply of a tissue supplied by the artery or a bypass or shunt during physical rest or exercise.

According to a further preferred embodiment, the arterial insufficiency is due to an increased demand of oxygen or blood flow of a tissue supplied by the artery or a bypass or shunt.

This increased demand of oxygen or blood flow can have several reasons including but not limited to increased sport or physical activity, and increased mental activity or a disease requiring an increased demand of oxygen or blood flow.

According to a further preferred embodiment, the arterial insufficiency is characterized by a partial (stenosis) or complete occlusion of an arterial vessel. In the context of the present invention, the term "partial occlusion" is equivalent to a stenosis.

The partial or complete occlusion of an arterial vessel is a well-known phenomenon. It can have various reasons including, but not limited to, deposition of material in the blood vessels (including non-revascularisable stenoses), compression from external tissue or fluid next to the vessel (including disturbance in diastolic myocardial relaxation), vascular spasm, dysfunction of the endothelium of the vessel resulting in a paradoxic vasoconstriction during exercise or microvascular impairment due to endothelial dysfunction or smooth muscle cell abnormalities.

In a preferred embodiment, the arterial insufficiency is due to the deposition of material in the blood vessels.

The deposition of materials in the blood vessels is a well-known phenomenon resulting e.g. in atherosclerosis.

In a further preferred embodiment, the arterial insufficiency is due to an external or internal compression of an artery.

An internal compression of an artery may be due to an edema but also to a tumor putting pressure on the artery. Furthermore, this includes a vasospastical constriction of the artery as e.g. in Prinzmetal's angina. In addition, this also includes the paradoxic vasoconstriction which e.g. sometimes occur in an endothelial dysfunction or constricted small arterial vessels due to endothelial or smooth muscle cell dysfunction.

An external compression may be due to an accident or any external force which can put pressure on an artery.

In a further preferred embodiment, the arterial insufficiency is a vascular disease.

According to a further preferred embodiment, the arterial insufficiency is a disease selected from the group consisting of atherosclerosis, an ischemic disease and a further chronic arterial disease.

In a further preferred embodiment, the arterial insufficiency is a coronary arterial insufficiency.

In a preferred embodiment, the coronary insufficiency is an atherosclerotic coronary arterial insufficiency, in particular coronary artery disease (coronary heart disease or ischemic heart disease), stable angina pectoris, unstable angina pectoris, myocardial ischemia or chronic myocardial ischemia, acute coronary syndrome, or myocardial infarct (heart attack or ischemic myocardial infarct).

In a further preferred embodiment, the coronary insufficiency is a non-atherosclerotic, in particular coronary microvascular disease or small vessel disease, Prinzmetal's angina and cardiac syndrome X.

Tn a further preferred embodiment, the arterial insufficiency is a cerebral arterial insufficiency (intra- or extracranial).

In a preferred embodiment, the cerebral arterial insufficiency is an atherosclerotic cerebral arterial insufficiency, in particular cerebral ischemia, extracranial carotid artery disease, extracranial vertebral artery disease, pre-stroke, transient ischemic attack (mini stroke), stroke, vascular dementia, ischemic brain disease, or ischemic cerebrovascular disease.

The cerebral arterial insufficiency may also be ischemic microvascular brain disease, small vessel vascular dementia, subcortical arteriosclerotic encephalopathy (Binswanger's disease), Alzheimer's disease, or Parkinson's disease.

In a preferred embodiment, the arterial insufficiency is a peripheral arterial insufficiency.

Tn a preferred embodiment, the peripheral arterial insufficiency is an atherosclerotic peripheral arterial insufficiency, in particular peripheral vascular disease (peripheral artery disease (PAD) or peripheral artery occlusive disease (PAOD), including lower and upper extremity arterial disease).

In a preferred embodiment, the peripheral arterial insufficiency is an non-atherosclerotic peripheral arterial insufficiency, in particular Raynaud's syndrome (vasospasmatic), thrombangiitis obliterans, endangitis obliterans or Buerger's disease (recurring progressive inflammation and thrombosis (clotting) of small and medium arteries and veins of the hands and feet), vascular inflammatory disease (vasculitis), diabetic ischemia, diabetic neuropathy and compartment syndromes.

In a further preferred embodiment, the arterial insufficiency may be an intestinal arterial insufficiency, in particular an atherosclerotic intestinal arterial insufficiency, in particular ischemic bowel disease, mesenteric ischemia, or mesenteric infarction.

In a further preferred embodiment, the arterial insufficiency may be an urogenital arterial insufficiency, in particular an atherosclerotic urogenital arterial insufficiency, in particular erectile dysfunction, renal artery disease, renal ischemia, or renal infarction.

In a further preferred embodiment, the arterial insufficiency may be a nerval arterial insufficiency, in particular tinnitus.

Furthermore, the arterial insufficiency may be in the context of scleroderma (systemic sclerosis).

Furthermore, the arterial insufficiency may be in the context of fibromuscular dysplasia.

In a preferred embodiment, the arterial insufficiency is a central retinal artery insufficiency, in particular an atherosclerotic central retinal artery insufficiency, in particular ocular arterial insufficiency.

In a further preferred embodiment, the arterial insufficiency is characterized by an absence of an endothelial dysfunction.

The endothelial dysfunction is a well-known systemic pathological state of the endothelium and can be broadly defined as an imbalance between vasodilating and vasoconstricting substances produced by or acting on the endothelium.

In a further preferred embodiment, the arterial insufficiency is a chronic arterial insufficiency. In the context of the present invention, the term "chronic arterial insufficiency" means that the course of the arterial insufficiency is chronic and often progredient.

According to a further preferred embodiment, the chronic arterial insufficiency includes endothelial dysfunction, atherosclerosis, coronary artery disease (coronary heart disease or ischemic heart disease), stable angina pectoris, coronary microvascular disease or small vessel disease, Prinzmetal's angina and cardiac syndrome X, vascular dementia, ischemic brain disease, or ischemic cerebrovascular disease, ischemic microvascular brain disease, small vessel vascular dementia, subcortical atherosclerotic encephalopathy (Binswanger's disease), Alzheimer's disease, Parkinson's disease, peripheral vascular disease (peripheral artery disease (PAD) or peripheral artery occlusive disease (PAOD), thrombangiitis obliterans, endangitis obliterans or Buerger's disease, vascular inflammatory disease (vasculitis), fibromuscular dysplasia, diabetic ischemia, diabetic neuropathy, ischemic bowel disease, erectile dysfunction, renal artery disease, tinnitus, and scleroderma (systemic sclerosis).

According to the invention, the term "NO donor" refers to either to nitric oxide itself or any molecule which is capable to release NO after having been administered to a subject.

Preferably, the NO donor is nitric oxide, sodium nitroprusside, nitroglycerin (glyceryl trinitrate), isosorbide mononitrate, isosorbide dinitrate, pentaerythritol tetranitrate (PETN), molsidomin, amyl nitrite or nicorandil.

In a preferred embodiment, the NO donors may be selected from the following:
Anorganic:
nitric oxide
nitrite
nitrate
Organic Nitrates:
GTN (glyceryl trinitrate; nitroglycerin)
PETN (pentaerythritol tetranitrate)
ISDN (isosorbide dinitrate)
ISMN (isosorbide mononitrate)
Nicorandil
Organic Nitrites:
IAN (isoamyl nitrite; amyl nitrite)
IBN (isobutyl nitrite)
N-nitroso compounds:
N-Nitrosamines:
Dephostatin
NDMA
derivates of N-methyl-N-nitrosourea
N-Hydroxy-Nitrosamines:
Dopastin
Cup ferron
Alanosine
N-Nitrosimines
N-Diazeniumdiolates (NONOate):
spermine NONOate
DEA-NONOate
DETA-NONOate
S-Nitrosothiols:
S-nitroso-N-acetylpenicillamine (SNAP)
S-nitrosoglutathione
Metal-NO-Complexes:
Iron complexes:
Nitroprusside (sodium nitroprusside)
Dinitrosyl-iron complexes
Iron-Sulfur Cluster Nitrosyls (as e.g. Roussin's Red Salt, Roussin's Black Salt, Roussin's Red Ester)
Ruthenium complexes
NO releasing Heterocycles:
Heterocyclic N-oxides:
Furoxans
Mesoionic Heterocycles:
Sydnonimines (as e.g. molsidomine, linsidomine (SIN-1), ciclosidomine, pirsidomine, marsidomine)
Mesoionic oxatriazoles
Guanidines and N-hydroxyguanidines:
L-arginine
L-homoarginine
N-hydroxy-L-arginine
N-hydroxy-L-homo arginine
Other:
Alkyl C-nitroso compounds
Aryl C-nitroso compounds
Oximes
N-hydroxyureas In a preferred embodiment, the NO donor is an organic nitrate with a glycerol backbone.

In a further preferred embodiment, the NO donor is selected from the group consisting of nitroglycerin (glyceryl trinitrate), glycerol-1,2-dinitrate (1,2-GDN) and glycerol-1,3-dinitrate (1,3-GDN), glycerol-1-nitrate (1-GMN) and glycerol-2-nitrate (2-GMN).

In a particular preferred embodiment, the NO donor is nitroglycerin.

Preferably, the NO donor is a short acting NO donor. According to the invention, the term "short acting NO donor" refers either to NO itself or to an NO donor which releases NO shortly, with a short half life time of less then e.g. 45, 30 or preferably 15 minutes, after having been administered to a subject. Examples of short acting NO donors are nitroglycerin (glyceryl trinitrate), amyl nitrite and sodium nitroprusside.

Short acting NO donors according to the present invention may also include NO donors which are generally regarded as long acting nitrate(s), but which may act as short acting nitrates dependent on their way of administration, dosage and formulation (standard release versus sustained-release or retard preparations). Such NO donors include, but are not limited to, the organic nitrate isosorbide dinitrate (ISDN) which has a variable half-life of between 15 to 35 up to 60 minutes when administered bucally or sublingually, for example, in form of a spray, or as a tablet. The half-life after oral administration is about 30 to 60 minutes at low doses or increases to several hours in the case of retard or sustained-release preparations.

Accordingly, a "short acting NO donor" according to the present invention also refers to an NO donor which releases NO with a half-life time of 60 minutes or less after having been administered to a subject in a particular way of administration, preferably when having been administered to a subject bucally or sublingually.

In the context of the present invention, it has surprisingly been found that the administration of a short acting NO donor is particularly suitable for promoting collateral circulation. This might be explained by the short-term dilatation of the collateral vessel induced by short acting NO donors which, in turn, has a significantly improved effect on arteriogenesis when repetitively applied. The improved effect of short NO donors on the formation of new collateral vessels and, thereby, on the promotion of collateral circulation is exemplified in detail in Example 1 of the present application.

Accordingly, in a preferred embodiment of the invention, the NO donor is a short acting donor.

Nitroglycerin is an especially preferred example of such a short acting NO donor.

According to the invention, the NO donor is administered in an amount capable of inducing arteriogenesis. The skilled person will appreciate that this amount will depend on the subject to which the NO donor is administered. Generally, the amount to be administered may be between 0.1 and 8 mg per day, but this can vary due to the weight of the subject, its hemodynamic response to the NO donor and/or the severity of the disease.

The amount of NO donor to be administered may also be between 0.1 and 10 mg per day, or, alternatively, between 0.1 and 40 mg per day, dependent on the nature of the NO donor and/or its way of administration. That is, if the NO donor is, for example, in form of organic nitrate isosorbide dinitrate (ISDN), the amount to be administered may be between 1 and 40 mg per day, preferably 5, 10, 15, 20, 25, 30, 35, or 40 mg per day when administered to a subject bucally or sublingually.

Accordingly, isosorbide dinitrate (ISDN) is an equally preferred example of such a short acting NO donor.

In a preferred embodiment, the amount of the NO donor is applied in a dosage of 0.2 up to 0.8 mg (0.2, 0.3, 0.4, 0.6, 0.8) for at least 1- up to maximal 4-times daily, resulting in a maximal daily dosage of 3.2 mg. These numbers especially apply in cases where the NO donor is nitroglycerin.

According to the invention, the term "administration of an NO donor" means that a given dosage of the NO donor is administered. Depending on the way of administration, the skilled person will appreciate that the administration may take some time. In a preferred embodiment, the NO donor is administered in form of a spray, sprayable or injectable solution, chewable capsule, inhalable gas, inhalable aerosol or powder, granules, powder or a tablet, preferably a sublingual, buccal or chewable tablet, which means that the administration may be completed within seconds. However, the administration of the NO donor may also take longer, e.g. if the NO donor is administered to the patient by way of infusion or by ointment or gel or patch. Modes of administration of the NO donor are further discussed below.

Furthermore, according to the invention, the NO donor is administered in a manner capable of inducing arteriogenesis.

As shown in the examples, the inventors of the present invention have surprisingly found out that an NO donor is capable of inducing arteriogenesis when administered in an intermitting manner.

According to the invention, the term "intermitting manner" means that the NO donor is administered in a way that its plasma or tissue levels are only elevated in a short-term manner after the administration of the NO donor but then again decline. This can be achieved for example if the NO donor is a short acting NO donor as defined above and the administration of the short acting NO donor is followed by a time period without administration and then the NO donor is again administered to the subject. Furthermore, this way of administration avoids that the subject is developing tolerances against the NO donor and that the subject is developing endothelial dysfunction.

The induction of endothelial dysfunction is a parameter which has a prognostic significance in patients with coronary artery disease. The development of tolerances as well as the induction of endothelial dysfunction are well known disadvantages caused by the sustained, long term exposure to NO donors (Uxa A. et al., Journal of Cardiovascular Pharmacology, 2010, 56 (4): 354-359).

Moreover, the administration of a short acting NO donor in an intermitting manner has the improved effect that it mimics the physiological situation of the organism as, for example, comparable to the endogenous release of NO upon physical training. In other words, the NO donor of the present invention acts as a biomimetic when applied in an intermitting manner. This clearly represents an improvement over the art where the induction of arteriogenesis has so far only been observed upon administering long acting NO donors by means of continuous, and thereby non-intermitting, administration.

Accordingly, in a particularly preferred embodiment, the NO donor is a short acting NO donor which is administered in an intermitting manner.

However, it is equally possible that the NO donor is a long acting NO donor. In this case, however, in order to achieve the decline in plasma or in tissue levels, care has to be taken that the administration of the long acting NO donor is only shortly and that the plasma or tissue levels obtained are not too high.

In a preferred embodiment, the plasma or tissue levels of the NO donor are elevated for not more that 180, 120, or 60 minutes, or for not more than 50, 40, 30, 15, 10 or 5 minutes.

Furthermore, this also implies that the NO donor can be administered in chronical manner, i.e. without taking account of disease developments implying an acute treatment with the NO donor. Furthermore, it also implies that a therapy plan can be established without taking account of disease developments implying an acute treatment with the NO donor.

In the context of the present invention, the NO donor is inter alia administered to induce arteriogenesis. This implies that the NO donor can also be administered at time points or time periods where there is no need for vasodilation and such a relief of symptoms like pain relief.

This is in contrast to past applications where the NO donor, e.g. nitroglycerin, has been used to achieve a relief or acute (i.e. immediate) prevention of the symptoms of a corresponding disease. These symptoms for example include pain and/or dyspnea in the case of a cardiovascular disease, and the relief or acute prevention of the symptoms was achieved by vasodilation and resulting pain and/or dyspnea relief. However, the purpose of the administration of the NO donor was, as discussed above, not the treatment of the underlying disease, because it was well known that the diseases cannot be treated by vasodilation or pain relief.

The identification of an NO donor as a pro-arteriogenic agent, therefore, also makes it possible that the NO donor is administered at time points or time periods where there is no need for such a relief of symptoms like pain relief. In a further preferred embodiment, the NO donor can also be administered in cases where there are no corresponding symptoms like dyspnea or pain or in cases where such symptoms are not to be expected.

In the context of the present invention, the term "intermittently" also means that the NO donor, in particular the short acting NO donor, is not administered continuously, for example by means of long term intravenous infusion or with the help of an implanted pump which constantly delivers the NO donor to the subject. Rather, this term also means that there is an interval between two administrations of the NO donor, and that the NO donor is given several times, e.g. at least 1, 2, 3, 4, 5, 6, 8, 9, 12 or 16 times a day.

As the skilled person will appreciate, one administration of the NO donor may include an administration in one or more dosage forms, e.g. tablets or hubs (puffs) in case of a spray. For example, one administration may include the administration of two tablets or one to three hubs (puffs).

As to the schedule of administration, the skilled person will appreciate that there are many ways to achieve this intermitting administration. For example, it is possible to administer the NO donor at least once a day and at least on one day a week for at least two weeks. However, it is equally possible to administer the NO donor for only one week if the NO donor is administered several times during this week.

Preferable, the NO donor is administered once, twice or three times a day, wherein even more preferred the time period between two administrations of the NO donor is at least 4 hours, in particular 8 hours, in particular at least 10 hours or 12 hours.

Although possible, it is not necessary that the time periods between two administrations of the NO donor are the same. Rather, it is preferred that these time periods differ, depending on the individual administration schedule.

In a preferred embodiment, the NO donor is administered at least on one day a week. However, the NO donor may also be administered on 2, 3, 4, 5, 6 or 7 days a week. In an especially preferred embodiment, the NO donor is administered at least on 3 or 4 days a week.

According to the invention, it is possible to administer the NO donor for a period of several weeks or months. This is particularly preferred in order to induce arteriogenesis efficiently, although also a shorter administration of one of two weeks is possible.

In a preferred embodiment, the NO donor is administered for 2 to 8 weeks. It is equally preferred to administer the NO donor for 3 to 6, 3 to 8, 3 to 10 or 4 to 8, 4 to 10 or 4 to 12 weeks. These numbers are only examples and may vary depending on the individual schedule of the subject.

In a preferred embodiment, the NO donor is taken at least once a week for at least 8 weeks, in particular for at least 12 weeks.

In a further preferred embodiment, the NO donor is taken not longer than 6, 8 or 12 months. However, it is also possible to take the NO donor for 2, 3 or even more years. Furthermore, it is also possible that the NO donor is administered for decades or even through the whole life of the subject.

In the context of such long-term administrations, it is preferred that the NO donor is administered once or twice a week or at least once or twice a week.

It has been described previously that an exogenous stimulation of pulsatile shear forces in an individual may result in arteriogenesis. Furthermore, it has been described how the pulsatile shear forces can be measured (WO 2010/072416).

Consequently, in a preferred embodiment, the NO donor is administered in conjunction with an exogenous stimulation of the pulsatile shear forces in the artery.

With respect to said embodiment of the invention, the NO donor should be administered in a way that it is active in the body of the subject when the exogenous stimulation is applied.

In this context, active means that either the NO release is not yet terminated or the NO released from the NO donor is still present and active. Depending on the specific NO donor to be used, its physiological halftime in the subject and its formulation, the skilled person will be capable of determining when the NO donor has to be administered to the subject in order to ensure that it is active upon the exogenous stimulation.

In the case of nitroglycerin, the halftime and its persistence in the body of the subject has been intensively studied, e.g. after intravenous or sublingual application, where it is 2 to 5 minutes in the blood plasma, see e.g. Armstrong P. W. et al., Circulation, 1979, 59: 585-588 or Armstrong P. W. et al., Circulation, 1980, 62:160-166.

In general, the halftime of nitroglycerin in the blood plasma is 2 to 5 minutes.

It is to be understood that, in the context of the present invention, the term "halftime" refers to the half-life and/or to the half-life time of the NO donor in the subject's body, in particular in the subject's blood plasma.

In a preferred embodiment, the NO donor is administered in the time period of 30 minutes before the onset of the exogenous stimulation until 30 minutes after the termination of the exogenous stimulation.

More preferably, the NO donor is administered in the time period of 15 minutes, preferably 5 minutes, more preferably 2 minutes before the exogenous stimulation until 30, preferably 15, more preferably 5 minutes after the onset of the exogenous stimulation.

In a further preferred embodiment, the NO donor is administered once a day, five times a week for 6 weeks 2-5 minutes before the exogenous stimulation.

The exogenous stimulation of the pulsatile shear forces may be achieved by any known way. This includes an stimulation with the help of medicaments like medicaments which increase the blood pressure.

In a preferred embodiment, said stimulation is achieved by physical exercise or the application of an endogenous force to the arterial vessel.

According to the invention, the term "physical exercise" means any training of the subject, including but not limited to training in exercise rooms, jogging, walking, nordic walking, swimming, dancing, cycling and hiking The skilled person will appreciate that any exercise will be helpful in the context of the invention, provided that it is performed in conjunction with the administration of the NO donor. Preferably, the term "physical exercise" does not include unsupervised, unprescribed routine movements like casual walking or house work.

As discussed above, it has been found in the context of the present invention that an NO donor is capable of inducing arteriogenesis. This enables not only the treatment of an already existing disease. Rather, in the context of the present invention, it is also possible to prevent the disease. Consequently, in a preferred embodiment of the present invention, the method aims at the prevention of said arterial insufficiency.

As shown in the example section, in the context of the present invention, it has been possible to reduce the infarct size in case of an already existing occlusion. Furthermore, it has been possible to reduce arrhythmias in the subjects. Consequently, in a preferred embodiment of the present invention, the method results in a reduction of the infarct size, in reduced arrhythmias or in a decreased ST segment elevation.

The NO donor can be administered in any suitable way so that it can be incorporated into the subject. This includes an oral, parenteral or intravenous administration as well as the injection of the NO donor into the body of the subject, but also an administration to a mucous membrane of the subject.

Consequently, in a preferred embodiment of the present invention, the NO donor is administered lingually, sublingually, inhalatively, bucally, transmucosally or oromucosally.

In case of a lingual, sublingual or oromucosal administration, it is preferred that the NO donor, preferably nitroglycerin, is administered with the help of a spray, sprayable or injectable solution, a chewable capsule or in the form of a tablet, preferably a sublingual, buccal or chewable tablet, powder or granules or even by an inhalator device, from which the NO donor can be easily inhaled and adsorbed. It is equally preferred that the NO donor is administered in the form of an inhalable gas, aerosol or powder.

Preferably, the administration of the NO donor is a non-topical administration, i.e., that the NO donor is not administered to the skin of the subject. In the context of the present invention, the term "skin" excludes mucous membranes of the subject.

The NO donor can be formulated in any suitable way for the above mentioned administration modes. Such formulations are known to the person skilled in the art and include the formulation in suitable buffers, in a gas, aerosol, as tablets, powder or granules.

In a preferred embodiment, the NO donor is formulated in a way that allows a fast release of the NO donor from the formulation. This includes e.g. formulations which do not hold back the NO donor for a longer time period, but which release the NO donor within e.g. 45, 30 or 15, 10, 5 minutes or 1 minute.

Through the invention, it is preferred that the subject to which the NO donor is applied is a human subject.

In a further aspect, the present invention also relates to an NO donor for use in a method for the prevention or treatment of an arterial insufficiency, wherein the NO donor is administered in an amount and manner effective for the induction of arteriogenesis.

All features and preferred embodiments discussed above for the method of treating or preventing an arterial insufficiency also apply to the NO donor for use according to this aspect of the invention.

In another aspect, the present invention also relates to a method of the suppression of negative effects associated with any treatment of an arterial insufficiency which is anti-ateriogenic or inhibiting arteriogenesis, comprising administering to a subject subjected to said treatment an NO donor in an amount and manner effective for the induction of arteriogenesis.

In a preferred embodiment, said treatment is an acetyl salicylic acid (ASA), glycoproteinIIbIIIa antagonists, or etanercept (soluble tumor necrosis factor alpha receptor) treatment.

It is known in the art that ASA is an inhibitor of arteriogenesis (Singer E. et al., Vasa, 2006, 35 (3): 174-177). Consequently, the ASA treatment of cardiovascular diseases, although being a standard therapy, has significant side effects and disadvantages. In the context of the present invention, it has been found that NO donors are capable of overcoming the genitive effects associated with an ASA treatment (see example section). Based on these findings, the inventors conclude that also the negative side effects associated with other medications like glycoproteinIIbIIIa antagonists or etanercept treatment can also be diminished.

Furthermore, the present invention also relates to an NO donor for use in a method of the suppression of negative effects associated with any treatment of an arterial insufficiency which is anti-arteriogenic or inhibiting arteriogenesis, wherein the NO donor is administered to a subject subjected to said treatment in an amount and manner effective for the induction of arteriogenesis.

In a preferred embodiment, said treatment is an acetyl salicylic acid (ASA), glycoproteinIIbIIIa antagonists, or etanercept (soluble tumor necrosis factor alpha receptor) treatment.

All features and preferred embodiments discussed above for the method of treating or preventing an arterial insufficiency also apply to the method for the suppression of negative effects according to this aspect of the invention or to said NO donor for use according to this aspect of the invention.

In a further aspect, the present invention also relates to a method for the prevention or treatment of a cardiac arrhythmia, wherein an NO donor is administered to a subject in an amount and manner effective for the treatment of said cardiac arrhythmia. Furthermore, the present invention also relates to an NO donor for use in a method for the prevention or treatment of a cardiac arrhythmia, wherein the NO donor is administered to a subject in an amount and manner effective for the treatment of said cardiac arrhythmia.

In the context of the present invention, the inventors have found that NO donors are capable to prevent and treat arrhythmias (see the example section).

All features and embodiments defined above with respect to the NO donor and its formulation and administration also apply to this method or NO or donor for use according to the invention.

The present invention also relates to a method of promoting collateral circulation comprising the step of exposing a subject to a therapeutically effective amount of an NO donor wherein the therapeutically effective amount of the NO donor promotes arteriogenesis sufficient to augment collateral circulation in a physiological or pathological condition.

The term collateral circulation describes the circulation of blood through so-called collateral vessels. These vessels are small arterioles, which are part of a network that interconnects perfusion territories of arterial branches. In the case that the main artery itself is not capable of sufficiently supplying a tissue, e.g. due to an arterial occlusion, these collateral vessels are recruited and can develop to large conductance arteries, to bypass the site of an arterial occlusion and/or to compensate blood flow to ischemic territories supplied by the or insufficient artery. In the context of the present invention, the promotion of collateral circulation occurs via arteriogenesis.

According to the invention, the term "physiological condition" denotes any condition of the subject which is not related to any disease.

According to the invention, the term "pathological condition" denotes any condition of the subject which is related to a disease.

Preferably, the subject suffers from an arterial insufficiency.

All features and preferred embodiments discussed above for the method of treating or preventing an arterial insufficiency also apply to the method of promoting collateral circulation.

With respect to the aspects defined above where the NO donor is administered in a manner sufficient to induce arteriogenesis this manner is preferably an intermitting manner as defined above.

The invention is further described by the attached figures and examples, which are intended to illustrate, but not to limit the invention.

SHORT DESCRIPTION OF THE FIGURES

FIG. 1: Course of the ST segment elevation per beat after FPO (=final occlusion to induce infarct) of 5- and 10-days-control-groups. ECG graph in middle grey indicates 5 DAYS RIP PBS, n=8: 0.104±0.016 mV; ECG graph in black indicates 5 DAYS SHAM PBS, n=8: 0.134±0.034 mV; ECG graph in light grey indicates 10 DAYS RIP PBS, n=7: 0.055±0.033 mV; ECG graph in dark grey indicates 10 DAYS SHAM PBS, n=7: 0.124±0.039 mV.

ECG was recorded 90 minutes after FPO. Course of the ST segment elevation per beat at first 1200 beats revealed no differences between 5- and 10-days-sham-groups and 5-days-RIP-group. Only in the 10-days-RIP-group a lower ST segment elevation was observed.

Figure 2:
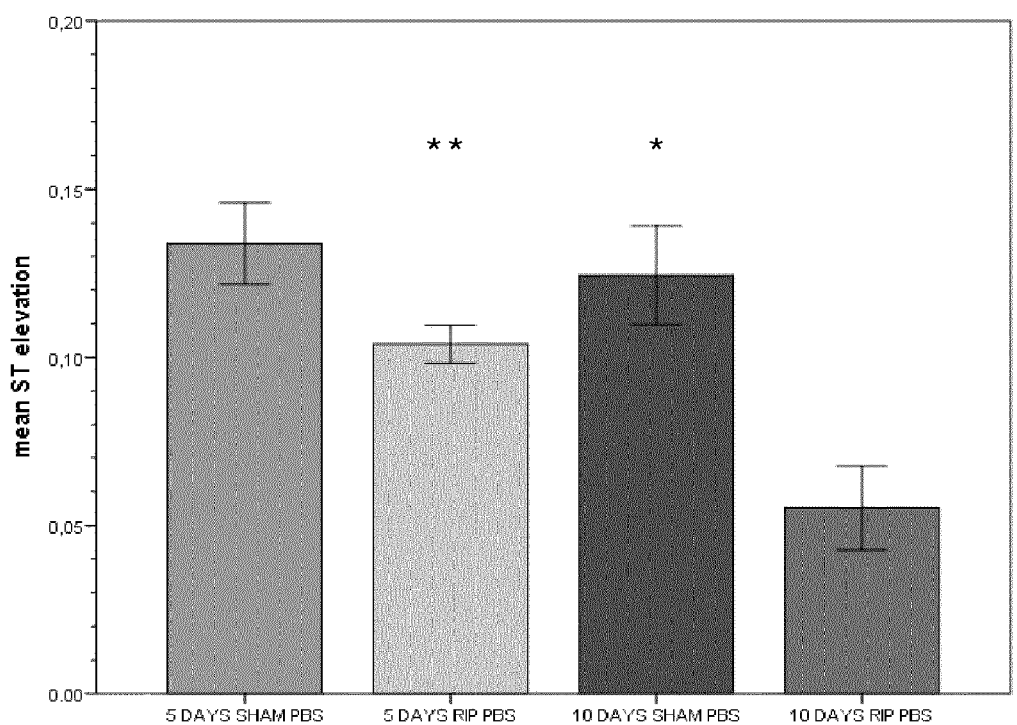

FIG. 2: ST segment elevation of 5- and 10-days-control-groups. Column 1 shows ST segment elevation of 5 DAYS SHAM PBS group; column 2 shows ST segment elevation of 5 DAYS RIP PBS group; column 3 shows ST segment elevation of 10 DAYS SHAM PBS group; column 4 shows ST segment elevation of 10 DAYS RIP PBS group; standard deviation is indicated in error bars; asterisk indicates significant compared to 10 DAYS SHAM PBS (nominal p value<0.025); double asterisk indicates significant compared to 5 DAYS RIP PBS (nominal p value<0.025).

Diagram shows mean of ST segment elevation maximum per group. After 5 days there was no significant difference found between RIP and SHAM. After 10 days in the RIP group ST segment elevation maximum was significantly lower compared to sham (*) and 5-day RIP control (**) (*, ** nominal p-value<0.025).

Figure 3:
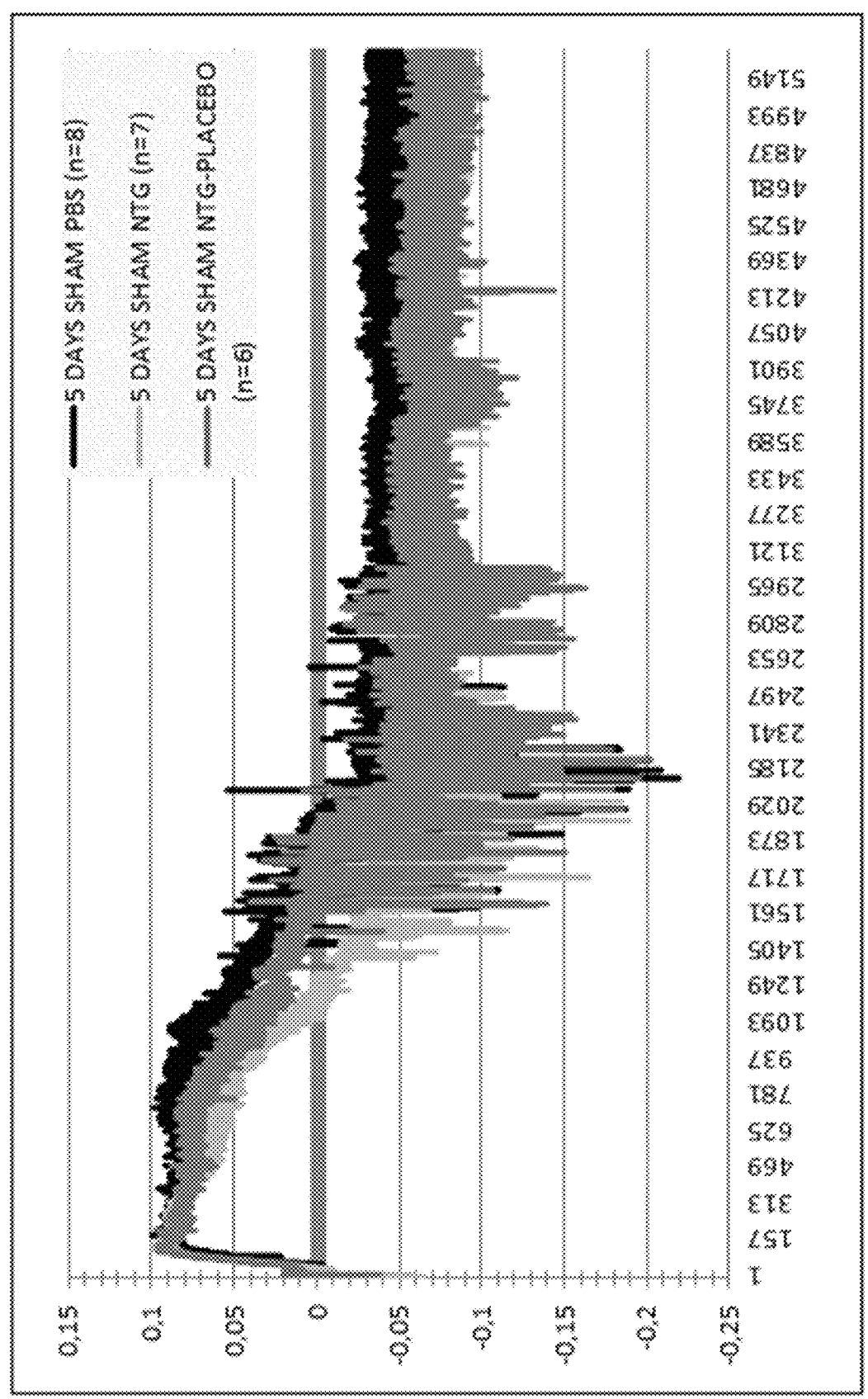

FIG. 3: Course of the ST segment elevation per beat after FPO (module 1: Sham operation without the RIP). ECG graph in black indicates 5 DAYS SHAM PBS, n=8: 0.134±0.034 mV; ECG graph in light grey indicates 5 DAYS SHAM NTG, n=7: 0.124±0.058 mV; ECG graph in middle grey indicates 5 DAYS SHAM NTG-PLACEBO, n=6: 0.131±0.043 mV.

The course of the ST segment elevation per beat after FPO revealed no differences between sham control and treated groups after 5 days.

Figure 4:
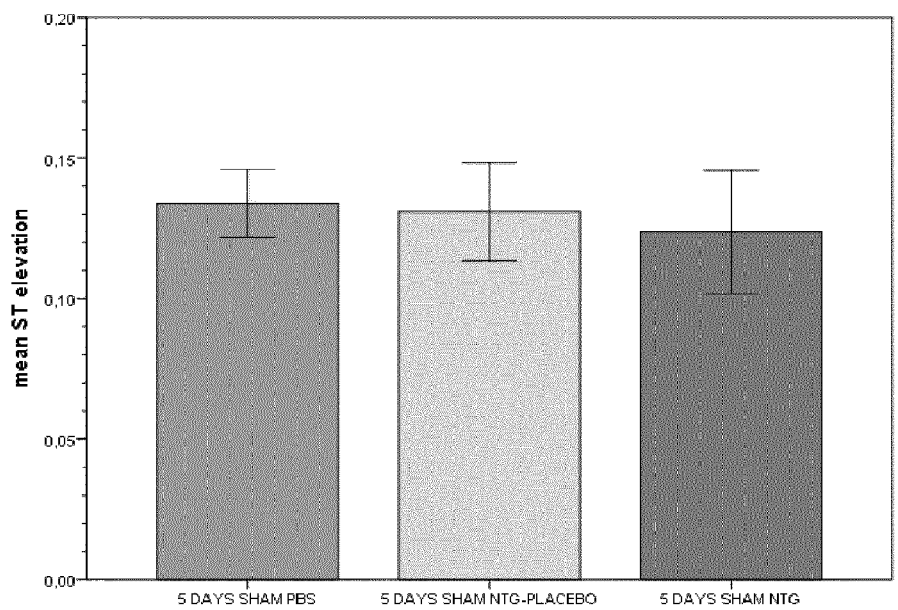

FIG. 4: ST segment elevation (module 1: Sham operation without the RIP). Column 1 shows 5 DAYS SHAM PBS; column 2 shows 5 DAYS SHAM NTG-Placebo; column 3 shows 5 DAYS SHAM NTG; standard deviation is indicated by error bars.

Diagram shows mean of ST segment elevation maximum per group. No difference in ST segment elevation maximum was found between sham control and treated groups.

Figure 5:
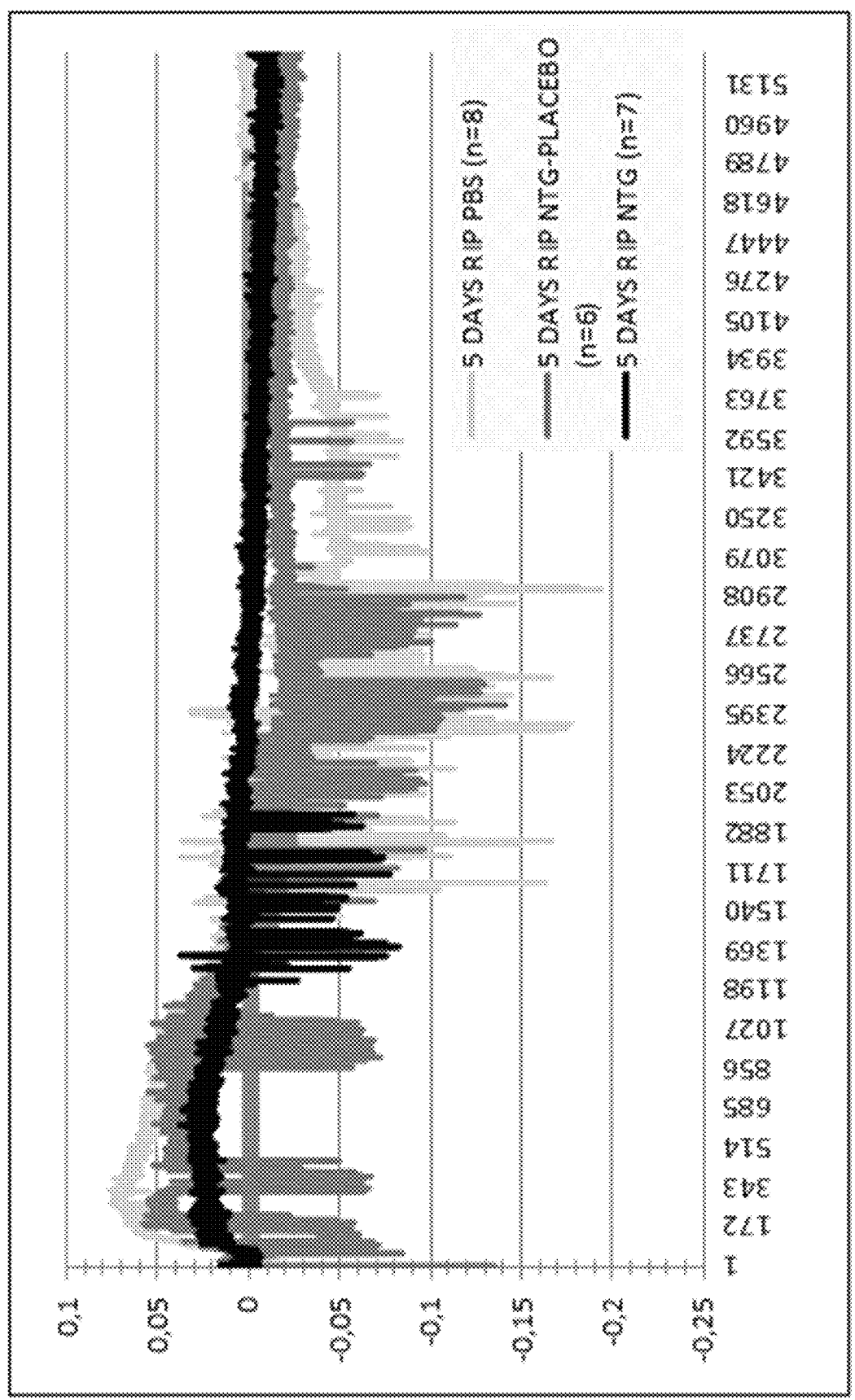

FIG. 5: Course of the ST segment elevation per beat after FPO (module 2: NO intermittent (NTG)). ECG graph in light grey indicates 5 DAYS RIP PBS, n=8: $0.104\pm0.016$ mV; ECG graph in middle grey indicates 5 DAYS NTG-PLACEBO, n=6; $0.096\pm0.061$ mV; ECG graph in black indicates 5 DAYS RIP NTG, n=7: $0.052\pm0.030$ mV. Compared to control treatment with PBS or NTG-Placebo a lower ST segment elevation course was detected after NTG treatment 5 days after RIP.

In the NTG group ("5 DAYS RIP NTG") ST segment elevation is significantly decreased compared to the PBS and NTG-Placebo group. There is no significance between the PBS and NTG-PLACEBO-group.

Figure 6:
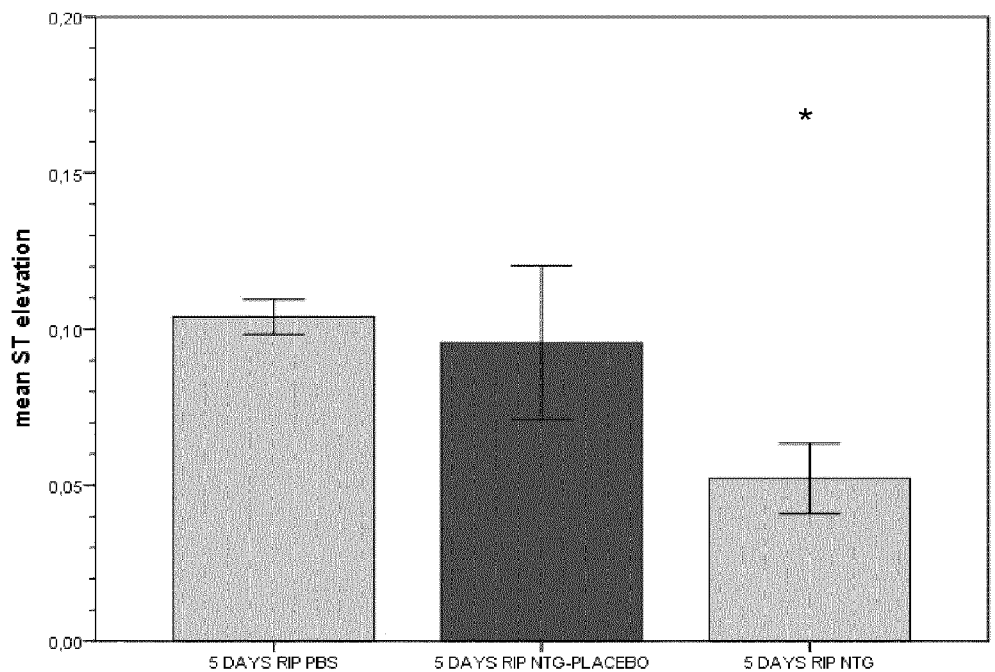

FIG. 6: ST segment elevation (module 2: NO intermittent (NTG)). Column 1 shows 5 DAYS RIP PBS; column 2 shows 5 DAYS NTG-PLACEBO; column 3 shows 5 DAYS RIP NTG; standard deviation is indicated by error bars, asterisk indicates significant decrease of ST segment elevation compared to PBS and NTG-Placebo group (nominal p-value<0.017).

Diagram shows mean of ST segment elevation maximum per group. After treatment with NTG, the ST segment elevation maximum was significantly decreased compared to PBS and NTG-Placebo treatment 5 days after RIP (*nominal p-value<0.017).

Figure 7:
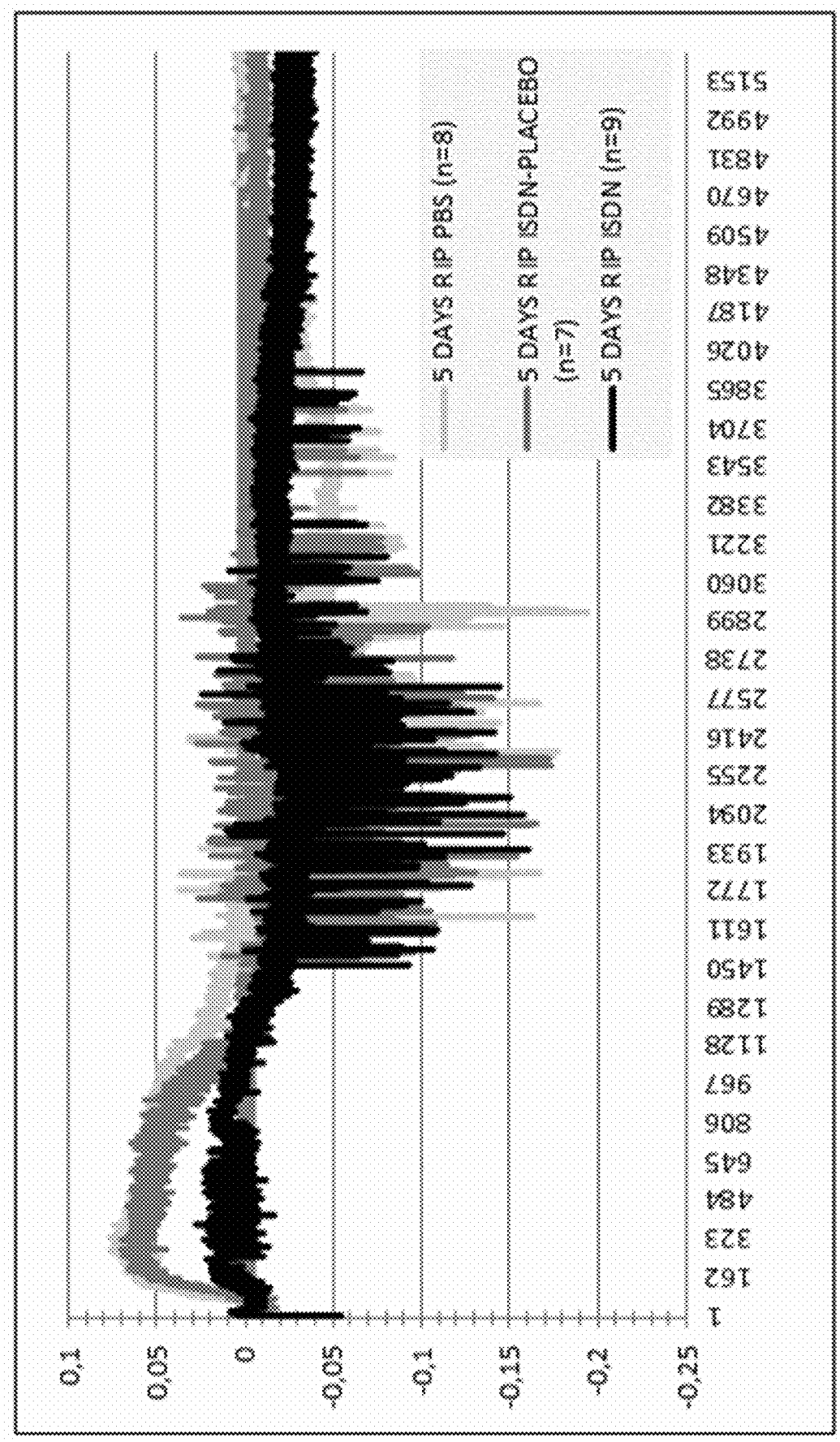

FIG. 7: Course of the ST segment elevation per beat after FPO (module 3: NO continuous (ISDN retard)). ECG graph in light grey indicates 5 DAYS RIP PBS, n=8: $0.104\pm0.016$ mV; ECG graph in middle grey indicates 5 DAYS ISDN-PLACEBO, n=7: $0.110\pm0.069$ mV; ECG graph in black indicates 5 DAYS RIP ISDN, n=7: $0.062\pm0.027$ mV.

Compared to control treatment with PBS or ISDN-Placebo a lower ST segment elevation course was detected after ISDN treatment 5 days after RIP.

ST segment elevation in the ISDN group ("5 DAYS RIP ISDN") is decreased compared to the PBS group but there is no significance as well as between the PBS and ISDN-PLACEBO-group.

Figure 8:
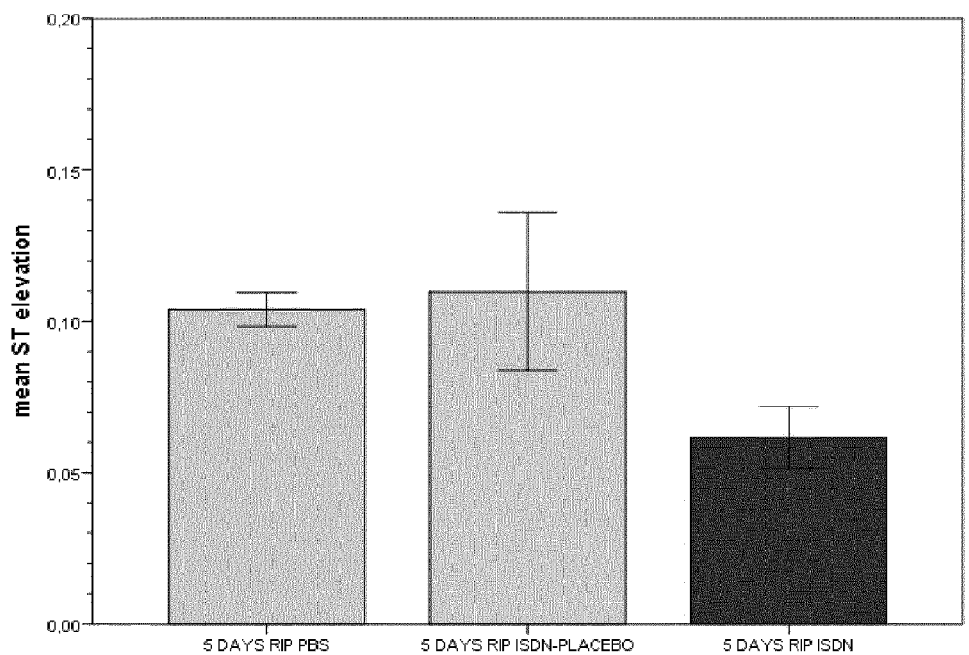

FIG. 8: ST segment elevation (module 3: NO continuous (ISDN retard)). Column 1 shows 5 DAYS RIP PBS; column 2 shows 5 DAYS RIP ISDN-PLACEBO; column 3 shows 5 DAYS RIP ISDN; standard deviation is indicated by error bars.

Diagram shows mean of ST segment elevation maximum per group. After treatment with ISDN, the ST segment elevation maximum was non-significantly decreased compared to PBS and ISDN-Placebo treatment 5 days after RIP.

Figure 9:
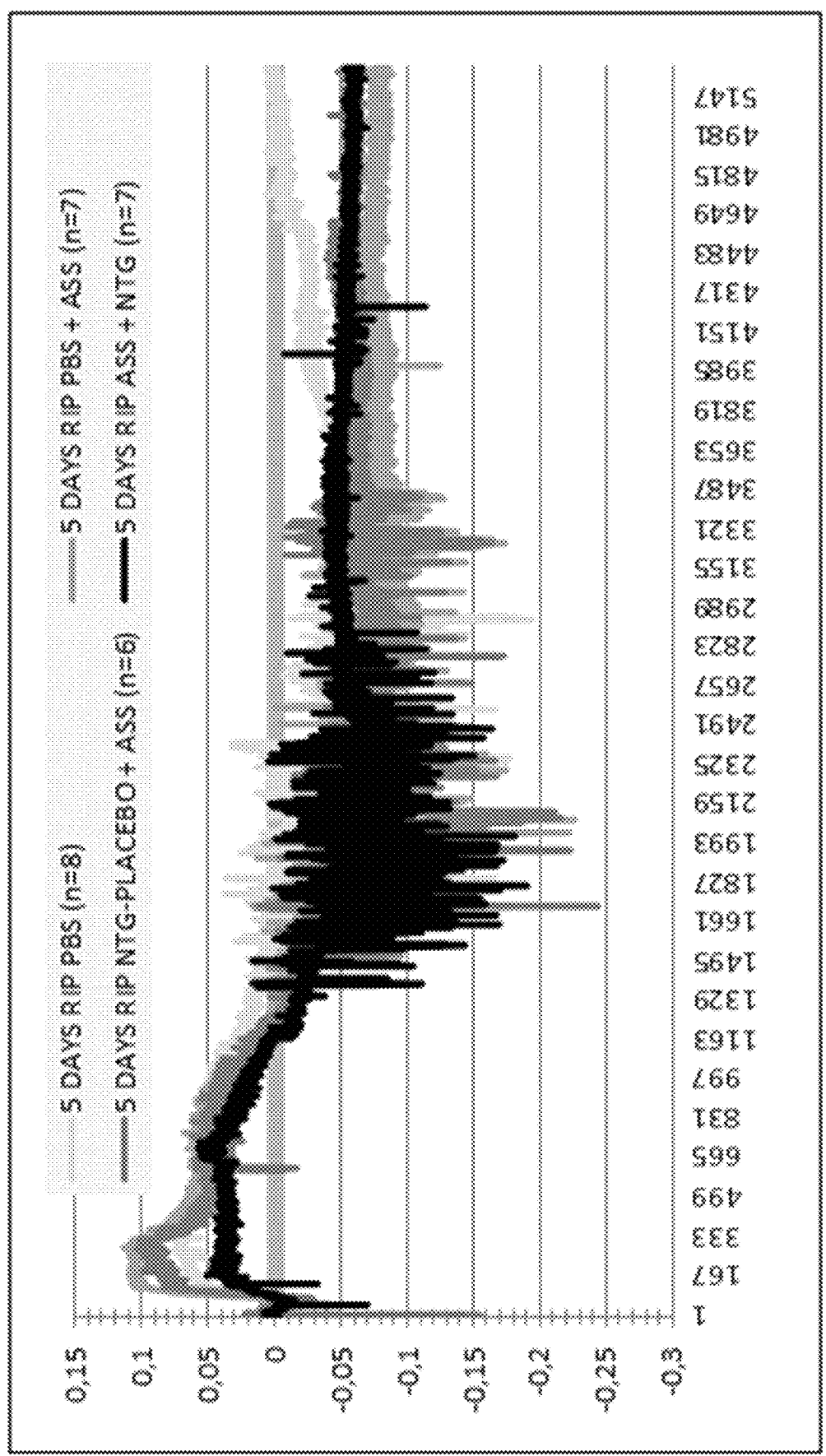

FIG. 9: Course of the ST segment elevation per beat after FPO (module 4: NO intermittent plus ASA). ECG graph in light grey indicates 5 DAYS RIP PBS, n=8; $0.104\pm0.016$ mV; ECG graph in middle grey indicates 5 DAYS RIP ASA+PBS, n=7: $0.138\pm0.098$ mV; ECG graph in dark grey indicates 5 DAYS RIP ASA+NTG-PLACEBO, n=6: $0.144\pm0.091$ mV; ECG graph in black indicates 5 DAYS RIP NTG+ASA, n=7: $0.088\pm0.071$ mV.

Treatment with NTG+ASA was compared to with PBS+ASA, NTG-Placebo+ASA and PBS. In general, all curves overlay at the same range.

ST segment elevation in the group treated with PBS and ASA is higher compared to the PBS control group, but there is no significance as well as between the ASA+NTG-PLACEBO-group. In the ASA+NTG-group ST segment elevation is decreased compared to the group treated with ASA and PBS.

Figure 10:
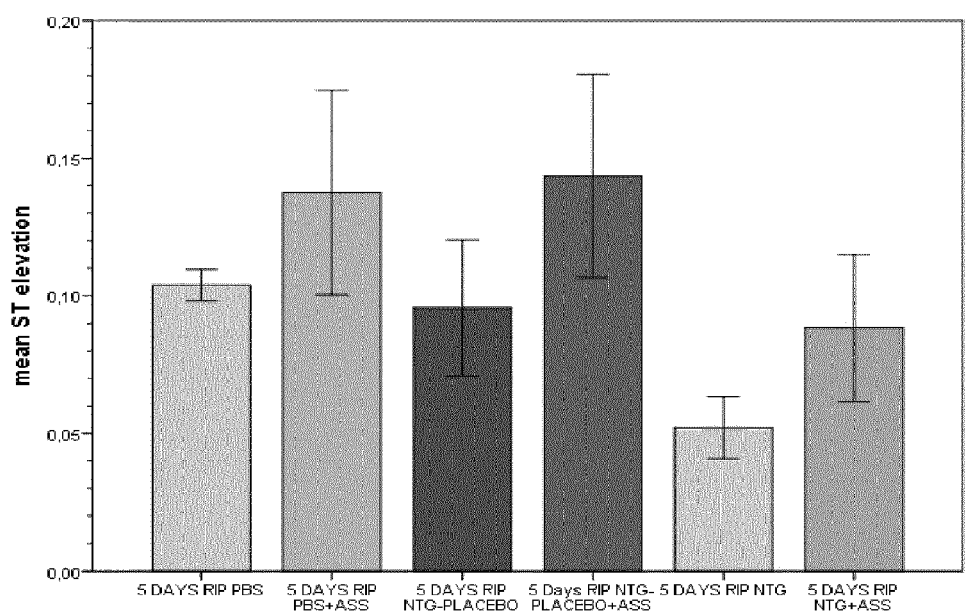

FIG. 10: ST segment elevation (module 4: NO intermittent plus ASA). Column 1 shows 5 DAYS RIP PBS; column 2 shows 5 DAYS RIP PBS+ASA; column 3 shows 5 DAYS RIP NTG-PLACEBO; column 4 shows 5 DAYS RIP NTG-PLACEBO+ASA; column 5 shows 5 DAYS RIP NTG; column 6 shows 5 DAYS RIP NTG+ASA; standard deviation is indicated by error bars.

Diagram shows mean of ST segment elevation maximum per group. Treatment with NTG+ASA was compared to PBS+ASA, NTG-Placebo+ASA and PBS. Furthermore, all ASA groups (PBS+ASA, NTG-Placebo+ASA, NTG+ASA) were compared to their controls (PBS, NTG-Placebo, NTG). No significant differences were detected.

Figure 11:
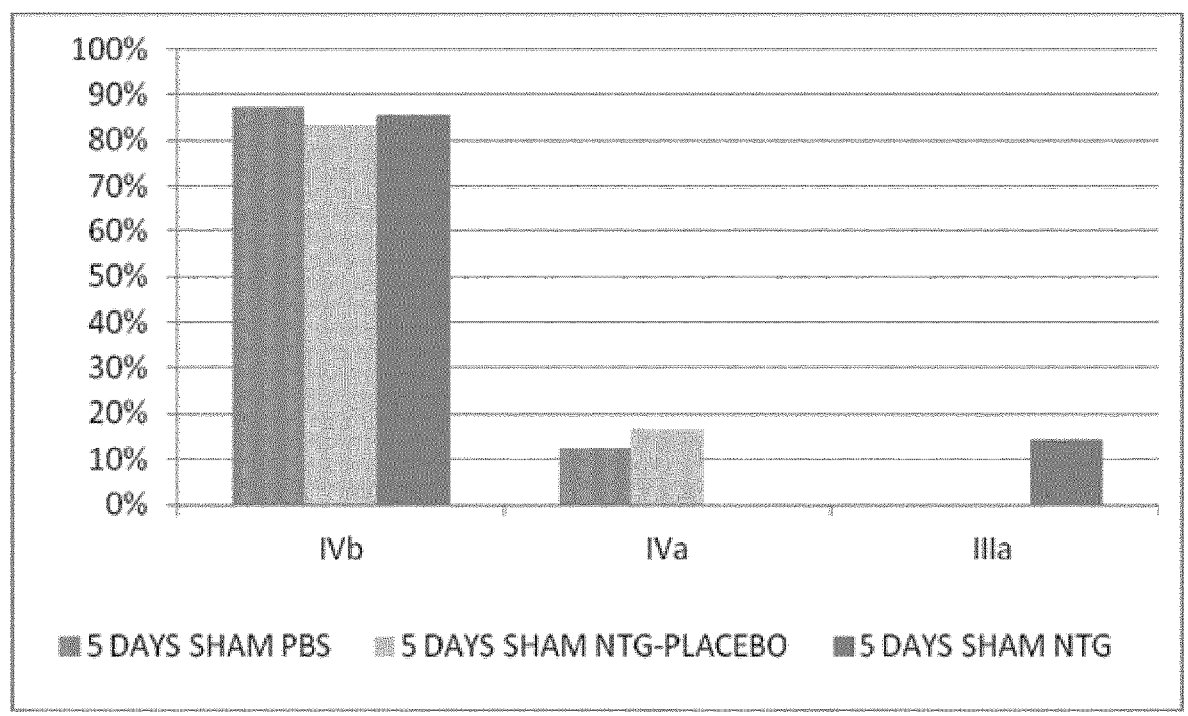

FIG. 11: Arrhythmias during FPO (module 1: Sham Operation (without the RIP)). Numbers of columns are given in consecutive order of the columns in group IVb. Column 1 shows 5 DAYS SHAM PBS; column 2 shows 5 DAYS SHAM NTG-PLACEBO; column 3 shows 5 DAYS SHAM NTG.

In accordance with Lown classification, all sham groups were predominantly scaled into grade IVb.

In the "5 DAYS SHAM PBS" group 87.5% of the rats have class IVb arrhythmias and 12.5% class IVa. In the "5 DAYS SHAM NTG-PLACEBO" group 83.3% have IVb arrhythmias and 16.7% class IVa and in the "5 DAYS SHAM NTG" group 85.7% have IVb arrhythmias and 14.3% class Ma arrhythmias.

Figure 12:
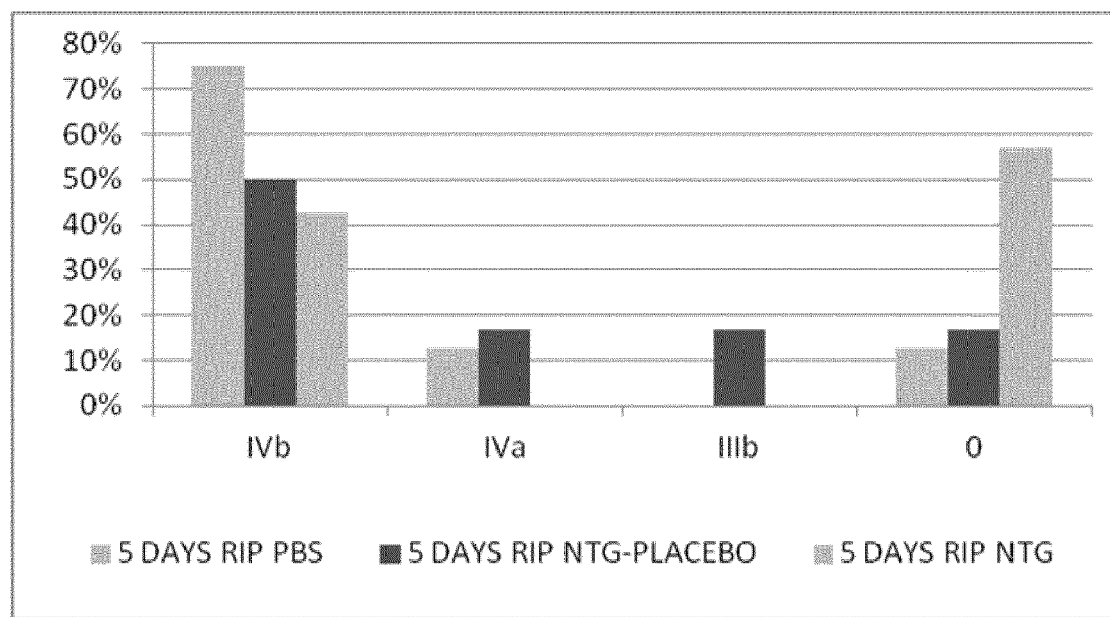

FIG. 12: Arrhythmias during FPO (module 2: NO intermittent (NTG)). Numbers of columns are given in consecutive order of the columns in group IVb. Column 1 shows 5 DAYS RIP PBS; column 2 shows 5 DAYS RIP NTG-PLACEBO; column 3 shows 5 DAYS RIP NTG.

While arrhythmias in both control groups, PBS and NTG-Placebo, were predominantly scaled into grade IVb, the NTG treated group was more often scaled into grade 0.

In the "5 DAYS RIP PBS" group, 75.0% of the rats have class IVb arrhythmias, 12.5% IVa and 12.5% class 0. Regarding the "5 DAYS RIP NTG-PLACEBO" group, 50.0% of the rats showed class 1Vb arrhythmias, 16.7% 1Va, 16.7% class IIIb and 16.7% class 0 arrhythmias. Interestingly, the "5 DAYS RIP NTG" group shows 42.9% class IVb arrhythmias and 57.1% class 0 arrhythmias.

Figure 13:
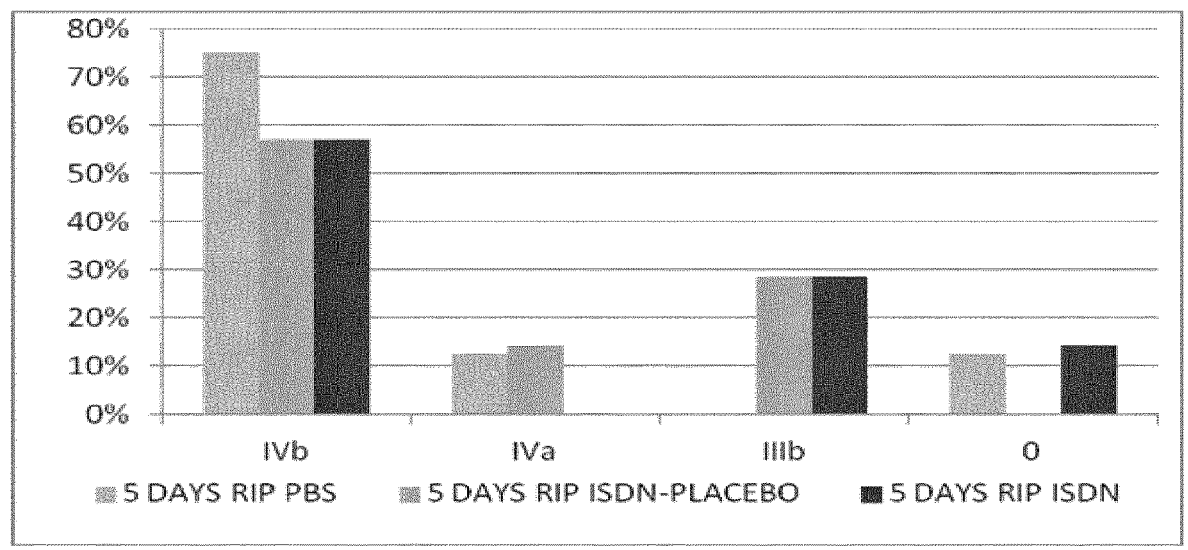

FIG. 13: Arrhythmias during FPO (module 3: NO continuous (ISDN retard)). Numbers of columns are given in consecutive order of the columns in group IVb. Column 1 shows 5 DAYS RIP PBS; column 2 shows 5 DAYS RIP ISDN-PLACEBO; column 3 shows 5 DAYS RIP ISDN.

In all groups, arrhythmias were similarly more often scaled into grade IVb.

In the "5 DAYS ISDN-PLACEBO" group, 57.1% of the rats have class IVb arrhythmias, 14.3% class IVa and 28.6% class IIIb. The "5 DAYS RIP ISDN" group shows less severe arrhythmias with 57.1% class IVb, 28.6% class IIIb and 14.3% class 0 arrhythmias.

Figure 14:
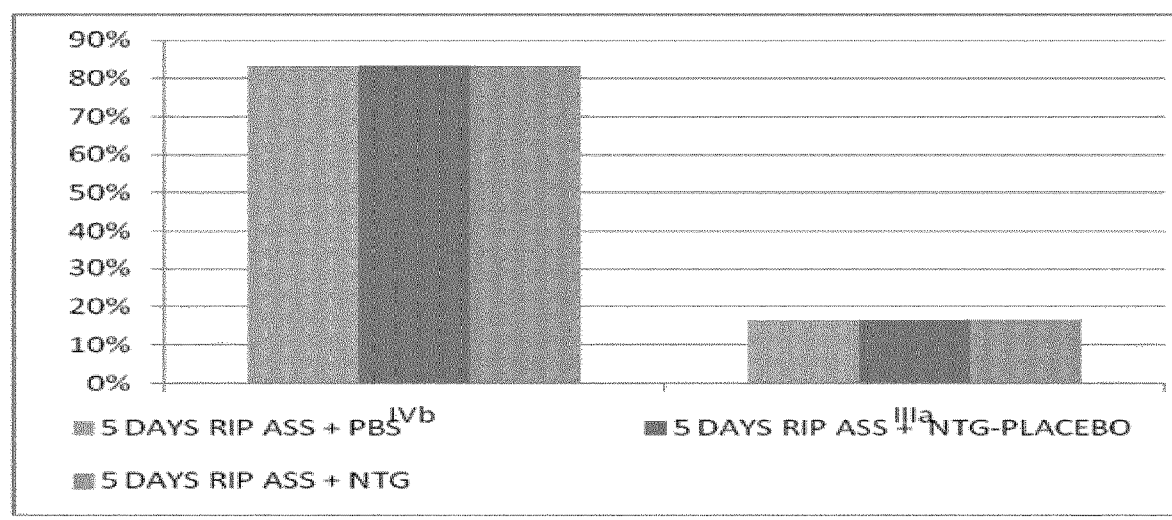

FIG. 14: Arrhythmias during FPO (module 4: NO intermittent plus ASA). Numbers of columns are given in consecutive order of the columns in group IVb. Column 1 shows 5 DAYS RIP ASA+PBS; column 2 shows 5 DAYS RIP ASA+NTG-PLACEBO; column 3 shows 5 DAYS RIP ASA+NTG.

Arrhythmias were similarly scaled more into grade IVb in all groups.

In the "5 DAYS RIP ASA+PBS" group, in the group treated with ASA+NTG-PLACEBO and in the "5 DAYS RIP ASA+NTG" group 83.3% of the rats posses class IVb arrhythmias and 16.7% class IIIa.

Figure 15:
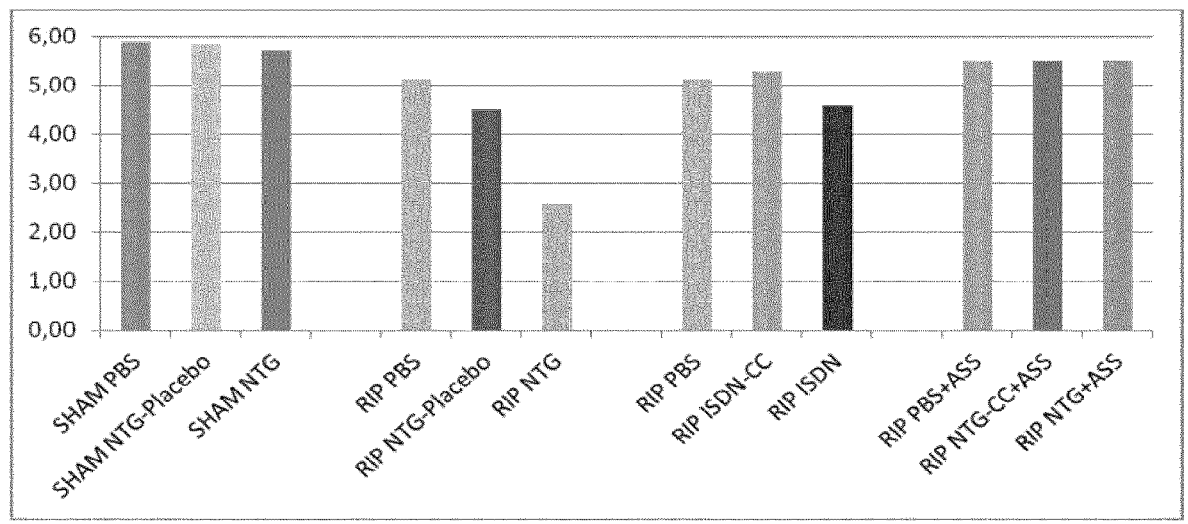

FIG. 15: VPB-Score. Column 1 shows SHAM PBS; column 2 shows SHAM NTG-Placebo; column 3 shows SHAM NTG; column 4 shows RIP PBS; column 5 shows RIP NTG-Placebo; column 6 shows RIP NTG; column 7 shows RIP PBS; column 8 shows RIP ISDN-Placebo column 9 shows RIP ISDN; column 10 shows RIP PBS+ASA; column 11 shows RIP NTG-Placebo+ASA; column 12 shows RIP NTG+ASA.

Regarding the percentage of each Lown grade of every group, a VBP score can be ascertained. The more animals show a higher grade, the higher is the VBP score.

The VBP score shows the percentage of each Lown grade of every group. The Sham-groups have higher VBP-scores. Compared to the group with an ischemic protocol (control group, treated with PBS), more rats show severe arrhythmias. The treatment with NTG revealed reduced arrhythmias, and consequently a lower VPB-Score. The VPB-Score in groups treated with ASA alone or NTG+ASA is higher compared to the controls (treated with PBS).

Figure 16:
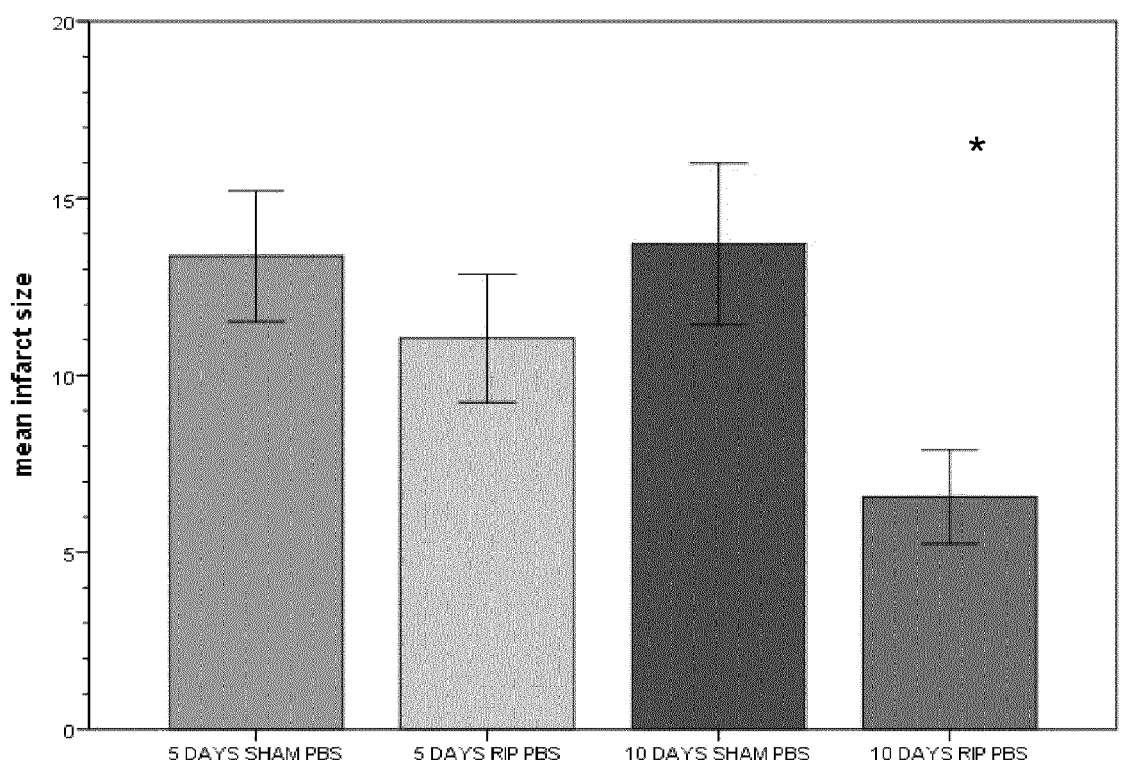

FIG. 16: Infarct size of 5-days- and 10-days-control-groups. Column 1 shows 5 DAYS SHAM PBS, n=8: 13.36 ±5.22%; column 2 shows 5 DAYS RIP PBS, n=8: 11.05±5.12%; column 3 shows 10 DAYS SHAM PBS, n=7: 13.71±6.04%; column 4 shows 10 DAYS RIP PBS, n=6: 6.57±3.26%; standard deviation is indicated by error bars; asterisk indicates significant compared to the shams (nominal p-value<0.013).

After an ischemic protocol of 5 days there is no significantly smaller infarct size measurable, but after a RIP of 10 days the infracted area is significantly decreased compared to the shams (nominal p-value <0.013).

After 90 minutes of LAD occlusion and 20 minutes reperfusion, infarct size was analyzed. The "10 DAYS RIP PBS" group has a significantly smaller infarct arca compared to the "10 DAYS SHAM PBS" group. There is no significance between both 5 DAYS groups.

Figure 17:
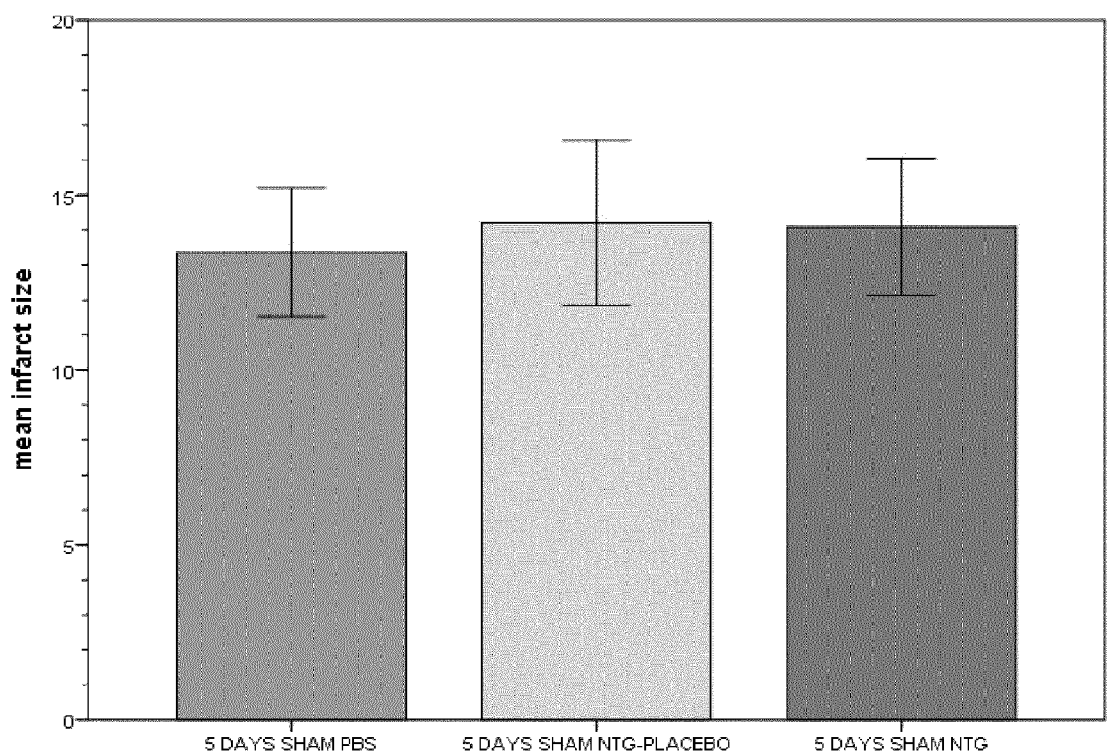

FIG. 17: Infarct size (module 1: Sham Operation (without the RIP)). Column 1 shows 5 DAYS SHAM PBS, n=8: 13.36±5.22%; column 2 shows 5 DAYS SHAM NTG-PLACEBO, n=6: 14.21±5.79%; column 3 shows 5 DAYS SHAM NTG, n=7: 14.09±5.18%; standard deviation is indicated by error bars.

The infarct size shows no difference between the SHAM groups.

There is no significance between the three SHAM groups.

Figure 18:
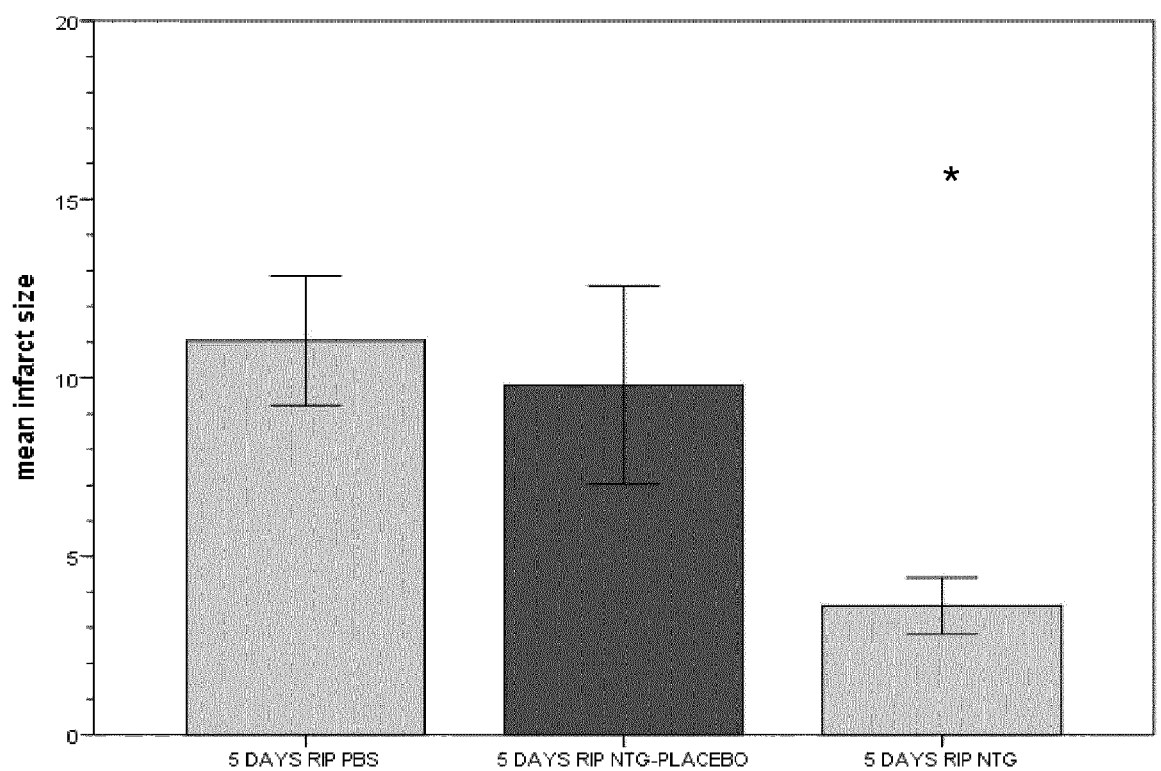

FIG. 18: Infarct size (module 2: NO intermittent (NTG)). Column 1 shows 5 DAYS RIP PBS, n=8: 11.05±5.12%; column 2 shows 5 DAYS NTG-PLACEBO: n=6; 9.80±6.79%; column 3 shows 5 DAYS RIP NTG, n=7: 3.61±2.08%; standard deviation is indicated by error bars, asterisk indicates significant compared to 5 DAYS RIP PBS (nominal p-value<0.017).

The infarct size is significantly smaller after treatment with NTG compared to controls (treated with PBS) (nominal p-value<0.033).

Compared to the "5 DAYS RIP PBS", a significantly smaller infarct area is observed in the "5 DAYS RIP NTG" group. There is no significance between the PBS and NTG-PLACEBO-group.

Figure 19:
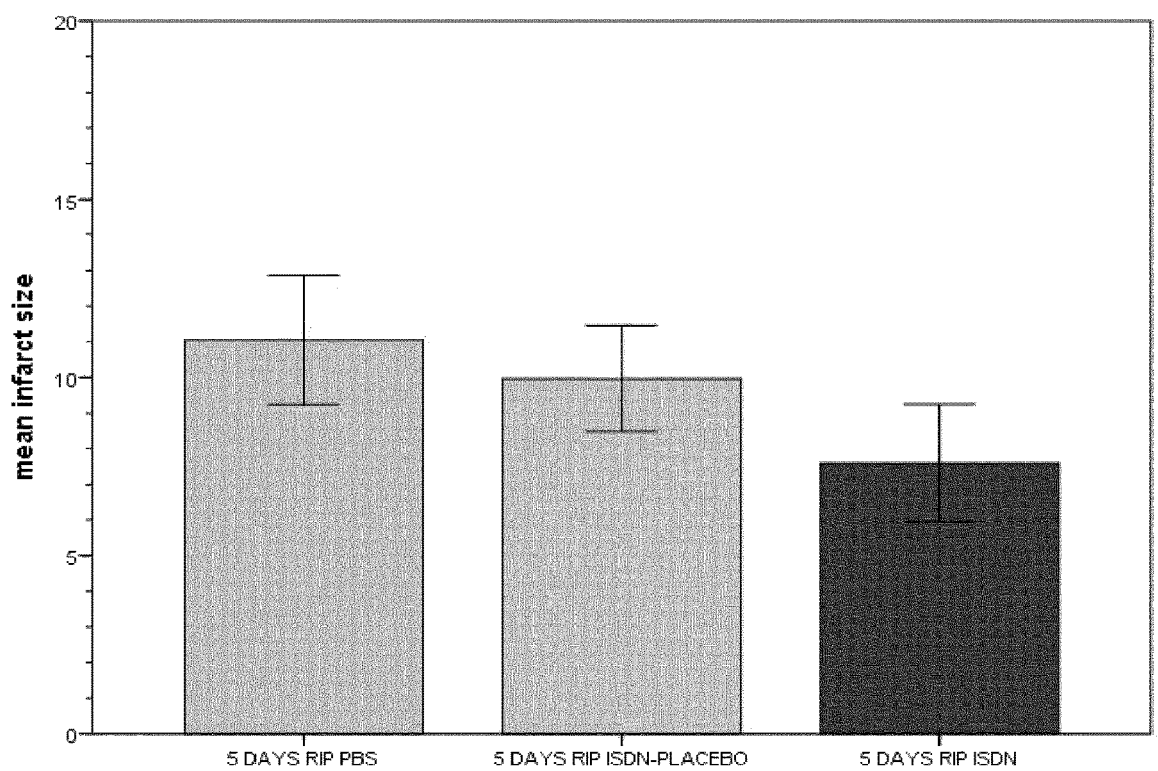

FIG. 19: Infarct size (module 3: NO continuous (ISDN retard)). Column 1 shows 5 DAYS RIP PBS, n=8: 11.05±5.12%; column 2 shows 5 DAYS ISDN-PLACEBO, n=6: 9.97±3.65%; column 3 shows 5 DAYS RIP ISDN, n=7: 7.59±4.38%; standard deviation is indicated by error bars.

The infarct size after treatment with ISDN is smaller compared to controls (treated with PBS or ISDN-Placebo), but there is no significance.

The infarct size in the ISDN group ("5 DAYS RIP ISDN") is smaller compared to the PBS group, as well as the ISDN-PLACEBO-group.

Figure 20:
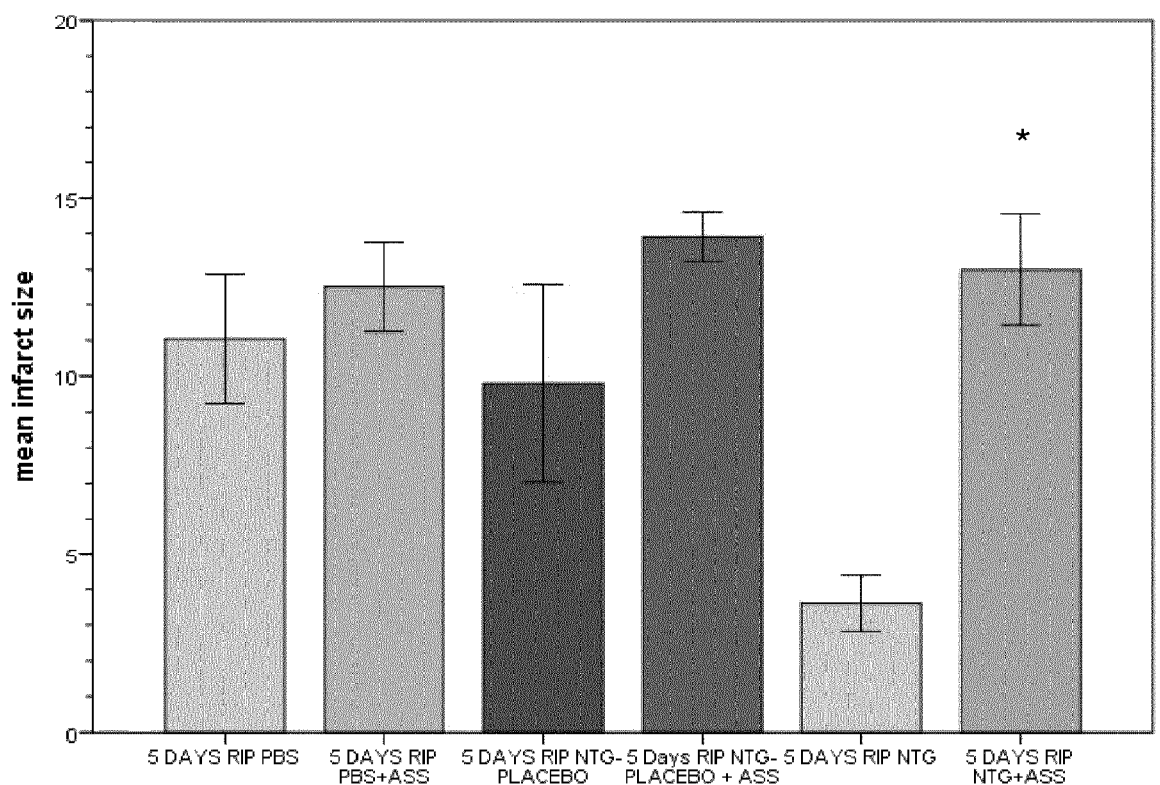

FIG. 20: Infarct size (module 4: NO intermittent plus ASA). Column 1 shows 5 DAYS RIP PBS, n=8; 11.05±5.12%; column 2 shows 5 DAYS RIP ASA+PBS, n=6: 12.51±3.05%; column 3 shows 5 DAYS NTG-PLACEBO: n=6; 9.80±6.79%; column 4 shows 5 DAYS RIP NTG-PLACEBO+ASA, n=6: 13.92 ±1.71%; column 5 shows 5 DAYS RIP NTG, n=7: 3.61±2.08%; column 6 shows 5 DAYS RIP NTG 30 ASA, n=6: 13.00±3.82%; standard deviation is indicated by error bars, asterisk indicates significant compared to 5 DAYS RIP NTG (nominal p-value<0.017).

The infarct size after treatment with NTG plus ASA is significantly increased compared to the treatment with NTG alone (nominal p-value <0.017).

The infarct size in the group treated with ASA ("5 DAYS ASA+PBS") is minimally increased compared to the PBS control group, as well as the ASA+NTG-PLACEBO-group. There is no difference between the ASA+NTG-group and the group treated with ASS and PBS. However, the infarct area in the NTG group is significantly smaller compared to the ASA+NTG group.

Figure 21:
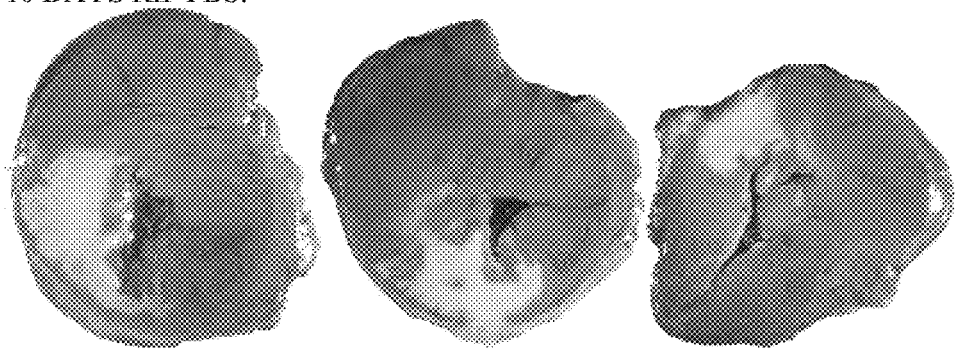
Figure 21:
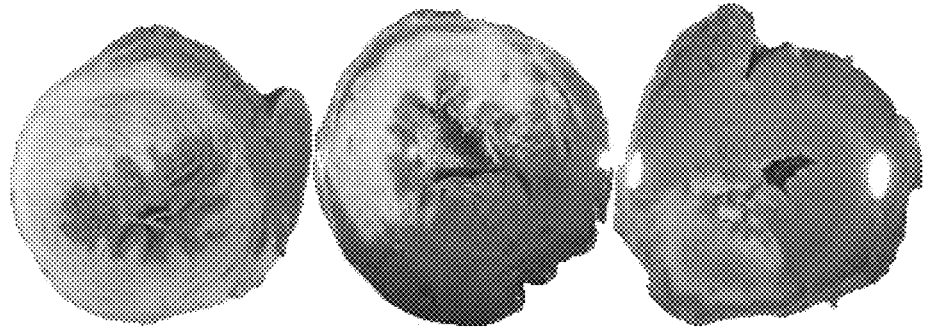
Figure 21:
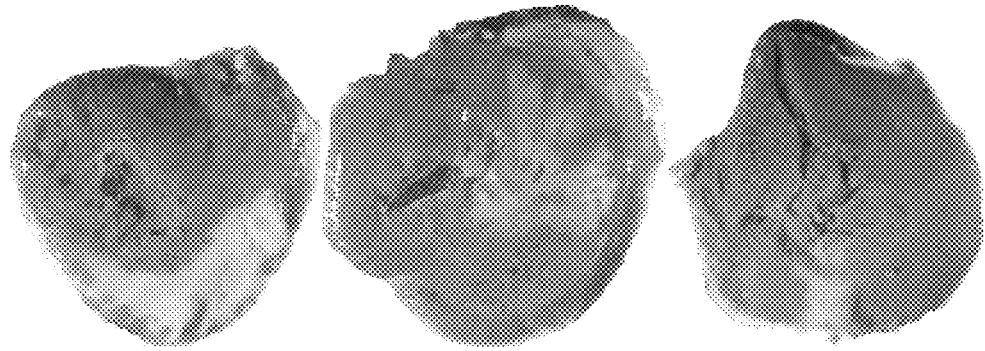
Figure 21:
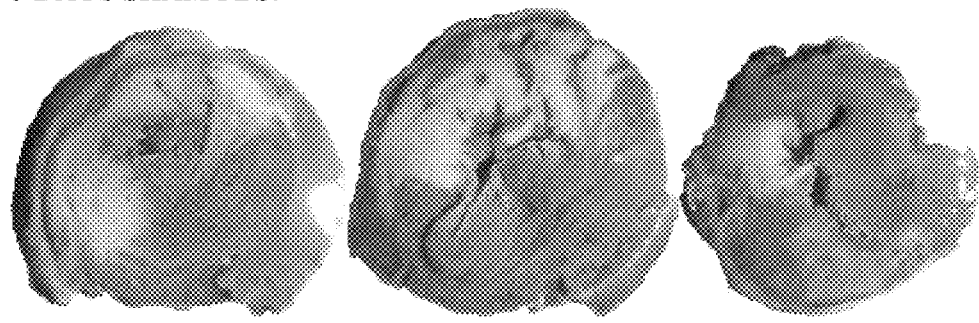
Figure 21:
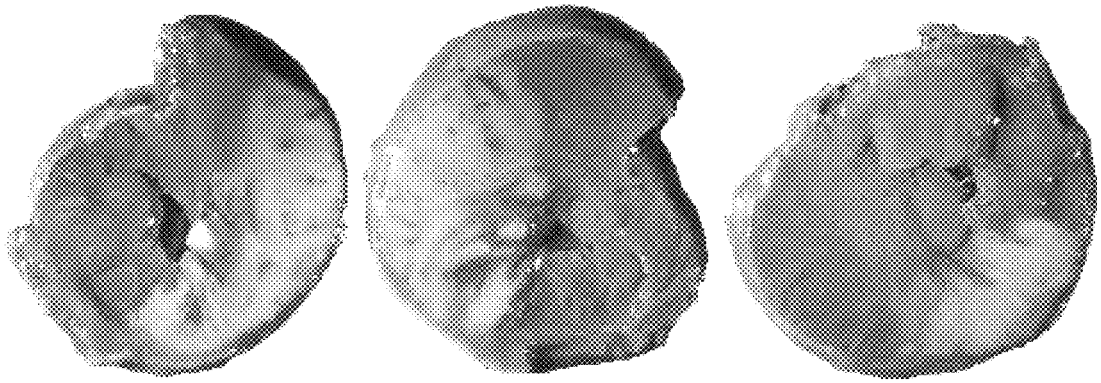
Figure 21:
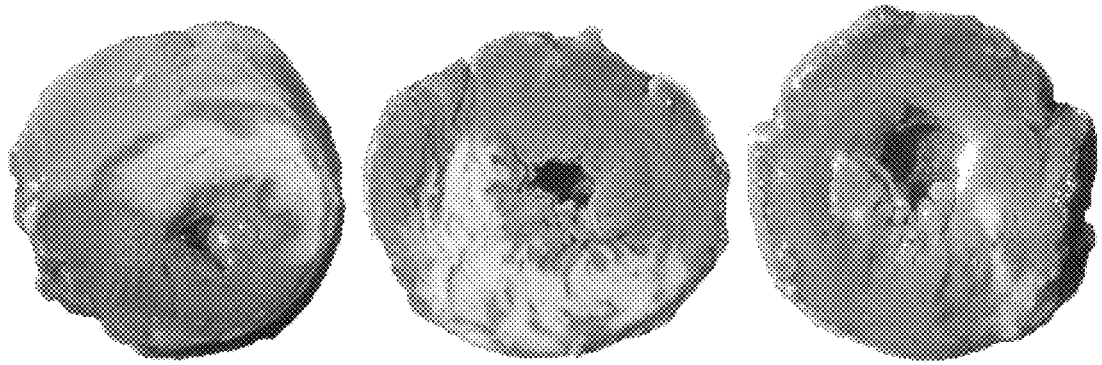
Figure 21:
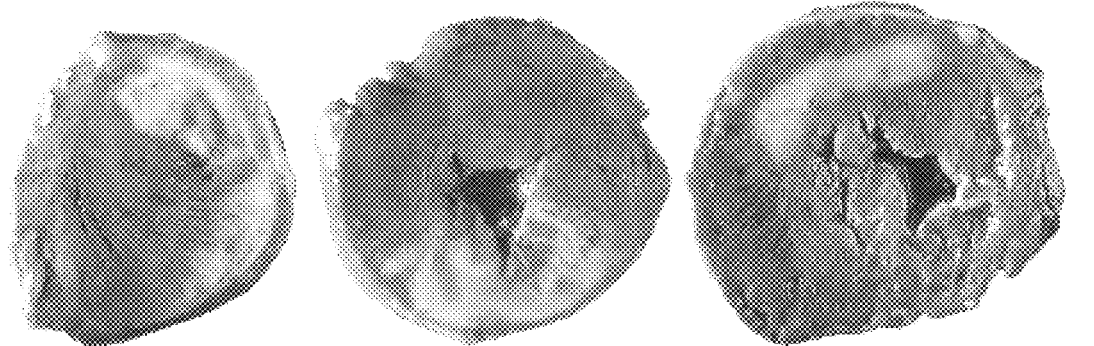
Figure 21:
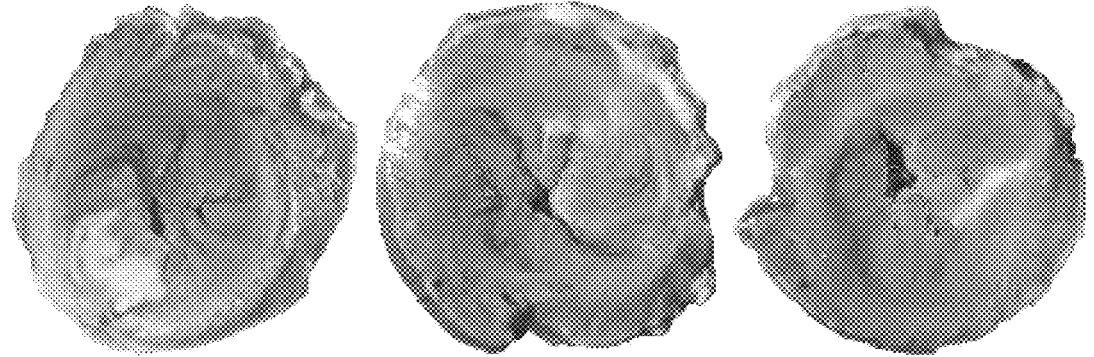
Figure 21:
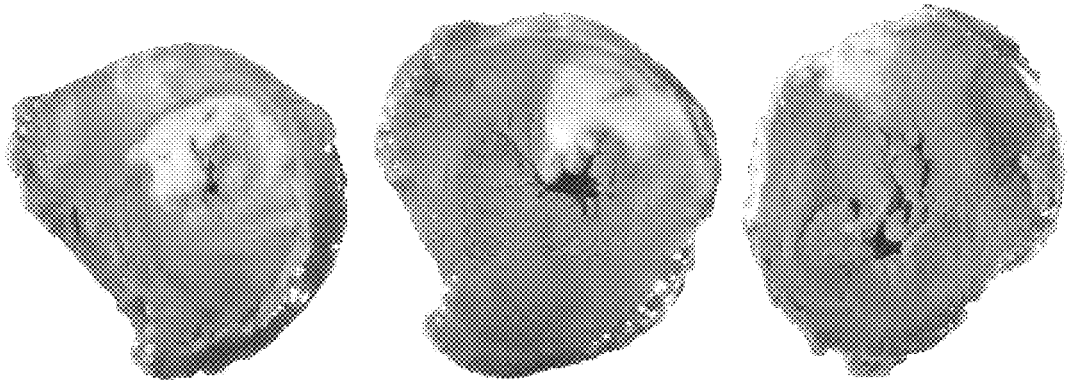
Figure 21:
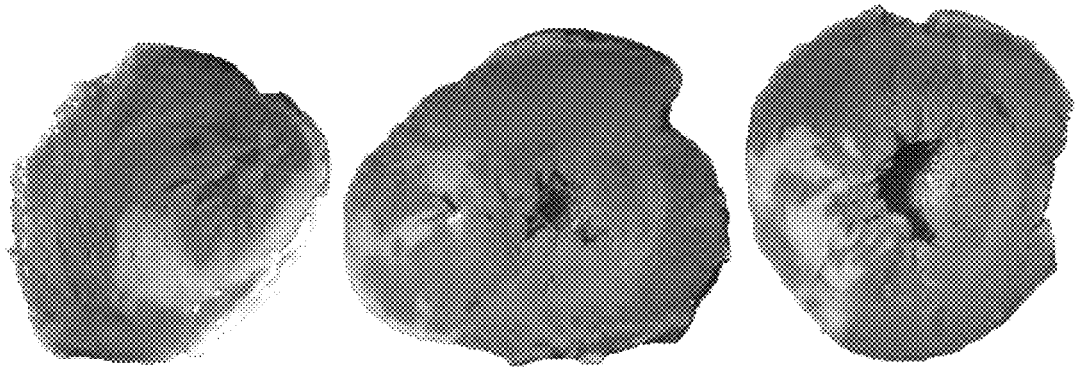
Figure 21:
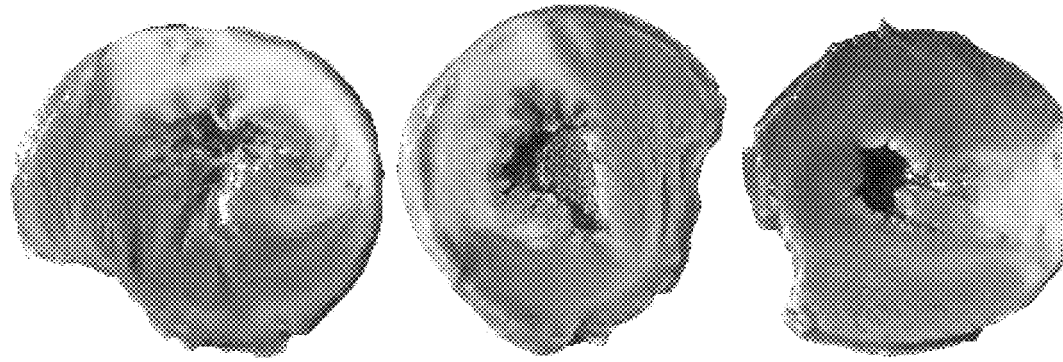
Figure 21:
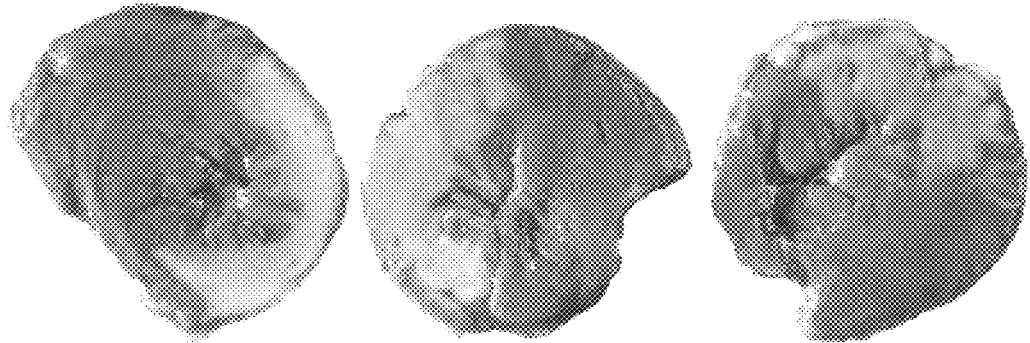
Figure 21:
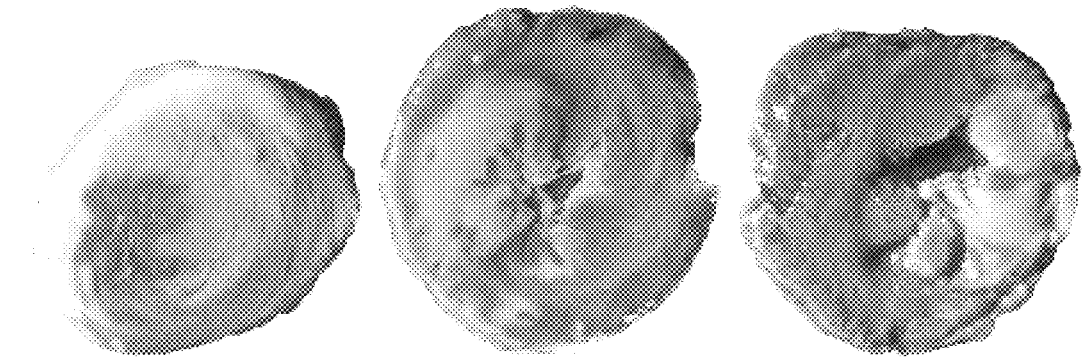

FIG. 21: TTC-staining. The pictures show slices of three levels. Infarcted tissue stains a pale-white since they lack the enzymes with which the TTC reacts. Thus the areas of necrosis are clearly discernible and quantifiable.

Figure 22:
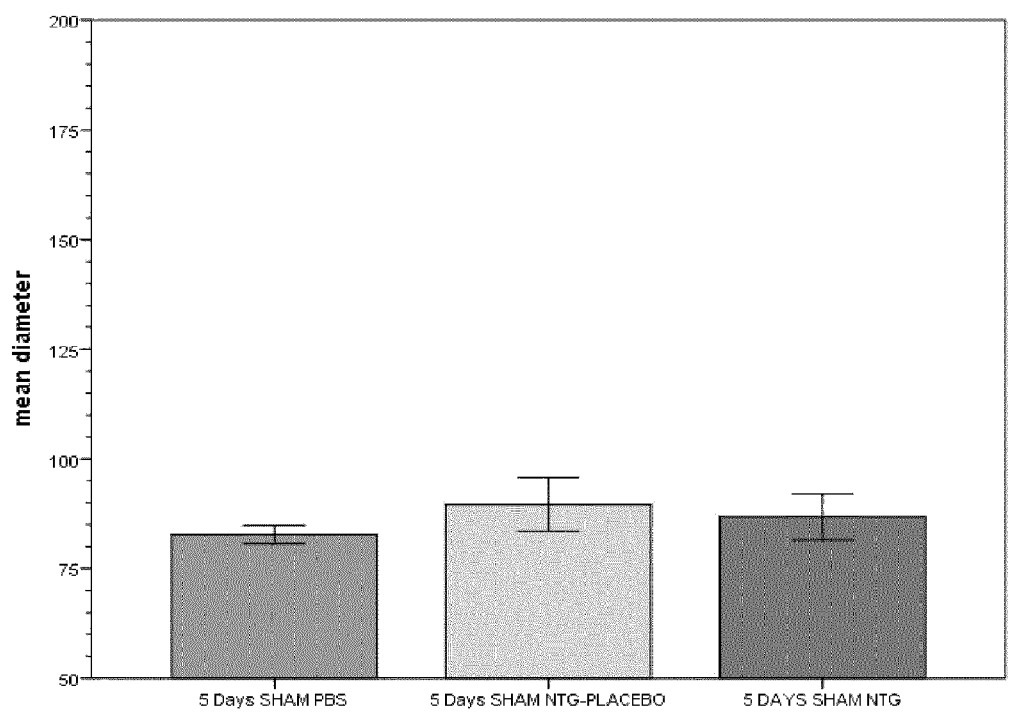

FIG. 22: Collateral diameters of ROI (module 1: Sham Operation (without the RIP)). Column 1 shows 5 DAYS SHAM PBS, n=3: 82.7±3.7 µm; column 2 shows 5 DAYS SHAM NTG-PLACEBO, n=3: 89.6 µm±10.6 µm; column 3 shows 5 DAYS SHAM NTG, n=3: 86.8±9.0 µm; standard deviation is indicated by error bars.

There is no growth of collaterals and no differences measurable between the SHAM groups.

There is no significance between the three SHAM-groups.

Figure 23:
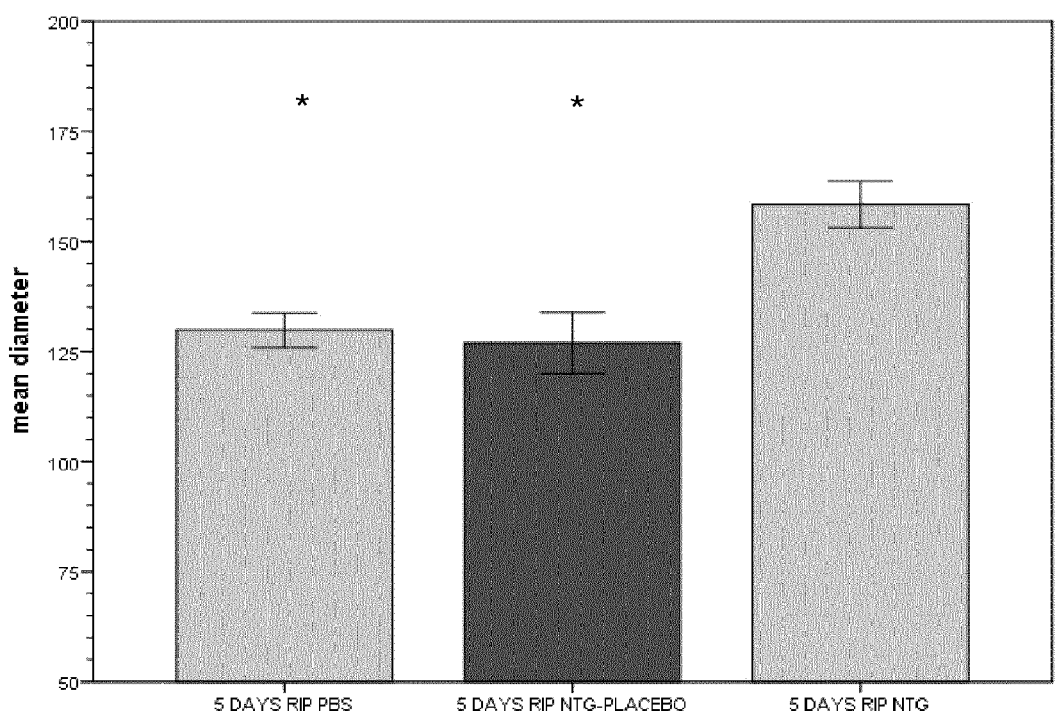

FIG. 23: Collateral diameters of ROI (module 2: NO intermittent (NTG)). Column 1 shows 5 DAYS RIP PBS, n=3: 129.8±6.9 µm; column 2 shows 5 DAYS RIP NTG-PLACEBO: n=3; 127.0±12.1 µm; column 3 shows 5 DAYS RIP NTG, n=3: 158.4±9.2 µm; standard deviation is indicated by error bars, asterisk indicates significant compared to 5 DAYS RIP NTG (nominal p-value<0.033).

Diameters of collaterals are significantly increased by treatment with NTG compared to controls (treated with PBS or NTG-Placebo) (nominal p-value<0.033).

Compared to the "5 DAYS RIP PBS", the diameters of the collaterals in the ROI in the "5 DAYS RIP NTG" group are significantly increased. There is no difference between the PBS and NTG-PLACEBO-group.

Figure 24:
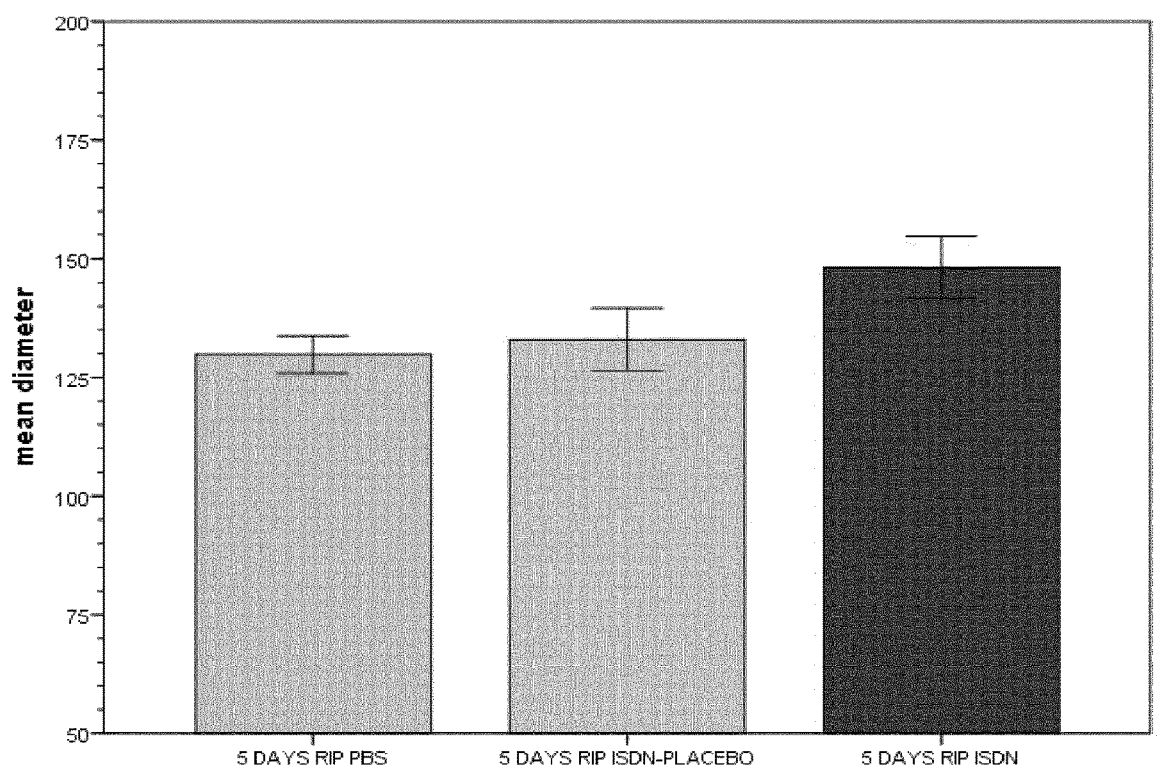

FIG. 24: Collateral diameters of ROI (module 3: NO continuous (ISDN retard)). Column 1 shows 5 DAYS RIP PBS, n=3: 129.8±6.9 µm; column 2 shows 5 DAYS ISDN-PLACEBO, n=3: 133.0±11.5 µm; column 3 shows 5 DAYS RIP ISDN, n=3: 148.2±11.3 µm; standard deviation is indicated by error bars.

No differences are measurable in the diameter of collaterals after treatment with ISDN or ISDN-Placebo.

The diameters of the collaterals in the ISDN group ("5 DAYS RIP ISDN") are enhanced compared to the PBS group, as well as compared to the ISDN-PLACEBO group.

Figure 25:
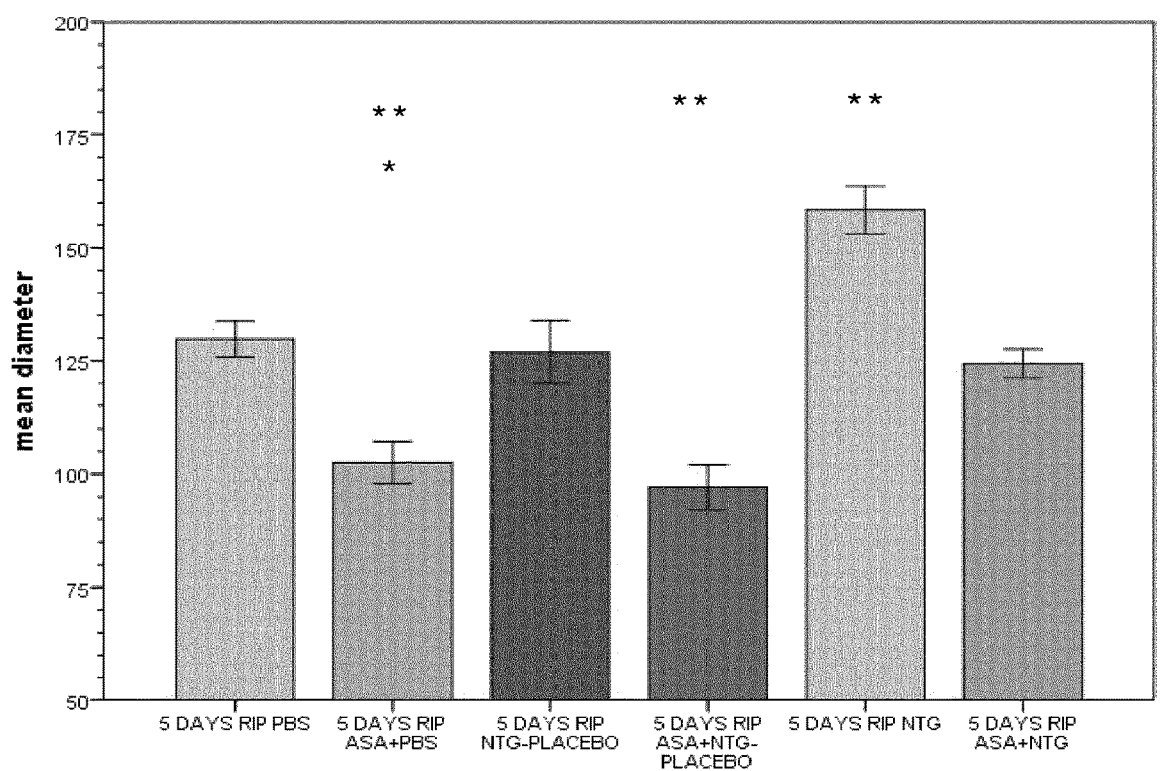

FIG. 25: Collateral diameter of ROI (module 4: NO intermittent plus ASA). Column 1 shows 5 DAYS RIP PBS, n=3; 129.8±6.9 gm; column 2 shows 5 DAYS RIP PBS+ASA, n=3: 102.5±8.0 µm; column 3 shows 5 DAYS RIP NTG-PLACEBO: n=3; 127.0±12.1 µm; column 4 shows 5 DAYS NTG-PLACEBO+ASA, n=3: 97.1±8.6 µm; column 5 shows 5 DAYS RIP NTG, n=3: 158.4±9.2 µm; column 6 shows 5 DAYS RIP ASA+NTG, n=3: 124.4±5.6 µm; standard deviation is indicated by error bars, one asterisk indicates significant compared to 5 DAYS RIP PBS (nominal p-value<0.039); double asterisk indicates significant compared to 5 DAYS RIP ASA+NTG (nominal p-value<0.039).

Diameters of collaterals are significantly smaller after treatment with ASA compared to control (treated with PBS) (*nominal p-value<0.039). An additional treatment with NTG abolished the inhibiting effect of ASA, but NTG-treatment alone shows significantly increased diameter compared to treatment with NTG+ASA (** significant compared to 5 DAYS RIP ASA+NTG, nominal p-value<0.039).

The diameters in the group treated with PBS and ASA are significantly smaller compared to the PBS control group, but there is no significance compared to the ASA+NTG-PLACEBO-group. In the ASA+NTG-group diameters are significantly increased compared to the group treated with PBS and ASA.

Figure 26:
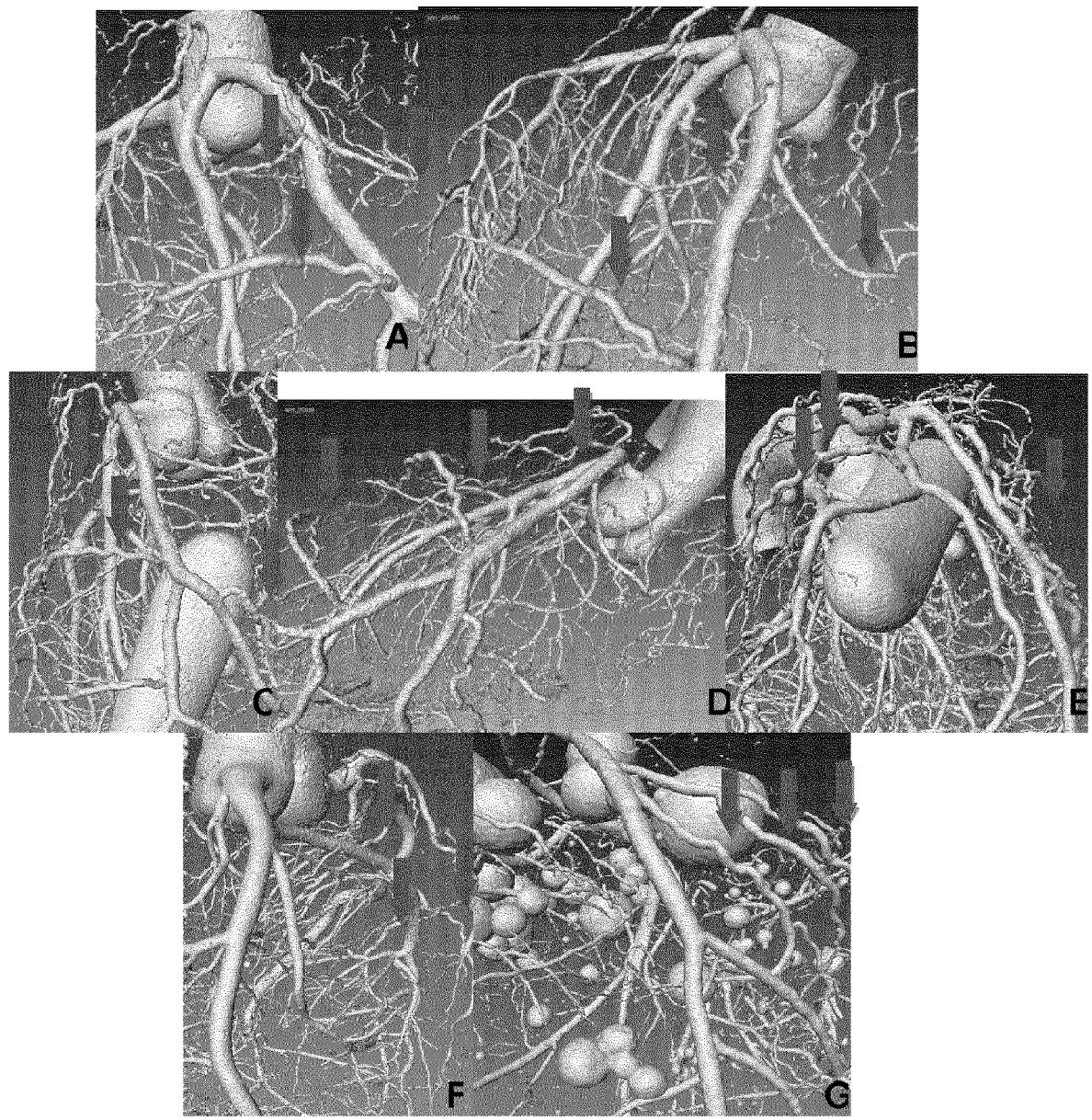

FIG. 26: MicroCT imaging of the "ROI": (A) "5DAYS SHAM PBS"; (B) "5DAYS SHAM NTG"; (C) "5DAYS RIP ISDN"; (D) "5DAYS RIP PBS"; (E) "5DAYS RIP NTG"; (F) "5DAYS RIP ASA+PBS; (G) "5DAYS RIP ASA+NTG".

The pictures show the growth of the collateral diameter in the region of interest by the ischemic protocol treated with PBS (D), NTG (E), or ISDN (C) compared to SHAM treated with PBS (A) or NTG (B) Inhibition of collateral growth by treatment with ASA (F) is partially abolished by additional treatment with NTG (G).

Figure 27:
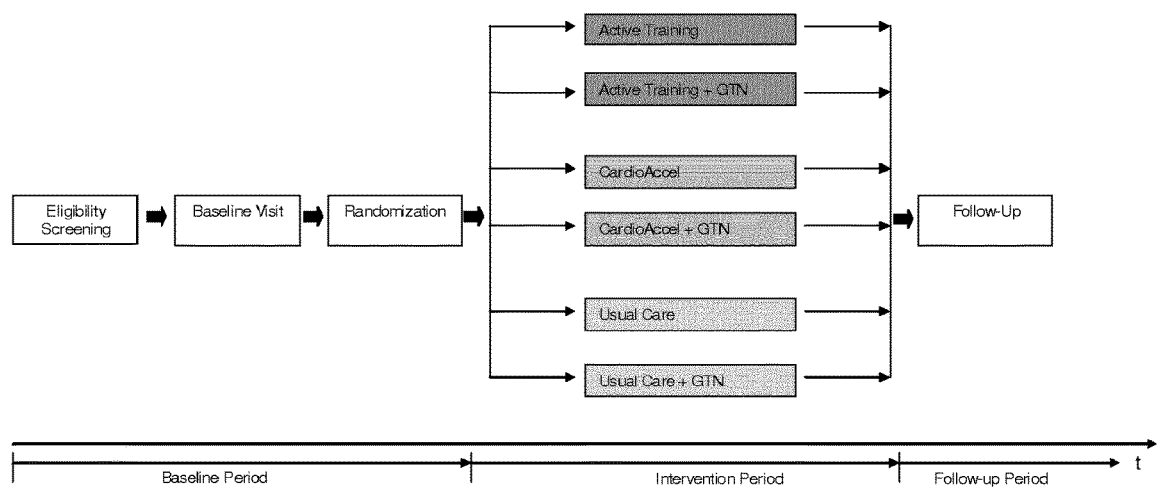

FIG. 27: Study Flow Chart. Duration of the baseline period is estimated to be approximately 2 weeks. Duration of the intervention period will be six weeks. The follow up period will include an immediate investigation (one day up to maximal three days after the intervention period) and a long-term follow up investigation (1 month after intervention period).

EXAMPLE 1

Pre-Clinical Study

1. INTRODUCTION

One important mechanism of arteriogenesis is the induction of shear stress across recruited collateral arteries.

NO plays a fundamental role in this scenario, since it regulates the vasodilatory capability of the artery as well as therapeutic proliferation aspects on the smooth muscle cells of collateral arteries.

Here we evaluated the effects of Nitrolingual akut® Spray (G. Pohl-Boskamp GmbH & Co.KG, Hohenlockstedt, Germany; U.S. American brand name Nitrolingual® Pumpspray) in a unique non-myocardial infarct arteriogenesis model. Collateral growth in this model is induced via repetitive occlusion of the left anterior descending coronary artery (LAD). Infarct size in these animals was measured as the endpoint at the end of the experiment. Thus, no interference between myocardial infarction and arteriogenesis has weaken the experiment. Moreover we evaluated the effect of acetyl salicylic acid (ASA) in this model of repetitive coronary occlusion as a possible inhibitor of arteriogenesis. We evaluated whether a concomitant application of NO (intermittent use of nitroglycerin) may compensate for this negative effect of ASA.

2. MATERIALS AND METHODS 1.1. Animal Preparation

Male Sprague-Dawley rats (300 g body weight at study start; n=182) are used for experiments. For surgery (day 0), rats are premedicated (ketamine 50 mg/ml plus xylazine 4 mg/ml intraperitoneal) and intubated. Oral intubation (I4-G polyethylene tubing) is done under direct observation of the vocal cords with an otoscope. General anesthesia is introduced and maintained by isoflurane inhalation (1.0% to 2.0%, with 100% oxygen). Body temperature is controlled at 37° C. by an electric heating table. Surgery is performed using aseptic technique. The animal is initially placed on its dorsal side and cutaneous clips are fixed. With a BioAmp differential amplifier coupled to a PowerLab data acquisition system (AD Instruments) ECG parameters (heart rate) are monitored and recorded during surgery. The heart is exposed by left thoracotomy. A mini-pneumatic snare occluder (see the Mini-Pneumatic Snare Occluder section for details) is implanted around the mid to proximal left anterior descending coronary artery (LAD). Confirmation that the occluder is functional, i.e., producing myocardial ischemia, is determined initially by observation of blanching and hypokinesis of the left ventricle (LV) and by observation of the electrocardiogram (ST elevation) during inflation. Rats are randomly divided into 4 therapeutic modules:

Module 1: Sham Operation
Module 2: NO intermittent (nitroglycerin)
Module 3: NO continuous (retard preparation of isosorbide dinitrate)
Module 4: NO intermittent plus ASA After instrumentation and measurements, the chest is closed under positive end-expiratory pressure, and the thoracic cavity is evacuated of air. The occluders are tunneled subcutaneously and exteriorized between the scapulae. These catheters are protected by a stainless steel spring coil connected to a ring that is secured subcutaneously between the scapulae. After the surgery, analgesic (buprenorphine 0.05 mg/kg SC) and antibiotic (enrofloxacin 10 mg/kg SC) are administered. Rats are observed in a recovery cage for 2 hours and then transferred to the animal care facility where they are continuously monitored by technicians. Postoperatively, buprenorphine (0.5 mg/kg SC) is given for pain twice a day for 8 resp. 13 days. On the third day after the surgery (day 3), ischemic protocol is started. After 5 resp. 10 days (only in module 1A and 2A) of the experimental protocol (day 8 resp. day 13), the rats are anesthetized, and the chest is opened by mid thoracotomy. In the micro-CT group, the hearts are immediately excised. For the final infarct size detection the LAD is permanently occluded (final permanent occlusion, FPO) and infarct size is measured via TTC staining 1.2. Mini-Pneumatic Snare Occluder for Rat Heart A mini-pneumatic snare occluder is used consisting of a mini-balloon, sheath tubing, suture, and catheter. The balloon (7 mm long) is made of soft latex membrane and is sufficiently pliable to give negligible physical force on the coronary vessels during balloon deflation. The balloon is mounted within an umbrella sheath (3.2 or 4.8 mm in diameter, 12 mm in length; protects the balloon from fibrous infiltration). Prolene (5-0) is passed around the LAD and attached to the sheath, securing the occluder to the heart, so that myocardial ischemia is produced by balloon inflation. Inflation volume is small (0.2 to 0.25 mL air), but occlusion occurs by 2 physical actions: "crimping" the LAD toward upward/outside and compressing the LAD by the inflated balloon/sheath. The balloon is connected to a catheter (PE-50) that is exteriorized. Balloon inflation and deflation are controlled from outside the rat cage.

1.3. Measurements of ECG Parameters

In all four modules (1-4) at the beginning (day 3) and the end (day 8 resp. day 13) of the experimental protocol (RIP) the coronary occlusion is performed for 40 seconds (equivalent to an occlusion in the RIP; see page 6) and during FPO for 90 minutes (day 8 resp. day 13) ECG parameters are measured to examine the heart rate and ST elevation. Furthermore, the occuring arrhythmias during FPO are determined. According to Lown's classification, every animal shows a certain grade. The higher a grade, the more severe arrhythmias are. To illustrate the mean severity of an entire group more descriptive, a VPB score is ascertained. For that, every Lown grade refers to a particular factor (grade 0=factor 0; grade I=factor 1; grade II=factor 2; grade IIIa=factor 3; grade IIIb=factor 4; grade VIa=factor 5; grade VIb=factor 6 and grade V=factor 7). Every group has a different percentage of animals presenting each grade. The percentage of the respective grades are multiplied with the appropriate factor leading to individual results which are then summed up to the VPB score of the whole group. Consequently, a group of animals with higher Lown grades has a correlatively high VPB score.

1.4. Coronary Microvascular Imaging With Micro-CT

In addition Micro-CT is used as a further endpoint to image collaterals. One group of rats (3 rats of each group in each module; total of 36 rats) is prepared for coronary vascular visualization via micro-CT. The coronary circulation is filled with contrast medium (yellow microfil) by modification of the methodology for micro-CT study in the rats. The viscosity of the contrast medium enables filling up to coronary arteriolar level with no or minimal filling of capillaries. The excised heart is immediately cannulated by an aortic cannula, and coronary circulation is perfused retrogradely at 85 mm Hg. A perfusate (25° C. to 27° C. saline with 2% procaine) is used to avoid myocardial metabolic contraction and maximally dilate the coronary vasculature. Polyethylene tubing is inserted into the LV via a left appendage through the mitral valve to unload the LV. Warmed contrast medium (42° C.) is injected at a pressure of 85 mmHg for 3 minutes while perfusion pressure is monitored. The heart is cooled by immersion into cold saline (0° C. to 4° C.) until the (yellow microfil) solidified. Then, the heart is removed and fixed in 4% paraformaldehyde solution (4° C.) overnight. Whole hearts are used for micro-CT imaging of coronary collateral growth. The coronary vasculature is visualized with micro-CT. In brief, the whole heart is scanned in 1° increments around 360° about its apex-to-base longitudinal axis. The spatial resolution selected in the present study has an 18*18*18 m³ voxel size to focus on the size of collateral vessels and to minimize the signals from smaller vessels. Finally, CT data are reconstructed as 3D images. The main purpose of these images is to establish the presence or absence of arterial-arterial anastomotic connections. Collateral vessels, i.e., arterial-arterial anastomotic connections, are measured by independent observers for the groups. Collateral arterial network morphology is analyzed with Amira 5.2.2 software (Visage Imaging, Berlin, Germany).

1.5. Experimental Protocol

The repetitive ischemia protocol (RIP) is introduced by automatised inflation of the occluder using the following protocol: 40 seconds of occlusion every 20 minutes for 2 hours 20 minutes, followed by a period of "rest" (deflation) for 5 hours 40 minutes. This 8-hour set is repeated 3 times a day for 5 resp. 10 days (only in module 1A and 2A). The LAD is occluded automatically by remote inflation or deflation through the catheter. In sham rats (see module 1), the balloon is implanted, but RIP is not applied. Rats under RI protocol are randomly divided into the three modules 2, 3 and 4.

1.6. Infarct Size Detection

Infarct size is detected by TTC staining after final permanent occlusion. After 5 resp. 10 days (only in module 1A and 2A) of the experimental protocol, the occluder is inflated permanently for 90 minutes. Infarct size is measured by TTC staining (n=10/group). Therefore rats are anaesthesized and undergo again the ECG recording to confirm the occlusion (ST elevation) and to calculate ECG parameters and the numbers of arrhythmias. In animals without collaterals, coronary occlusion causes deterioration of systemic hemodynamics and arrhythmias, including premature ventricular contractions, ventricular tachycardia, and ventricular fibrillation; in animals with well developed co llaterals, no such adverse effects are noted. The ECG parameters were recorded and analysed using a computerized program (Lab chart 7).

The chest is opened by mid thoracotomy. The heart is immediately excised and sectioned from apex to base in 2-mm-thick transverse slices parallel to the atrioventricular groove. Slices are incubated with 0.09 mol/L sodium phosphate buffer containing 1.0% triphenyl tetrazolium chloride (TTC) and 8% dextran for 20 min. at 37° C. Slices are fixed in 10% formaldehyde and then photographed with a digital camera mounted on a stereomicroscope. The infarcted size is quantified using a computerized planmetric program (Adobe Photoshop). The infarcted area is indentified as the TTC-negative tissue and is expressed as a percentage of the area of the left ventricle (LV).

1.7. Details Regarding Testing Compounds

| | |
|---|---|
| ASA | Merck Chemicals |
| NO intermittent (NTG) | nitroglycerin solution; Nitrolingual akut ® Spray, G. Pohl-Boskamp GmbH & Co. K G, Hohenlockstedt, Germany |
| NO continuous (ISDN retard) | isosorbide dinitrate retard pellets; Nitrosorbon ® retard; G. Pohl-Boskamp GmbH & Co. K G, Hohenlockstedt, Germany |
| Carrier compound for NO intermittent (NTG-Placebo) | placebo solution of Nitrolingual akut ® Spray, Pohl-Boskamp GmbH & Co. K G, Hohenlockstedt, Germany |
| NO continuous Carrier Compound (ISDN-Placebo) | neutral pellets of Nitrosorbon ® retard; G. Pohl-Boskamp GmbH & Co. K G, Hohenlockstedt, Germany |
| Control buffer | PBS (phosphate buffered saline) |

1.8. Route, Timepoint and Concentration of Delivery to Animals

All medication (ASA and NTG and ISDN retard) is given upfront to a following occlusion time of the device. The control buffer (PBS) is given in the same way prior to the first two occlusions.

NO Intermittent (NTG)

A new test solution is prepared every morning at eight o'clock. The solution is taken from the vials via syringes.

NO intermittent (NTG) is given twice a day with a time interval of 8 hours. Due to the chronic instrumentation of the rats and to avoid further stress, NTG is given via buccal application. 50 µl of the daily prepared test solution containing 17.37 µg nitroglycerin (equivalent to a human dose of 0.8 mg, as calculated by the formula dosis/animal [mg]=metabolic body weight [kg$^{0.75}$]*human dosis [mg/kg] *recalculation factor [kg/kg$^{0.75}$] according to Löscher, W., Ungemach, F. R., Kroker, R., 1998, Blackwell Science, 3rd edition) is administered per buccal application in module 1, 2 and 4. The time point of application is directly upfront to balloon inflation at 9 a.m. and 5 p.m., thus with maximal effects on recruited collateral arteries.

This concentration is taken from the above mentioned reaction vials right before administration.

Carrier compound solution served as a stock solution for the preparation of the test solution.

Carrier Compound for NO Intermittent (NTG-Placebo)

Carrier compound is administered in a way identical to NO intermittent.

NO Continuous (ISDN retard)

The medication for prolonged NO delivery (retard preparation isosorbide dinitrate=long-acting nitrate ISDN) is delivered as retarded pellets 1× per day.

For the retard preparation ISDN in a dosage of 2.6 mg ISDN/rat is chosen. Therefore 13 mg pellets arc suspended in 0.5 ml drinking water and arc applied via gavage at 9 a.m. every morning (equivalent of a human dose of 2 mg/kg/bw).

NO continuous Carrier Compound (ISDN-Placebo)

Carrier compound is administered in a way identical to NO continuous.

No Intermittent Plus ASA (Acetylsalicylic Acid)

Every morning at 9.30 a.m. 2.22 mg ASA per rat is given dissolved in 0.5 ml drinking water via gavage directly into the stomach.

The ASA concentration of 2.22 mg ASA per rat (6.34 mg/kg bw) correlates with the human dosage of 100 mg/day.

1.9. Animals and Groups 10 rats per groups (FPO=final permanent occlusion to induce infarcts) Group d: 3 additional animals are treated with the same medications and ligation scheme like the corresponding groups a, b and c, but without FPO. These 9 animals per module are used for micro CT images.

Module 1: Sham Operation (without the RIP):
A. Control buffer (phosphate buffered saline PBS) with functional FPO for infarct size detection n=20
  1. n=10: "5 DAYS SHAM PBS"
  2. n=10 "10 DAYS SHAM PBS"
B. Carrier compound without NO plus functional FPO for infarct size detection n=10: "5 DAYS SHAM NTG-PLACEBO"
C. NTG with functional FPO for infarct size detection n=10: "5 DAYS SHAM NTG"
D. A1.) n=3 A2.) n=3 B) n=3 C) n=3 for micro CT images n=12
  total: n=52
Module 2: NO intermittent:
A. intermittent control buffer with functional FPO for infarct size detection n=20
  1. n=10: "5 DAYS RTP PBS"
  2. n=10 "10 DAYS RIP PBS"
B. intermittent Carrier compound plus functional FPO for infarct size detection n=10: "5 DAYS RIP NTG-PLACEBO"
C. Intermittent NTG with functional FPO for infarct size detection n=10: "5 DAYS RIP NTG"
D. A1.) n=3 A2.) n=3 B) n=3 C) n=3 for micro CT images n=12
  total: n=52
Module 3: NO Continuous:
A. Continuous Control buffer (drinking water) with functional FPO for infarct size detection (n=10): "5 DAYS RIP DW"
B. Continuous Carrier compound plus functional FPO for infarct size detection n=10: "5 DAYS RIP ISDN-PLACEBO"
C. Continuous NO functional FPO for infarct size detection n=10: "5 DAYS RIP ISDN"
D. A.) n=3 B.) n=3 C.) n=3 for micro CT images n=9
  total: n=(39)
Module 4: NO Intermittent Plus ASA:
A. Intermittent Control buffer plus ASA with functional FPO for infarct size detection n=10: "5 DAYS RIP PBS+ASA"
B. Intermittent NO Carrier compound plus ASA plus functional FPO for infarct size detection n=10: "5 DAYS RIP NTG-PLACEBO+ASA"
C. Intermittent NTG plus ASA functional FPO for infarct size detection n=10: "5 DAYS RIP NTG+ASA"
D. A.) n=3 B.) n=3 C.) n=3 for micro CT images n=9
  total: n=39

2. STATISTICAL ANALYSIS

All data are given as mean±SD. Graphics are shown as mean±SEM. Results obtained by measuring ST segment elevation, infarct size and vessel diameters are analysed for statistical significance by using the SPSS 20 software package (IBM SPSS Statistics, N.Y., USA). ANOVA with a false discovery rate, FDR, correction is used. p values are adjusted for multiple testing using a FDR procedure to achieve an experiment-wide significance of p≤0.05. FDR takes into account the number of null hypotheses rejected and has been shown to increase statistical power as compared to Bonferroni correction.

3. RESULTS 3.1 Final Permanent Occlusion

LAD occlusion allowed a prospective study of the function of collateral vessels. Such vessels can protect myocardial tissue at risk of ischemia after coronary occlusion.

At the end of the RI protocol the permanent LAD occlusion is performed in one subgroup of all groups and ECG parameters to examine ST segment elevation and ventricular arrhythmias are measured. After 90 minutes of permanent occlusion the infarcted area is determined.

3.2 ECG Analysis

Electrocardiographic manifestations of ischemia initiated by LAD occlusion are less pronounced when collateral vessels are present.

3.3 ST Segment Elevation

During LAD occlusion there is an inverse correlation between the magnitude of ST segment elevation and the extent of the collateral supply.

Collateral function is an important determinant of the direction of ST segment response to ischemia during acute coronary occlusion. Reversible ST segment elevation during acute LAD occlusion is related to inadequate collateral arterial function. In patients with reversible ST segment depression, coronary collateral function appears to be better and, as a consequence, shows less ischemia results.

During the 90 minutes occlusion the ST segment elevation in the "10 DAYS SHAM PBS" is significantly higher compared to the "10 DAYS RIP PBS" group (10 DAYS SHAM, n=7: 0.124±0.039 mV; 10 DAYS RIP, n=7: 0.055±0.033 mV). In contrast, ST segment elevation in the "5 DAYS SHAM PBS" is similar to the "5 DAYS RIP PBS" group (5 DAYS SHAM, n=8: 0.134±0.034 mV; 5 DAYS RIP, n=8: 0.104±0.016 mV) (FIGS. 1 and 2).

Module 1: Sham Operation (without the RIP)

There is no significance between the three SHAM-groups (5 DAYS SHAM PBS, n=8: 0.134+0.034 mV; 5 DAYS SHAM NTG-PLACEBO, n=6: 0.131±0.043 mV; 5 DAYS SHAM NTG, n=7: 0.124±0.058 mV) (FIGS. 3 and 4).

Module 2: NO Intermittent (NTG)

In the NTG group ("5 DAYS RIP NTG") ST elevation is significantly decreased compared to the PBS group (5 DAYS RIP PBS, n=8: 0.104±0.016 mV; 5 DAYS RIP NTG, n=7: 0.052±0.030 mV). There is no significance between the PBS and NTG-PLACEBO-group (5 DAYS NTG-PLACEBO: n=6; 0.096±0.061 mV) (FIGS. 5 and 6).

Module 3: NO Continuous (ISDN Retard)

ST segment elevation in the ISDN group ("5 DAYS RIP ISDN") is decreased compared to the PBS group (5 DAYS RIP PBS, n=8: 0.104±0.016 mV; 5 DAYS RIP ISDN, n=7: 0.062±0.027 mV), but there is no significance as well as between the PBS and ISDN-PLACEBO-group (5 DAYS ISDN-PLACEBO, n=7: 0.110±0.069 mV) (FIGS. 7 and 8).

Module 4: NO Intermittent Plus ASA

ST segment elevation in the group treated with PBS and ASA is higher compared to the PBS control group (5 DAYS RIP ASA+PBS, n=7: 0.138±0.098 mV; 5 DAYS RIP PBS, n=8; 0.104±0.016 mV), but there is no significance as well as between the ASA+NTG-PLACEBO-group (5 DAYS RIP ASA+NTG-PLACEBO, n=6: 0.144±0.091 mV). In the ASA+NTG-group ST elevation is decreased compared to the group treated with ASA and PBS (5 DAYS RIP NTG+ASA, n=7: 0.088±0.071mV) (FIGS. 9 and 10).

3.4. Ventricular Arrhythmias

The importance of ventricular premature beats (VPBs) results from their possible association with an increased risk for cardiac sudden death. VPBs were stratified according to the Lown classification. A high Lown grade has been shown to predict mortality after acute myocardial infarction.

Grade 0: no ventricular ectopic beats
Grade I: occasional, isolated VPB
Grade II: frequent VPB (>1/min or 30/h)
Grade III: multiform VPB
  (a) VPB
  (b) Bigenimus
Grade IV: repetitive VPB
  (a) Couplets
  (b) Salvos
Grade V: Early VPB Module 1: Sham Operation (without the RIP)

In the "5 DAYS SHAM PBS" group 87.5% of the rats have class IVb arrhythmias and 12.5% class IVa. In the "5 DAYS SHAM NTG-PLACEBO" group 83.3% have IVb arrhythmias and 16.7% class IVa and in the "5 DAYS SHAM NTG" group 85.7% have IVb arrhythmias and 14.3% class IIIa arrhythmias (FIG. 11).

Module 2: NO Intermittent (NTG)

In the "5 DAYS RIP PBS" group, 75.0% of the rats have class IVb arrhythmias, 12.5% IVa and 12.5% class 0. Regarding the "5 DAYS RIP NTG-PLACEBO" group, 50.0% of the rats showed class IVb arrhythmias, 16.7% IVa, 16.7% class IIIb and 16.7% class 0 arrhythmias. Interestingly, the "5 DAYS RIP NTG" group shows 42.9% class IVb arrhythmias and 57.1% class 0 arrhythmias (FIG. 12).

Module 3: NO continuous (ISDN retard)

In the "5 DAYS ISDN-PLACEBO" group, 57.1% of the rats have class 1Vb arrhythmias, 14.3% class IVa and 28.6% class IIIb. The "5 DAYS RIP ISDN" group shows less severe arrhythmias with 57.1% class IVb, 28.6% class IIIb and 14.3% class 0 arrhythmias (FIG. 13).

Module 4: NO Intermittent plus ASA

In the "5 DAYS RIP ASA+PBS" group, in the group treated with ASS+NTG-PLACEBO and in the "5 DAYS RIP ASS+NTG" group 83.3% of the rats posses class IVb arrhythmias and 16.7% class IIIa (FIG. 14).

Regarding the percentage of each Lown grade of every group, a VBP score can be ascertained. The more animals show a higher grade, the higher is the VBP score (FIG. 15).

FIG. 15: VPB-Score

TABLE 1

| VPB-Score | |
|---|---|
| group | VPB-Score |
| Module 1 | |
| SHAM PBS | 5.88 |
| SHAM NTG-PLACEBO | 5.83 |
| SHAM NTG | 5.71 |
| Module 2 | |
| RIP PBS | 5.13 |
| RIP NTG-PLACEBO | 4.50 |
| RIP NTG | 2.57 |
| Module 3 | |
| RIP PBS | 5.13 |
| RIP ISDN-PLACEBO | 5.29 |
| RIP ISDN | 4.57 |
| Module 4 | |
| RIP ASA + PBS | 5.50 |
| RIP ASA + NTG-PLACEBO | 5.50 |
| RIP ASA + NTG | 5.50 |

3.5. Infarct Size

After 90 minutes of LAD occlusion and 20 minutes reperfusion, infarct size was analyzed.

The "10 DAYS RIP PBS" group has a significantly smaller infarct area compared to the "10 DAYS SHAM PBS" group (10 DAYS RIP PBS, n=6: 6.57±3.26%; 10 DAYS SHAM PBS, n=7: 13.71±6.04%). There is no significance between both 5 DAYS groups (5 DAYS SHAM PBS, n=8: 13.36±5.22%; 5 DAYS RIP PBS, n=8: 11.05±5.12%) (FIG. 16).

Module 1: Sham Operation (without the RIP)

There is no significance between the three SHAM-groups (5 DAYS SHAM PBS, n=8: 13.36±5.22%; 5 DAYS SHAM NTG-PLACEBO, n=6: 14.21±5.79%; 5 DAYS SHAM NTG, n=7: 14.09±5.18%) (FIG. 17).

Module 2: NO Intermittent (NTG)

Compared to the "5 DAYS RIP PBS", a significantly smaller infarct area is observed in the "5 DAYS RIP NTG" group (5 DAYS RIP PBS, n=8: 11.05±5.12%; 5 DAYS RIP NTG, n=7: 3.61±2.08%). There is no significance between the PBS and NTG-PLACEBO-group (5 DAYS NTG-PLACEBO: n=6; 9.80±6.79%) (FIG. 18).
Module 3: NO Continuous (ISDN retard)

The infarct size in the ISDN group ("5 DAYS RIP ISDN") is smaller compared to the PBS group (5 DAYS RIP PBS, n=8: 11.05±5.12%; 5 DAYS RIP ISDN, n=7: 7.59±4.38%), as well as the ISDN-PLACEBO-group (5 DAYS ISDN-PLACEBO, n=6: 9.97±3.65%) (FIG. 19).

Module 4: NO Intermittent Plus ASA

The infarct size in the group treated with ASA ("5 DAYS ASA+PBS") is minimally increased compared to the PBS control group (5 DAYS RIP ASA+PBS, n=6: 12.51±3.05%; 5 DAYS RIP PBS, n=8; 11.05±5.12%), as well as the ASA+NTG-PLACEBO-group (5 DAYS RIP ASA+NTG-PLACEBO, n=6: 13.92+1.71%). There is no difference between the ASA+NTG-group and the group treated with ASA and PBS (FIG. 20). However, the infarct area in the NTG group is significantly smaller compared to the ASA+NTG group (5 DAYS RIP NTG, n=7: 3.61±2.08%; 5 DAYS RIP NTG+ASS, n=6: 13.00±3.82%) (FIG. 20).

3.6. Coronary Microvascular Imaging With Micro-CT

Collateral arteries are pre-existent vessels running parallel to a major artery. In case the major artery is occluded, even for a short period of time (40 sec during this RIP), collaterals assume the blood supply. As a result, collateral arteries in this area (ROI, region of interest) start to grow in length (clearly visible by the cork screw pattern) and most notably in their diameter. So we measured the diameter of the collaterals in the ROI.

Module 1: Sham Operation (without the RIP)

There is no significance between the three SHAM-groups (5 DAYS SHAM PBS, n=3: 82.7±3.7 µm; 5 DAYS SHAM NTG-PLACEBO, n=3: 89.6 µm±10.6 µm; 5 DAYS SHAM NTG, n=3: 86.8±9.0 µm) (FIGS. 22 and 26).

Module 2: NO Intermittent (NTG)

Compared to the "5 DAYS RIP PBS", the diameters of the collaterals in the ROI in the "5 DAYS RIP NTG" group are significantly increased (5 DAYS RIP PBS, n=3: 129.8±6.9 µm; 5 DAYS RIP NTG, n=3: 158.4±9.2 µm). There is no difference between the PBS and NTG-PLACEBO-group (5 DAYS NTG-PLACEBO: n=3; 127.0±12.1 µm) (FIGS. 23 and 26).

Module 3: NO Continuous (ISDN retard)

The diameter of the collaterals in the ISDN group ("5 DAYS RIP ISDN") are enhanced compared to the PBS group (5 DAYS RIP PBS, n=3: 129.8±6.9 pµm; 5 DAYS RIP ISDN, n=3: 148.2±11.3 µm), as well as compared to the ISDN-PLACEBO group (5 DAYS ISDN-PLACEBO, n=3: 133.0±11.5 µm) (FIGS. 24 and 26).

Module 4: NO Intermittent Plus ASA

The diameter in the group treated with PBS and ASA are significantly smaller compared to the PBS control group (5 DAYS RIP PBS+ASA, n=3: 102.5±8.0 µm; 5 DAYS RIP PBS, n=3; 129.8±6.9 µm), but there is no significance compared to the ASA+NTG-PLACEBO-group (5 DAYS NTG-PLACEBO+ASA, n=3: 97.1+8.6 µm). In the ASA+NTG -group diameter are significantly increased compared to the group treated with PBS and ASA (5 DAYS RIP ASA+NTG, n=3: 124.4±5.6 µm) (FIGS. 25 and 26).

4. CONCLUSION

We examined the groups "10 DAYS SHAM PBS" and "5 DAYS SHAM PBS", each without a RIP (repetitive ischemic protocol) and the groups "10 DAYS RIP PBS" and "5 DAYS RIP PBS", each with a RIP of five and ten days.

Measurement of infarct volume after a 90 minute permanent LAD occlusion (FPO, final permanent occlusion) revealed significantly smaller infarcted areas in the 10 DAYS RIP group than in "10 DAYS SHAM" group. In contrast, after a RIP of five days, no differences became apparent in the SHAM and RIP group.

Moreover, we used ECG parameters for examinations and evaluation for the first time. We found the maximal ST elevation after FPO of the LAD showed no crucial differences between "5 DAYS RIP PBS" and SHAM groups, yet. However, after 10 days ST elevations were significantly decreased in the RIP group.

Aside from ST elevation measurement during FPO, we were able to analyze and evaluate arrhythmias in differentiated way.

Based on these novel insights into the characterization of rat RMI model, we decided to use a 5 day RIP in case of an expected stimulation of arteriogenesis. The degree of ST elevation enhancement and the infarct volume after a 10 day RIP can be obtained with pro-arteriogenic substances within a 5 day RIP, yet.

This provides additional parameters being able to approve our results of infarct volume measurement.

The intermittent application of NTG solution (twice daily on buccal mucosa) decreased serious arrhythmias of the rat heart during FPO compared to the control group. Additionally, infarct volume is decreased by more than 50% after 90 minutes FPO compared to the control group. This reduction in infarct size is not even obtainable with controls set to a 10 days RTP. Furthermore, a treatment with NTG solution significantly attenuated ST elevation during FPO. On the basis of the µCT analyses, significantly enlarged collateral arteries were measurable.

The treatment of the rats with ISDN retard (once daily intragastrally) also led to decreases in ST elevation during FPO, less arrhythmias and reduced infarct volumes. However, these improvements of infarct parameters are less distinct compared with NTG treatment. Moreover, they did not show any significance.

Compared to controls, the treatment with ASA showed an impairment of ECG parameters and an increase of infarct volumes due to impaired collateral growth. These negative effects of ASA on arteriogenesis are already known. Interestingly, they can be partly abolished through an additional NTG treatment (twice daily on buccal mucosa). Thus, collateral diameters were enlarged in the ROI and ECG parameters were enhanced. Nevertheless, infarct volumes after FPO showed no reduction.

The SHAM groups did not differ among each other.

Further on, there were no differences measured between the Placebo groups and their corresponding control groups.

In conclusion, the presented results indicate that an intermittent treatment with NTG solution decreases the size of an experimentally induced myocardial infarct. In addition, effects on cardiac rhythm may ameliorate. These insights are of outstanding relevance for clinical aspects.

EXAMPLE 2

Clinical Study

This study aims to investigate the effects of a supervised, physician-controlled standardized exercise program for the symptomatic treatment, functional improvement and an augmentation of the arteriogenic capacity in patients with chronic stable CAD.

1 Study Design
1.1 Hypotheses and Study Arms
1.1.1 Hypotheses
I Active physician-controlled exercise training with intermittent application of GTN is superior to active physician-controlled exercise training without GTN.

(A+)>(A−)

II Passive physician-controlled exercise training (CardioAccel®) with intermittent application of GTN is superior to passive physician-controlled exercise training without GTN.

(P+)>(P−)

III Conservative CAD therapy with intermittent application of GTN is superior to conservative CAD therapy without GTN.

(C+)>(C−)

1.1.2 Study Arms
A+ Active physician-controlled exercise training with intermittent application of GTN
A− Active physician-controlled exercise training
P+ Passive physician-controlled exercise training (Cardio-Accel®) with intermittent application of GTN
P− Passive physician-controlled exercise training (Cardio-Accel®)
C+ Conservative CAD therapy with intermittent application of GTN
C− Conservative CAD therapy Patients may use GTN in case of angina pectoris, however will be supplied with an additional study GTN for the study use.

Active Physician-Controlled Exercise Training with Intermittent Application of GTN.

Best medical therapy and usual care as detailed in the current guidelines (AHA, ESC) for the care for patients with chronic stable angina. Daily (Mon-Fri) physical exercise intervals (treadmill) of 30 min (≥1 W/kg bw), following risk stratification and individual calculation and adjustment of training intensity as detailed in the current EACPR guidelines, for a total of six weeks. GTN use for the treatment of angina episodes is permitted. In addition, GTN 0.4 mg is administered 2-5 min before the onset of exercise.

Active Physician-Controlled Exercise Training.

Best medical therapy and usual care as detailed in the current guidelines (AHA, ESC) for the care for patients with chronic stable angina. Daily (Mon-Fri) physical exercise intervals (treadmill) of 30 min (≥1 W/kg bw), following risk stratification and individual calculation and adjustment of training intensity as detailed in the current EACPR guidelines, for a total of six weeks. GTN use for the treatment of angina episodes is permitted.

Passive Physician-Controlled Exercise Training (CardioAccel®) with Intermittent Application of GTN.

Best medical therapy and usual care as detailed in the current guidelines (AHA, ESC) for the care for patients with chronic stable angina. Daily (Mon-Fri) CardioAccel® treatment intervals of one hour per day for a total of six weeks, as detailed (Arora R R, Chou T M, Jain D, Fleishman B, Crawford L, McKiernan T, Nesto RW. The multicenter study of enhanced external counterpulsation (MUST-EECP): effect of EECP on exercise-induced myocardial ischemia and anginal episodes. J Am Coll Cardiol. 1999 June;33(7): 1833-40). GTN use for the treatment of angina episodes is permitted. In addition, GTN 0.4 mg is administered 2-5 min before the onset of exercise. GTN use for the treatment of angina episodes is permitted.

Passive Physician-Controlled Exercise Training (CardioAccel®).

Best medical therapy and usual care as detailed in the current guidelines (AHA, ESC) for the care for patients with chronic stable angina. Daily (Mon-Fri) CardioAccel® treatment intervals of one hour per day for a total of six weeks, as detailed (Arora et al., supra). GTN use for the treatment of angina episodes is permitted.

Conservative CAD Therapy with Intermittent Application of GTN.

Best medical therapy and usual care as detailed in the current guidelines (AHA, ESC) for the care for patients with chronic stable angina. GTN use for the treatment of angina episodes is permitted. In addition, GTN 0.4 mg is administered once daily, preferably before the onset of a voluntary activity of daily life.

Conservative CAD Therapy.

Best medical therapy and usual care as detailed in the current guidelines (AHA, ESC) for the care for patients with chronic stable angina. GTN use for the treatment of angina episodes is permitted.

1.2 Clinical Trial Design
1.2.1 Clinical Trial Design—general
The study is designed as a
prospective
randomized
multicenter (German Site, US-Site)
clinical trial, to evaluate glyceryl trinitrate (Nitrolingual®) effects on exercise capacity, the proposed pathophysiological mechanism being an induction of pro-arteriogenic effects.

1.2.2 Study Endpoints
Primary
Changes in
functional exercise capacity, as measured on visit 3 by peak volume of oxygen uptake ($VO_2$ max) and maximum oxygen uptake at anaerobic threshold ($VO_2$ max AT) from baseline in a standardized exercise treadmill test (sETT).

Secondary
Changes in
(1) Time to exercise-induced ischemia as measured by time to a >1-mm ST-segment depression in a standardized exercise treadmill test (sETT),
(2) the hemodynamic responses to the sETT, as quantified by the rate-pressure product (RPP)[1], which is defined as the systolic blood pressure (mm Hg) multiplied by the heart rate (bpm). Heart rate, blood pressure, and ST segment trends are electronically measured at the J-point+60 ms,

[1] The Rate-pressure product (RPP) is a sensitive index of myocardial oxygen consumption (mVO2). Patients are categorized by the rate pressure product (RPP) that existed at the time of maximum ST depression. In the absence of ST depression, the maximum RPP is recorded.

(3) the number of angina episodes per day,
(4) exercise duration on sETT,
(5) Relative Peak Slope Index (RPSI),
(4) Doppler-derived maximal systolic acceleration [ACCmax],
(5) CCS and NYHA functional status,
(6) Duke Treadmill Score[2],

[2] The Duke treadmill score calculates risk; it equals the exercise time in minutes minus (5 times the ST-segment deviation, during or after exercise, in millimeters) minus (4 times the angina index, which has a value of "0" if there is no angina, "1" if angina occurs, and "2" if angina is the reason for stopping the test). Among outpatients with suspected CAD, the two thirds of patients with scores indicating low risk had a four-year survival rate of 99% (average annual mortality rate 0.25%), and the 4% who had scores indicating high risk had a four-year survival rate of 79% (average annual mortality rate 5%). The score works well for both inpatients and outpatients, and preliminary data suggest that the score works equally well for men and women [Gibbons et al., 2003 ANA/ACC Guideline]

(7) Incidence of cardiovascular events during the treatment phase and
(8) same as primary endpoint, but one month after intervention period.

1.2.3 Patients

Eligible patients must be clinically stable, receiving before enrolment an antianginal and CAD therapy that is in full accordance with the current ESC/AHA guidelines for the treatment of chronic stable CAD.

Prohibited Medication
   long-acting nitrates
   Sildenafil etc.
   Anti-inflammatory compounds (other than aspirin) such as steroids or etanercept etc.

| Inclusion Criteria: |
| --- |
| Age > 18 yrs |
| Documented evidence of stable coronary artery disease by either positive nuclear exercise stress testing, angiographically documented coronary stenosis or history of documented ST-elevation or myocardial infarction |

| Exclusion Criteria: |
| --- |
| Nitrate intolerance or intolerance to any component of the study medication. |
| Medication that poses a risk of pharmacologically interacting with GTN. |
| Acute coronary syndrome or unstable angina ≤6 weeks prior. |
| Left main stenosis of ≥50%. |
| PCI or CABG ≤3 months prior. |
| Coronary angiography ≤3 weeks prior. |
| Congestive heart failure/EF of ≤30%. |
| Valvular heart disease or myocarditis. |
| Uncontrolled hypertension with blood pressure values ≥180/100 mmHg |
| Severe symptomatic PAD, varicosis, deep vein thrombosis (current or in documented medical history), phlebitis or ulcer. |
| Coagulation disorder or therapeutic anticoagulation. |
| Cardiac arrhythmias that interfere with ECP triggering. |
| ECG characteristics that would invalidate ST segment monitoring: baseline ST segment depression, pacemaker-dependent rhythms, QRS duration >0.12 s, arrhythmias other than sinus arrhythmia. |
| FEV1 < 1.5l. |
| Current participation in a cardiac exercise rehabilitation program. |

Randomization

Enrolled patients are randomized in a 1:1:1 ratio to receive/undergo either active training, CardioAccel® therapy or usual care, i.e. a continuation of the baseline treatment in accordance with current guidelines. Within these groups, patients are randomized in a 1:1 ration to either a "+GTN" or a "−GTN" group to receive glycerol trinitrate either in addition to their standard medication, or not.

1.2.4 Study Planning, Conduction and Management

The trial is planned by Arteriogenesis Network Art.Net.
Study management will be covered by Arteriogenesis Network Art.Net.
   c/o Campus Technologies Freiburg GmbH
   Technology Transfer of the University of Freiburg
   CEO: Prof. Dr. Bernhard Arnolds
   Stefan-Meier Straße 8, 79104 Freiburg (Germany)
   Phone:+49 (0)761 203 4990
   Facsimile:+49 (0)761 203 4992
   Sponsor of the trial is CTF.
The reporting structures and reporting schemes will be detailed after the participating centers have been assigned.
Research Sites
   participating centers: to be determined
   contact in case of questions, dissemination of info
   contact in case of adverse event, dissemination of info 1.2.5 Study Flow Chart and Protocol
The Study Flow Chart is given in FIG. 27.

1.2.6 Treatment Assignment
Randomization will be done at the conducting centers via envelopes.
Stratification will be done according to age-groups, gender and morbidity.
Study visits are conducted by an investigator.
Study centers in advance assign blinded investigators that are unaware of the randomization, and who carry out the medical examinations and testing at Baseline and First Follow-up.
At each study visit, patients are instructed to fill in a short standardized quality of life assessment form (SF-36[3]).

[3] http://www.rand.org/health/surveys_tools/mos/mos_core_36item.html

Patients assigned to the C+/ C− groups are contacted on a regular basis by study personnel to help control potential bias effects as these subjects do not have as regular contacts with study personnel as do the CardioAccel® or exercise groups.

1.2.7 Study Visits

Visit 1: Eligibility Screening (day 1)
   Medical history, including previous interventions, physical exam
   Enrolment y/n Visit 2: Baseline Visit (until day 14 (+3 days))
   Detailed medical history and physical exam, including assessment of number of angina episodes per day, CCS and NYHA status and assessment of voluntary physical activity.
   Treadmill testing on a standard, calibrated treadmill equipment with cardiopulmonary testing capability (modified Naughton protocol): functional exercise capacity ($VO_2$ max and $VO_2$ max AT), time to exercise-induced ischemia as measured by time to a >1-mm ST-segment depression, rate-pressure product (RPP), heart rate, blood pressure, and ST segment trends electronically measured at the J-point+60 ms, exercise duration, DUKE treadmill score,
   continuous monitoring of vital signs incl. 12-lead ECG and $VO_2$, with $VO_2$max defined as $VO_2$ at maximum level of exercise the individual patient is able to achieve (respiratory ratio>1, anaerobic threshold)
   Relative Peak Slope Index (RPSI)
   Doppler-derived maximal systolic acceleration [ACC-max]
   Randomization Interim Visits (Non-Scheduled)
Patients are advised to contact the study center at any time regarding their medical condition. Patients are scheduled to return for their first follow-up visits at 6 weeks after randomization.

Visit 3: Short-Term Follow-Up (1-3 Days After Intervention Period)
   Medical history and physical exam, including assessment of number of angina episodes per day, CCS and NYHA status and assessment of voluntary physical activity.
   Treadmill testing on a standard, calibrated treadmill equipment with cardiopulmonary testing capability (modified Naughton protocol): functional exercise capacity ($VO_2$ max and $VO_2$ max AT), time to exercise-induced ischemia as measured by time to a >1-mm ST-segment depression, rate-pressure product (RPP), heart rate, blood pressure, and ST segment trends electronically measured at the J-point+60 ms, exercise duration, DUKE treadmill score, continuous monitoring of vital signs incl. 12-lead ECG and $VO_2$, with $VO_2$max defined as $VO_2$ at maximum level of exercise the individual patient is able to achieve (respiratory ratio>1, anaerobic threshold)

Relative Peak Slope Index (RPSI)

Doppler-derived maximal systolic acceleration [ACC-max]

Incidence of cardiovascular events during the treatment phase

Visit 4: Long-Term Follow-Up (1 Month After Intervention Period)

(The rational of this study point is to evaluate the long term effect of the study medication after the intervention period).

Medical history and physical exam, including assessment of number of angina episodes per day, CCS and NYHA status and assessment of voluntary physical activity.

Treadmill testing on a standard, calibrated treadmill equipment with cardiopulmonary testing capability (modified Naughton protocol): functional exercise capacity ($VO_2$ max and $VO_2$ max AT), time to exercise-induced ischemia as measured by time to a >1-mm ST-segment depression, rate-pressure product (RPP), heart rate, blood pressure, and ST segment trends electronically measured at the J-point+60 ms, exercise duration, DUKE treadmill score, continuous monitoring of vital signs incl. 12-lead ECG and $VO_2$, with $VO_2$max defined as $VO_2$ at maximum level of exercise the individual patient is able to achieve (respiratory ratio >1, anaerobic threshold)

Relative Peak Slope Index (RPSI)

Doppler-derived maximal systolic acceleration [ACC-max]

1.2.8 Statistical Considerations

The main efficacy parameter is functional exercise capacity, as measured by peak volume of oxygen uptake (VO2 max) and maximum oxygen uptake at anaerobic threshold (VO2 max AT) in a standardized exercise treadmill test (sETT). We assume no difference at baseline but significantly higher values in the GTN groups at follow-up.

Statistical Methods

There are two major sources of variance to be considered in this trial: GTN treatment effects and effects of active training/passive training/conservative therapy. Accordingly data will be analysed in a two-way ANOVA. Any therapy effects not related to GTN will be reported in a descriptive way without inference statistic.

For secondary parameters parametric or non-parametric tests will be applied as appropriate.

Sample Size/Power

To establish the necessary sample size for the proposed two-way-ANOVA, we made the following assumptions (based on literature review and internal data): statistical power=80%, standard deviation for outcome measure=15% of mean, effect size (group difference in change between GTN yes/no)=5% of mean. Power was established in a Monte Carlo simulation based on 10000 repeats per sample size over a range of n per group from 30 to 60 patients. This simulation established a minimum sample size of 48 subjects per group, to allow for potential drop-outs we propose to include 50 subjects per group, resulting in a total sample size of 300 patients.

1.3 Ethical and Legal Aspects

The investigators plan and conduct any experiments involving humans, including identifiable samples taken from humans and identifiable data, in compliance with (a) the Declaration of Helsinki (Ethical Principles for Medical Research Involving Human Subjects) concluded by the World Medical Association (WMA) in June 1964, as last revised;

(b) the ICH Harmonised Tripartite Guideline: Guideline for Good Clinical Practice E6/International Conference on Harmonisation of Technical Requirements for Registration of Pharmaceuticals for Human Use (ICH E6, 1 May 1996) as well as (c) applicable German regulations (e.g. Arzneimittelgesetz) in their current forms, as well as applicable FDA regulations (e.g. Guidance for Sponsors, Investigators, Informed Consent Elements, 21 CFR § 50.25(c).

5. LIST OF ABBREVIATIONS $ACC_{max}$: Doppler-derived maximal systolic acceleration
Art.Net.: Network Subcontractors of CTF
CAD: Coronary Artery Disease
CardioAccel®: personalized counterpulsation therapy
CCS: Canadian Class Society (Angina classification)
CTF: Campus Technologies Freiburg
FSS: fluid shear stress
GTN: glyceryl trinitrate
IABP: intra-aortic ballon pump
NYHA: New York Heart Association
RPSI: Relative Peak Slope Index
sETT: a standardized exercise treadmill test
SMC: vascular smooth muscle cell
$VO_2$ max: peak volume of oxygen uptake
$VO_2$ max AT: maximum oxygen uptake at anaerobic threshold The invention further relates to the following items:

1. A method of treating or preventing an arterial insufficiency, wherein an NO donor is administered in an intermitting manner to a subject in an amount effective for the induction of arteriogenesis.
2. The method of item 1, wherein the arterial insufficiency is due to insufficient oxygen or blood supply of a tissue supplied by the artery or a bypass or shunt during physical rest or exercise.
3. The method of any of items 1 or 2, wherein the arterial insufficiency is due to an increased demand of oxygen or blood flow of a tissue supplied by the artery or a bypass or shunt.
4. The method of any of items 1 to 3, wherein the arterial insufficiency is characterized by a partial or complete occlusion of an arterial vessel.
5. The method of any of items 1 to 4, wherein the arterial insufficiency is due to the deposition of material in the blood vessels.
6. The method of any of items 1 to 5, wherein the arterial insufficiency is due to an external or internal compression of an artery.
7. The method of any of items 1 to 6, wherein the arterial insufficiency is a vascular disease.
8. The method of any of items 1 to 6, wherein the arterial insufficiency is a disease selected from the group consisting of atherosclerosis, an ischemic disease and a further chronic arterial disease.
9. The method of any of items 1 to 6, wherein the arterial insufficiency is a coronary arterial insufficiency.
10. The method of any of items 1 to 6, wherein the arterial insufficiency is a cerebral arterial insufficiency.
11. The method of any of items 1 to 6, wherein the arterial insufficiency is a peripheral arterial insufficiency.

12. The method of any of items 1 to 6, wherein the arterial insufficiency is an intestinal arterial insufficiency.
13. The method of any of items 1 to 6, wherein the arterial insufficiency is an urogenital arterial insufficiency.
14. The method of any of items 1 to 6, wherein the arterial insufficiency is a nerval arterial insufficiency.
15. The method of any of items 1 to 6, wherein the arterial insufficiency is in the context of scleroderma.
16. The method of any of items 1 to 6, wherein the arterial insufficiency is a central retinal artery insufficiency.
17. The method of any of items 1 to 16, wherein the arterial insufficiency is characterized by an absence of an endothelial dysfunction.
18. The method of any of items 1 to 17, wherein the NO donor is nitric oxide, sodium nitroprusside, nitroglycerin (glyceryl trinitrate), isosorbide mononitrate, isosorbide dinitrate, pentaerythritol tetranitrate (PETN), molsidomin, amyl nitrite or nicorandil.
19. The method of any of items 1 to 6, wherein the NO donor is a short acting NO donor.
20. The method of any of items 1 to 19, wherein the NO donor is Nitroglycerin.
21. The method of any of items 1 to 19, wherein the NO donor at least once a day and at least on one day a week for at least two weeks.
22. The method of any of items 1 to 21, wherein the NO donor is administered for a period of several weeks or months.
23. The method of any of items 1 to 22, wherein the NO donor is administered in conjunction with an exogenous stimulation of the pulsatile shear forces in the artery.
24. The method of item 23, wherein the NO donor is administered in the time period of 30 minutes before the onset of the exogenous stimulation until 30 minutes after the termination of the exogenous stimulation.
25. The method of item 24, wherein the NO donor is administered in the time period of 15 minutes before the exogenous stimulation until 30 minutes after the onset of the exogenous stimulation.
26. The method of any of items 23 to 25, wherein said stimulation is achieved by physical exercise or the application of an endogenous force to the arterial vessel.
27. The method of any of item 1 to 26, wherein the method aims at the prevention of said arterial insufficiency.
28. The method of any of items 1 to 27, wherein the NO donor is administered lingually, sublingually, inhalatively, bucally, transmucosally or oromucosally.
29. An NO donor for use in a method for the prevention or treatment of an arterial insufficiency, wherein the NO donor is administered in an intermitting manner in an amount effective for the induction of arteriogenesis.
30. The NO donor for use according to item 29, with the features as defined in any of items 2 to 28.
31. A method of the suppression of negative effects associated with any treatment of an arterial insufficiency which is anti-anteriogenic or inhibiting arteriogenesis, comprising administering to a subject subjected to said treatment an NO donor in an amount and manner effective for the induction of arteriogenesis.
32. An NO donor for use in a method of the suppression of negative effects associated with any treatment of an arterial insufficiency which is anti-anteriogenic or inhibiting arteriogenesis, wherein the NO donor is administered to a subject subjected to said treatment in an amount and manner effective for the induction of arteriogenesis.
33. The NO donor for use according to item 32 or the method according to item 32, with the features as defined in any of items 2 to 28.
34. A method for the prevention or treatment of a cardiac arrhythmia, wherein an NO donor is administered to a subject in an amount and manner effective for the treatment of said cardiac arrhythmia.
35. The method of item 34, with the features as defined in any of items 18 to 28.
36. An NO donor for use in a method for the prevention or treatment of a cardiac arrhythmia, wherein the NO donor is administered to a subject in an amount and manner effective for the treatment of said cardiac arrhythmia.
37. The NO donor for use according to item 36, with the features as defined in any of items 18 to 28.
38. A method of promoting collateral circulation comprising the step of exposing a subject to a therapeutically effective amount of an NO donor wherein the therapeutically effective amount of the NO donor promotes arteriogenesis sufficient to augment collateral circulation in a physiological or pathological condition.
39. The method of item 38, wherein the subject suffers from an arterial insufficiency.
40. The method of item 39, with the features as defined in any of items 2 to 28.

The invention claimed is:

1. A method of treating peripheral arterial disease in a subject in need thereof, the method comprising administering to the subject the short acting NO donor nitroglycerin in an intermitting manner in an amount effective for the induction of arteriogenesis,
wherein the nitroglycerin is administered lingually, sublingually, inhalatively, transmucosally or oromucosally at least five days a week for at least four weeks, and
wherein the short acting NO donor nitroglycerin is the only NO donor administered in the course of said method.

2. The method of claim 1, wherein the nitroglycerin is administered twice or three times daily.

3. The method of claim 2, wherein the time period between any two daily administrations is selected from the group consisting of 4 hours, 8 hours, 10 hours and 12 hours.

4. The method of claim 2, wherein the nitroglycerin is administered three times daily and the time period between the first and second administrations and the time period between the second and third daily administrations differ.

5. The method of claim 1, wherein the nitroglycerin is administered 6 or 7 days per week.

6. The method of claim 1, wherein the nitroglycerin is administered for 4-8, 4-10, or 4-12 weeks.

7. The method of claim 1, wherein the nitroglycerin is administered in a dosage of between 0.1 and 8 mg per day.

8. The method of claim 1, wherein nitroglycerin is administered in a dosage of between 0.1 and 10 mg per day.

9. The method of claim 7, wherein the nitroglycerin is administered in a dosage of between 0.2 and 0.8 mg for up to a maximum of 4 times daily.

10. The method of claim 1, wherein the nitroglycerin is administered in conjunction with exogenous stimulation of arterial pulsatile shear forces.

11. The method of claim 10, wherein the nitroglycerin is administered 30 minutes prior to the onset of exogenous stimulation until 30 minutes post termination of the exogenous stimulation.

12. The method of claim 10, wherein the exogenous stimulation is achieved by physical exercise or the application of an endogenous force to the artery.

13. The method of claim 1, wherein the peripheral arterial disease is characterized by a partial or complete occlusion of an arterial vessel.

14. The method of claim 1, wherein the peripheral arterial disease is due to the deposition of material in the blood vessels, or wherein the peripheral arterial disease is due to an external or internal compression of an artery.

15. The method of claim 1, wherein the method prevents the symptoms of peripheral arterial disease.

16. The method of claim 1, wherein the nitroglycerin is administered in form of a spray, a chewable capsule, an inhalable gas, an inhalable aerosol, granules, powder or a tablet.

\* \* \* \* \*